(12) United States Patent
Doshi et al.

(10) Patent No.: US 12,286,474 B2
(45) Date of Patent: *Apr. 29, 2025

(54) ANTI-CD38 ANTIBODIES FOR TREATMENT OF ACUTE MYELOID LEUKEMIA

(71) Applicant: Janssen Biotech, Inc., Horsham, PA (US)

(72) Inventors: Parul Doshi, Chester Springs, PA (US); Gwenn Danet-Desnoyers, Philadelphia, PA (US); Cedric Dos Santos, San Bruno, CA (US); Amy Sasser, Doylestown, PA (US); Xiaochuan Shan, Philadelphia, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 306 days.

This patent is subject to a terminal disclaimer.

(21) Appl. No.: 17/005,039

(22) Filed: Aug. 27, 2020

(65) Prior Publication Data
US 2021/0047401 A1   Feb. 18, 2021

Related U.S. Application Data

(63) Continuation of application No. 14/956,890, filed on Dec. 2, 2015, now Pat. No. 10,793,630.

(60) Provisional application No. 62/087,442, filed on Dec. 4, 2014.

(51) Int. Cl.
| | |
|---|---|
| C07K 16/28 | (2006.01) |
| A61K 31/704 | (2006.01) |
| A61K 31/706 | (2006.01) |
| A61K 31/7068 | (2006.01) |
| A61K 39/00 | (2006.01) |
| A61K 39/395 | (2006.01) |
| A61K 45/06 | (2006.01) |
| A61N 5/10 | (2006.01) |

(52) U.S. Cl.
CPC ............ *C07K 16/28* (2013.01); *A61K 31/704* (2013.01); *A61K 31/706* (2013.01); *A61K 31/7068* (2013.01); *A61K 39/395* (2013.01); *A61K 39/39558* (2013.01); *A61K 45/06* (2013.01); *A61N 5/1027* (2013.01); *A61N 5/1045* (2013.01); *A61N 5/1084* (2013.01); *C07K 16/2896* (2013.01); *A61K 39/001126* (2018.08); *A61K 2039/505* (2013.01); *C07K 2317/21* (2013.01); *C07K 2317/56* (2013.01); *C07K 2317/565* (2013.01); *C07K 2317/73* (2013.01); *C07K 2317/732* (2013.01); *C07K 2317/734* (2013.01)

(58) Field of Classification Search
CPC .............. C07K 16/28; A61K 39/39558; A61K 2039/505; A61K 39/001126
See application file for complete search history.

(56) References Cited

U.S. PATENT DOCUMENTS

| | | |
|---|---|---|
| 6,737,056 B1 | 5/2004 | Presta |
| 7,183,387 B1 | 2/2007 | Presta |
| 7,223,397 B1 | 5/2007 | Rosenblum et al. |
| 7,829,673 B2 | 11/2010 | DeWeers |
| 7,829,693 B2 | 11/2010 | Kreutzer et al. |
| 8,008,449 B2 | 8/2011 | Korman et al. |
| 8,088,896 B2 | 1/2012 | Tesar et al. |
| 8,153,765 B2 | 4/2012 | Park et al. |
| 8,318,154 B2 | 11/2012 | Frost et al. |
| 8,354,509 B2 | 1/2013 | Carven et al. |
| 8,431,380 B2 | 4/2013 | Bookbinder |
| 9,040,050 B2 | 5/2015 | Van De Winkel |
| 9,603,927 B2 | 3/2017 | Doshi |
| 9,732,154 B2 | 8/2017 | Doshi |
| 10,385,135 B2 | 8/2019 | Janssen et al. |
| 10,556,961 B2 | 2/2020 | Doshi |
| 10,604,580 B2 | 3/2020 | Lokhorst |
| 10,668,149 B2 | 6/2020 | Doshi et al. |
| 10,766,965 B2 | 9/2020 | Chaulagain |
| 10,781,261 B2 | 9/2020 | Janssen et al. |
| 10,793,630 B2 | 10/2020 | Doshi et al. |
| 10,800,851 B2 | 10/2020 | Doshi |
| 11,021,543 B2 | 6/2021 | Ahmadi et al. |
| 11,566,079 B2 | 1/2023 | Jansson et al. |
| 11,618,787 B2 | 4/2023 | Ahmadi et al. |
| 11,634,499 B2 | 4/2023 | Larmore |
| 11,708,419 B2 | 7/2023 | Jansson et al. |
| 11,708,420 B2 | 7/2023 | Jansson et al. |
| 11,713,355 B2 | 8/2023 | Doshi et al. |
| 11,732,051 B2 | 8/2023 | Jansson et al. |
| 12,060,432 B2 | 8/2024 | Doshi et al. |
| 12,091,466 B2 | 9/2024 | Chaulagain et al. |
| 2004/0141982 A1 | 7/2004 | Lust et al. |

(Continued)

FOREIGN PATENT DOCUMENTS

| | | |
|---|---|---|
| AU | 2013203186 A1 | 5/2013 |
| CL | 2013001944 A1 | 9/2014 |

(Continued)

OTHER PUBLICATIONS

"A Prospective Phase II of Daratumumab in Previously Treated Systemic Light Chain (AL) Amyloidosis", published online at //cms.cws.net/content/beta.myelomasociety.org/files/2017ash/Roussel,%20Murielle-ASH2017.pdf (2017).

Aarhust, et al., "ADP-ribosyl Cyclase and CD38 Catalyze the Synthesis of a Calcium mobilizing Metabolite from NADP+," The Journal of Biological Chemistry, 270(51):30327-30333 (1995).

Abdi, J. et al., "Drug resistance in multiple myeloma: latest findings and new concepts on molecular mechanisms," Oncotarget, vol. 4; No. 12; 2186-2207 (2013).

Adriouch et al., "Extracellular NAD+: a danger signal hindering regulatory T cells," Microbes and Infection, 14:1284-1292 (2012).

(Continued)

*Primary Examiner* — Sheela J. Huff
(74) *Attorney, Agent, or Firm* — HAMILTON, BROOK, SMITH & REYNOLDS, P.C.

(57) ABSTRACT

The present invention relates to methods of treatment of acute myeloid leukemia with anti-CD38 antibodies.

12 Claims, 16 Drawing Sheets

Specification includes a Sequence Listing.

(56) References Cited

U.S. PATENT DOCUMENTS

| | | |
|---|---|---|
| 2004/0268425 A1 | 12/2004 | Bookbinder et al. |
| 2006/0257397 A1 | 11/2006 | Throsby |
| 2007/0148178 A1 | 6/2007 | Fyfe et al. |
| 2008/0063642 A1 | 3/2008 | Adelman et al. |
| 2008/0166344 A1 | 7/2008 | Nakahara et al. |
| 2009/0076249 A1 | 3/2009 | Deweers et al. |
| 2009/0148449 A1 | 6/2009 | DeWeers |
| 2009/0304687 A1 | 12/2009 | Drachman |
| 2009/0304710 A1 | 12/2009 | Park et al. |
| 2010/0068136 A1 | 3/2010 | Hansen |
| 2010/0074885 A1 | 3/2010 | Schiff et al. |
| 2010/0092489 A1 | 4/2010 | van de Winkel et al. |
| 2010/0285004 A1 | 11/2010 | Tesar et al. |
| 2011/0044997 A1 | 2/2011 | Adler et al. |
| 2011/0053247 A1 | 3/2011 | Baker et al. |
| 2011/0066111 A1 | 3/2011 | Teschner et al. |
| 2011/0076273 A1 | 3/2011 | Adler et al. |
| 2011/0099647 A1 | 4/2011 | De Weers et al. |
| 2011/0293606 A1 | 12/2011 | Lejeune |
| 2011/0300157 A1 | 12/2011 | Devy et al. |
| 2012/0171153 A1 | 7/2012 | Frost et al. |
| 2012/0201827 A1 | 8/2012 | Elias |
| 2012/0219551 A1 | 8/2012 | Johnson et al. |
| 2012/0231008 A1 | 9/2012 | Guo et al. |
| 2012/0244110 A1 | 9/2012 | Chen et al. |
| 2012/0258081 A1 | 10/2012 | Corringham et al. |
| 2012/0259095 A1 | 10/2012 | Beliard et al. |
| 2012/0295864 A1 | 11/2012 | Taube et al. |
| 2013/0022588 A1 | 1/2013 | Yang et al. |
| 2013/0109593 A1 | 5/2013 | Hartmann et al. |
| 2013/0137134 A1 | 5/2013 | Mordechai et al. |
| 2013/0209355 A1 | 8/2013 | De Weers et al. |
| 2013/0302400 A1 | 11/2013 | Maneval et al. |
| 2013/0309250 A1 | 11/2013 | Cogswell et al. |
| 2013/0323247 A1 | 12/2013 | Zugmaier et al. |
| 2014/0051662 A1 | 2/2014 | Moussy et al. |
| 2014/0099254 A1 | 4/2014 | Chang et al. |
| 2014/0155584 A1 | 6/2014 | Elias et al. |
| 2014/0248238 A1 | 9/2014 | Wilson et al. |
| 2014/0271644 A1 | 9/2014 | Elias et al. |
| 2014/0309183 A1 | 10/2014 | Kerr |
| 2014/0314800 A1 | 10/2014 | Mathieu et al. |
| 2014/0356318 A1 | 12/2014 | Barken |
| 2015/0118251 A1 | 4/2015 | Deslandes |
| 2015/0125447 A1 | 5/2015 | Heider |
| 2015/0231235 A1 | 8/2015 | Van De Winkel |
| 2015/0246123 A1 | 9/2015 | Doshi |
| 2015/0246975 A1 | 9/2015 | Doshi |
| 2015/0376276 A1 | 12/2015 | Lewis et al. |
| 2016/0009683 A1 | 1/2016 | Hansen et al. |
| 2016/0067205 A1 | 3/2016 | Lokhorst |
| 2016/0222106 A1 | 8/2016 | Doshi et al. |
| 2016/0367663 A1 | 12/2016 | Doshi et al. |
| 2016/0376373 A1 | 12/2016 | Ahmadi |
| 2017/0000885 A1 | 1/2017 | Rhee et al. |
| 2017/0008966 A1 | 1/2017 | Chaulagain |
| 2017/0044265 A1 | 2/2017 | Ahmadi |
| 2017/0107295 A1 | 4/2017 | Lokhorst |
| 2017/0121414 A1 | 5/2017 | Jansson et al. |
| 2017/0121417 A1 | 5/2017 | Jansson et al. |
| 2017/0174780 A1 | 6/2017 | Doshi |
| 2017/0320961 A1 | 11/2017 | Doshi |
| 2018/0117150 A1 | 5/2018 | O'Dwyer |
| 2019/0127479 A1 | 5/2019 | Ahmadi et al. |
| 2019/0144557 A1 | 5/2019 | Ahmadi et al. |
| 2019/0233533 A1 | 8/2019 | Otten |
| 2019/0330363 A1 | 10/2019 | Janssen et al. |
| 2019/0352421 A1 | 11/2019 | Adams et al. |
| 2020/0002433 A1 | 1/2020 | Janssen et al. |
| 2020/0121588 A1 | 4/2020 | Campbell et al. |
| 2020/0148782 A1 | 5/2020 | Jansson et al. |
| 2020/0223936 A1 | 7/2020 | Doshi et al. |
| 2020/0231697 A1 | 7/2020 | Jansson et al. |
| 2020/0268847 A1 | 8/2020 | Qi |
| 2020/0308284 A1 | 10/2020 | Bandekar et al. |
| 2020/0308296 A1 | 10/2020 | Bandekar et al. |
| 2020/0316197 A1 | 10/2020 | Bandekar et al. |
| 2020/0330593 A1 | 10/2020 | Bandekar et al. |
| 2020/0339701 A1 | 10/2020 | Jansson et al. |
| 2020/0392242 A1 | 12/2020 | Liu |
| 2020/0397896 A1 | 12/2020 | Liu |
| 2020/0405854 A1 | 12/2020 | Liu et al. |
| 2020/0407459 A1 | 12/2020 | Chaulagain et al. |
| 2021/0061920 A1 | 3/2021 | Doshi et al. |
| 2021/0095042 A1 | 4/2021 | Jansson et al. |
| 2021/0107991 A1 | 4/2021 | Jansson et al. |
| 2021/0403592 A1 | 12/2021 | Ahmadi et al. |
| 2022/0041745 A1 | 2/2022 | Bandekar et al. |
| 2022/0062415 A1 | 3/2022 | Xie et al. |
| 2022/0204638 A1 | 6/2022 | Liu et al. |
| 2022/0275090 A1 | 9/2022 | Alvarez Arias |
| 2022/0275101 A1 | 9/2022 | Schecter |
| 2022/0401465 A1 | 12/2022 | Fan et al. |
| 2023/0340145 A1 | 10/2023 | Ahmadi et al. |
| 2023/0391884 A1 | 12/2023 | Otten |
| 2024/0092927 A1 | 3/2024 | Jansson et al. |

FOREIGN PATENT DOCUMENTS

| | | |
|---|---|---|
| CL | 2016002158 A1 | 7/2017 |
| EA | 009383 B1 | 12/2007 |
| EA | 015584 B1 | 10/2011 |
| EA | 201390993 | 12/2013 |
| EP | 2561868 A1 | 2/2013 |
| EP | 2567976 A2 | 3/2013 |
| EP | 2 459 167 B1 | 5/2013 |
| EP | 2 477 603 B1 | 3/2016 |
| JP | 2002-534396 A | 10/2002 |
| JP | 2008-533977 A | 8/2008 |
| JP | 2009-511033 A | 3/2009 |
| JP | 2010-504363 A | 2/2010 |
| JP | 2010-506582 A | 3/2010 |
| JP | 2014-509837 A | 4/2014 |
| NZ | 576122 | 9/2012 |
| WO | WO 89/08114 A1 | 9/1989 |
| WO | WO 92/01049 A2 | 1/1992 |
| WO | WO 94/17184 A1 | 8/1994 |
| WO | WO 96/16990 A1 | 6/1996 |
| WO | WO 98/16245 A1 | 4/1998 |
| WO | WO 98/16254 A1 | 4/1998 |
| WO | WO 98/50435 A1 | 11/1998 |
| WO | WO 99/62526 A2 | 12/1999 |
| WO | WO 00/06194 A2 | 2/2000 |
| WO | WO 00/40265 A1 | 7/2000 |
| WO | WO 2001/060803 A1 | 8/2001 |
| WO | WO 01/97844 A1 | 12/2001 |
| WO | WO 02/06347 A1 | 1/2002 |
| WO | WO 02/32288 A2 | 4/2002 |
| WO | WO 2003/106498 A2 | 12/2003 |
| WO | WO 2004/058288 A1 | 7/2004 |
| WO | WO 2004/078140 A2 | 9/2004 |
| WO | WO 2004/092160 A2 | 10/2004 |
| WO | WO 2005/042019 A1 | 5/2005 |
| WO | WO 2005/044855 A2 | 5/2005 |
| WO | WO 2005/063819 A2 | 7/2005 |
| WO | WO 2005/103083 A2 | 11/2005 |
| WO | WO 2006/088951 A2 | 8/2006 |
| WO | WO 2006/099875 A1 | 9/2006 |
| WO | WO 2006/125640 A2 | 11/2006 |
| WO | WO 2007/042309 A2 | 4/2007 |
| WO | WO 2008/037257 A2 | 4/2008 |
| WO | WO 2008/047242 A2 | 4/2008 |
| WO | WO 2008/073160 A2 | 6/2008 |
| WO | WO 2008/116103 A2 | 9/2008 |
| WO | WO 2008/121615 A2 | 10/2008 |
| WO | WO 2008/150530 A2 | 12/2008 |
| WO | WO 2009/062054 A1 | 5/2009 |
| WO | WO 2009/118142 A1 | 10/2009 |
| WO | WO 2009/128917 | 10/2009 |
| WO | WO 2010/052014 | 5/2010 |
| WO | WO 2010/061357 A1 | 6/2010 |
| WO | WO 2010/061358 A1 | 6/2010 |
| WO | WO 2010/061359 A1 | 6/2010 |
| WO | WO 2010/061360 A1 | 6/2010 |

(56) References Cited

FOREIGN PATENT DOCUMENTS

| | | |
|---|---|---|
| WO | WO 2011/012637 A2 | 2/2011 |
| WO | WO 2011/029892 A2 | 3/2011 |
| WO | WO 2011/109365 A2 | 9/2011 |
| WO | WO 2011/154453 A1 | 12/2011 |
| WO | WO 2012/041800 A1 | 4/2012 |
| WO | WO 2012/076663 A1 | 6/2012 |
| WO | WO 2012/092612 A1 | 7/2012 |
| WO | WO 2012/092616 A1 | 7/2012 |
| WO | WO 2013/059885 A2 | 5/2013 |
| WO | WO 2013/102144 A2 | 7/2013 |
| WO | WO 2013/164837 A1 | 11/2013 |
| WO | WO 2014/048921 A1 | 4/2014 |
| WO | WO 2014/068114 A1 | 5/2014 |
| WO | WO 2014/089416 A1 | 6/2014 |
| WO | WO 2014/142220 A1 | 9/2014 |
| WO | WO 2014/178820 A1 | 11/2014 |
| WO | WO 2015/009726 A2 | 1/2015 |
| WO | WO 2015/066450 A1 | 7/2015 |
| WO | WO 2015/121454 A1 | 8/2015 |
| WO | WO 2015/130728 A1 | 9/2015 |
| WO | WO 2015/130732 A2 | 9/2015 |
| WO | WO 2015/195555 A1 | 12/2015 |
| WO | WO 2015/195556 A1 | 12/2015 |
| WO | WO 2016/040294 A2 | 3/2016 |
| WO | WO 2016/089960 A1 | 6/2016 |
| WO | WO 2016/133903 A2 | 8/2016 |
| WO | WO 2016/187546 A1 | 11/2016 |
| WO | WO 2016/209921 A1 | 12/2016 |
| WO | WO 2016/210223 A1 | 12/2016 |
| WO | WO 2017/004266 A1 | 1/2017 |
| WO | WO 2017/079150 A1 | 5/2017 |
| WO | WO 2018/002181 A1 | 1/2018 |
| WO | WO 2018/213732 A1 | 11/2018 |
| WO | WO 2019/089832 A1 | 5/2019 |
| WO | WO 2019/186273 A1 | 10/2019 |
| WO | WO 2020/243911 | 12/2020 |

OTHER PUBLICATIONS

Agheli, A. et al., "A Rare Case of Primary Amyloidosis, Presenting with Severe Pulmonary Hypertension and Bilateral Pleural Effusion," Blood, vol. 106: p. 5100 (2005).
Almagro, J.C. and Fransson, J., "Humanization of antibodies," Frontiers in Bioscience, vol. 13; 1619-1633 (2008).
Arican, et al., "Philadelphia Chromosome (+) T-Cell Acute Lymphoblastic Leukemia After Renal Transplantation," Transplantation Proceedings, vol. 31; 3242-3243 (1999).
Armitage et al., "Long-Term Remission Durability and Functional Status of Patients Treated for Diffuse Histiocytic Lymphoma with the CHOP Regimen," J. Clin. Oncol. 2:898-902, (1984).
Arthur, "Innovations in subcutaneous infusions," J. Infus. Nurs. 38(3); 179-87; May/Jun. 2015.
Bachireddy, et al., "Haematologic Malignancies: at the Forefront of Immunotherapeutic Innovation," Nature Reviews Cancer, vol. 15, No. 4, pp. 201-215, Apr. 1, 2015 (Apr. 1, 2015).
Bahlis, N.J. et al., "Daratumumab, lenalidomide, and dexamethasone (DRd) vs lenalidomide and dexamethasone (Rd) in relapsed or refractory multiple myeloma (RRMM): Efficacy and safety updated (POLLUX)," Journal of Clinical Oncology, vol. 35; No. 15; 8025; Abstract (2017).
Berglund, L. et al., "The epitope space of the human proteome," Protein Science, vol. 17; 606-613 (2008).
Blankestijn, et al., "Could daratumumab be used to treat severe allergy?," Journal of Allergy and Clinical Immunology, Elsevier, Amsterdam, NL, vol. 139, No. 5, p. 1677-1678, Jan. 19, 2017.
Bose, P. et al., "Treatment of Relapsed/Refractory Acute Myeloid Leukemia," Curr. Treat. Options in Oncol., vol. 18; No. 17; 30 pages (2017).
Brand, F-X. et al., "Prospect for Anti-HER2 Receptor Therapy in Breast Cancer," AntiCancer Research, vol. 26; 463-470 (2006).

Brown, et al., "Tolerance of single, but not multiple, amino acid replacements in antibody VH CDR 2: a means of minimizing B cell wastage from somatic hypermutation?" The Journal of Immunology, 156: 3285-3291 (1996).
Carter et al., "Identification and validation of cell surface antigens for antibody targeting in oncology," Endocrine-Related Cancer, vol. 11, pp. 659-687, (2004).
Chari et al., "Subcutaneous Delivery of Daratumumab in Patients with Relapsed or Refractory Multiple Myeloma (RRMM): PAVO, an Open-label, Multicenter, Dose Escalation Phase 1b Study," American Society of Hematology, Clinical Trials.gov Identifier NCT02519452, Dec. 2017.
Chari A. et al., "Subcutaneous delivery of daratumumab in patients (pts) with relapsed or refractory multiple myeloma (RRMM): PAVO, an openlabel, multicenter, dose escalation phase 1b study," 2017 ASH Annual Meeting *ANZMAP Multiple Myeloma Highlights*, 2017.
Chaulagain, C.P., et al., "How we Treat Systemic Light-Chain Amyloidosis," Clinical Advances in Hematology & Oncology, vol. 13; No. 5; 315-324 (2015).
Chaulagain, C.P. and Comenzo, R.L., "New Insights and Modern Treatment of AL Amyloidosis," Curr Hematol Malig Rep, vol. 8; 291-298 (2013).
Chen, et al., "Selection and Analysis of an Optimized Anti-VEGF Antibody: Crystal Structure of an Affinity-matured Fab in Complex with Antigen," Journal of Molecular Biology, 293: 865-881 (1999).
Cheson et al., "Revised Response Criteria for Malignant Lymphoma," Journal of Clinical Oncology, vol. 25, No. 5, 579-586 (Feb. 10, 2007).
Chiarugi, A. et al., "The NAD metabolome—a key determinant of cancel cell biology," Nature Reviews, vol. 12; 741-752 (2012).
Chillemi, A. et al., "Anti-CD38 Antibody Therapy: Windows of Opportunity Yielded by the Functional Characteristics of the Target Molecule," Molecular Medicine, vol. 19; 99-108 (2013).
Chou, et al., "Drug Combination Studies and their Synergy Quantification Using the Chou-Talalay Method," Cancer Research, 70(2): 440-446 (2010).
Clinicaltrials.gov, "Daratumumab in Combination with ATRA (DARA/ATRA)," Identifier: NCT02751255; First posted: Apr. 26, 2016 (11 pages).
ClinicalTrials.gov "Study of YM155 in Refractory Diffuse Large B-cell Lymphoma (DLBCL) Subjects," Interventional Studies, U.S. National Library of Medicine, //clinicaltrials.gov/ct2/show/record/ NCT00498914, First posted Jul. 11, 2007 [retrieved on Sep. 10, 2018] (14 pages).
ClinicalTrials.gov, "A Study of Daratumumab with the Addition of Recombinant Human Hyaluronidase (rHuPH20) for the Treatment of Participants with Relapsed or Refractory Multiple Myeloma," Identifier: NCT02519452; First Posted: Aug. 11, 2015 (13 pages).
ClinicalTrials.gov, "A Study to Evaluate Subcutaneous Daratumumab in Combination with Standard Multiple Myeloma Treatment Regimens," Identifier: NCT03412565, First Posted: Jan. 26, 2018 (16 pages).
ClinicalTrials.gov, "A Phase 1 Study to Assess the Safety, Tolerability, and Pharmacokinetics of TAK-079 in Healthy Participants," Identifier: NCT02219256, 13 pages; Latest version posted: Mar. 22, 2017. (13 pages).
Colman, "Effects of amino acid sequence changes on antibody-antigen interactions," A Structural View of Immune Recognition by Antibodies, Biomolecular Research Institute, 33-36, (1994).
Comenzo, R.L. et al., "Consensus guidelines for the conduct and reporting of clinical trials in systemic light-chain amyloidosis," Leukemia, vol. 26; 2317-2325 (2012).
Cotner, et al., "Human T Cell Proteins Recognized by Rabbit Heteroantisera and Monoclonal Antibodies," International Journal of Immunopharmaceuticals, 3(3): 255-268 (1981).
Data show daratumumab achieved a pronounced overall response rate as a single-agent with tolerable safety profile in heavily pre-treated multiple myeloma patients, Johnson & Johnson Press release[online] (retrived on Jul. 27, 2020), May 30, 2015, retrieved from the Internet<URL:https://www.jnj.com/media-center/press-releases/Data-show-daratumumab-achieved-a-pronounced-overall-

(56) References Cited

OTHER PUBLICATIONS response-rate-as-a-single-agent-with-tolerable-safety-profile-in-heavily-pre-treated-multiple-myeloma-patients>; 4 pages.
Davies, et al., "Affinity improvement of single antibody VH domains: residues in all three hypervariable regions affect antigen binding," Immunotechnology, 2: 169-179 (1996).
Davis, et al., "Transgenic mice as a source of fully human antibodies for the treatment of cancer," Cancer and Metastasis Reviews, 18: 421-425 (1999).
Deckert, et al., "SAR650984, A Novel Humanized CD38-Targeting Antibody, Demonstrates Potent Antitumor Activity in Models of Multiple Myeloma and Other CD38β Hematologic Malignancies," Clinical Cancer Research. vol. 20, No. 17, pp. 4574-4583 (2014).
Dennis, "Off by a Whisker," Nature, 442 (17): 749-741 (2006).
DePascalis, et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, 169: 3076-3084 (2002).
DeWolf, S. and Tallman, M., "How I Treat Relapsed or Refractory AML," Blood, downloaded from: https://ashpublications.org/blood/article-abstract/doi/10.1182/blood.2019001982/460740/How-I-Treat-Relapsed-or-Refractory-AML?redirectedFrom-PDF; 32 pages (2020).
De Haart, S.J. et al., "Accessory Cells of the Microenvironment Protect Multiple Myeloma from T-Cell Cytotoxicity through Cell Adhesion-Mediated Immune Resistance," Clinical Cancer Research, vol. 19; No. 20; 5591-5601 (2013).
De Weers, et al., "Daratumumab, a Novel Therapeutic Human CD38 Monoclonal Antibody, Induces Killing of Multiple Myeloma and Other Hematological Tumors," The Journal of Immunology, 186: 1840-1848 (Pre-published online Dec. 27, 2010).
De Weers, M. et al., "Humax-CD38, a New Human CD38 Monoclonal Antibody, Effectively Mediates Killing of Multiple Myeloma and Plasma Cell Leukemia Cells," abstract, Submitted for the 16th European Congress of Immunology—ECI2006, Paris, France, [Sep. 6-9, 2006].
De Weers et al., "HuMax-CD38, a new human CD38 monoclonal antibody, effectively mediates killing of multiple myeloma and plasma cell leukemia cells," The 23rd International Conference on 'Advances in the Application of Monoclonal Antibodies in Clinical Oncology, (Jun. 26-28, 2006), Royal Myconian Resort & Thalasso Spa Center, Mykonos, Greece (Abstract).
Dimopoulos, M.A. et al., "Daratumumab, Lenalidomide, and Dexamethasone for Multiple Myeloma," The New England Journal of Medicine, vol. 375; No. 14; 1319-1331 (2016).
Dimopoulos, M.A. et al., "Daratumumab plus lenalidomide and dexamethasone versus lenalidomide and dexamethasone in relapsed or refractory multiple myeloma: updated analysis of POLLUX," Haematologica, vol. 103; No. 12; 2088-2096 (2018).
Dispenzieri, A. et al., "Treatment of Immunoglobulin Light Chain Amyloidosis: Mayo Stratification of Myeloma and Risk-Adapted Therapy (mSMART) Consensus Statement," Mayo Clin Proc., vol. 90; No. 8; 1054-1081 (2015).
DMC recommends termination of study into daratumumab with atezolizumab to treat NSCLC, European Pharmaceutic Manufacturer[online](retrieved on Jul. 26, 2020), May 30, 2018, retrieved from the Internet<URL:https://www.epmmagazine.com/news/dmc-recommends-termination-of-study-into-daratumumab/>; 3 pages.
Dos Santos, et al., Anti-Leukemic Activity of Daratumumab in Acute Myeloid Leukemia Cells and Patient-Derived Xenografts, Blood, vol. 124, Abstract 2312, (2014).
Doshi, et al., "Daratumumab Treatment in Combination with Chop or R-Chop Results in the Inhibition or Regression of Tumors in Preclinical Models of Non-Hodgkins Lymphoma," Haematologica, The Hematology Journal, 99(1): 138 (2014).
Eldfors, et al., "Landscape of Mutations in Relapsed Acute Myeloid Leukemia," vol. 124: No. 21, p. 2367; (2014).

Ellis, et al., "Engineered Anti-CD38 Monoclonal Antibodies for Immunotherapy of Multiple Myeloma," The Journal of Immunology, 155: 925-937 (1995).
Engert, et al., "A Phase-I Study of an Anti-CD25 Ricin A-Chain Immunotoxin (RFT5-SMPT-dgA) in Patients with Refractory Hodgkin's Lymphoma," Blood, 89(2): 403-410 (1997).
Ettinger, R. et al., "Pathogenic mechanisms of IgE-mediated inflammation in self- destructive autoimmune responses," Autoimmunity, vol. 50; No. 1; 25-36 (2017).
Ferrero, et al., Characterization and phylogenetic epitope mapping of CD38 ADPR cyclase in the cynomolgus macaque, BMC Immunology, 5(21): 1-13 (2004).
Field-Smith, "Bortezomid (Velcade™) in the treatment of multiple myeloma," Therapeutic and Clinical Risk Management, 2(3): 271-279 (2006).
Flavell, et al., "Therapy of human T-cell acute lymphoblastic leukaemia with a combination of anti-CD7 and anti-CD38-SAPORIN immunotoxins is significantly better than therapy with each individual immunotoxin," Br. J. Cancer, vol. 84, No. 4, pp. 571-578, (2001).
Franco, et al., "The transmembrane glycoprotein CD38 is a catalytically active transporter responsible for generation and influx of the second messenger cyclic ADP-ribose across membranes," FASEB Journal, 12: 1507-1520 (1998).
Fujimori, et al., "A Modeling Analysis of Monoclonal Antibody Percolation Though Tumors: A Binding-Site Barrier," Journal of Nucleic Medicine, 31: 1191-1198 (1990).
Fujioka, Y. and Kurokawa, M., "Follicular lymphoma presenting with massive splenomegaly," International J Hematol, vol. 95; 3-4 (2012).
Funaro et al., "CD38 Functions Are Regulated Through an Internalization Step," Journal of Immunology, 160: 2238-2247 (1998).
Funaro, et al., "Human CD38: a versatile leukocyte molecule with emerging clinical prospectives," Fundamental and Clinical Immunology, 3(3): 101-113 (1995).
Funaro, et al., "Identification and characterization of an active soluble form of human CD38 in normal and pathological fluids," International Immunology, 8(11): 1643-1650 (1996).
Funaro, et al., "Involvement of the Multilineage CD38 Molecule in a Unique Pathway of Cell Activation and Proliferation," The Journal of Immunology, 145: 2390-2396 (1990).
Gallo, et al., "The human immunoglobulin loci introduced into mice: V(D) and J gene segment usage similar to that of adult humans," European Journal of Immunology, 30: 534-540 (2000).
Genmab "Humanx-CD38 Effective in Preclinical Studies," Genmab A/S, Stock Exchange Release 57/2005.
Genmab "Daratumumab Receives Breakthrough Therapy Designation from US Food and Drug Administration", Copenhagen, Denmark; May 1, 2013—Genmab A/S (OMX: GEN) disponible en: http://files.shareholder.com/downloads/AMDA-KPIBN/0x0x659093/64b187b8-830c-4252-acd6-8019b4199069/18%20Daratumumab%20breakthrough%20status_010513_uk.pdf, (May 1, 2013).
Genmab Announces Daratumumab and Ofatumumab Data to Be Presented at American Society of Hematology Annual Meeting (ASH), American Society of Hematology Annual Meeting and Exposition, San Francisco, California, Media Release 06; pp. 1-3 (Nov. 2014).
George, et al., "Differential Effects of Anti-β2-Glycoprotein I Antibodies on Endothelial Cells and on the Manifestations of Experimental Antiphospholipid Syndrome," Circulation, 97: 900-906 (1998).
Goldmacher, et al., "Anti-CD38-Blocked Ricin: An immunotoxin for the Treatment of Multiple Myeloma," The American Society of Hematology, 84(9): 3017-3025 (1994).
Goodwin, "Subcutaneous Daratumumab Potential Game Changer for Multiple Myeloma," Oncology Times, 2017 American Society of Hematology Annual Meeting, p. 49, (2017).
Gopalakrishnan, et al. "Daratumumab improves the anti-myeloma effect of newly emerging multidrug therapies," Blood and Lymphatic Cancer: Targets and Therapy, 3: 19-24 (2013).
Graeff, et al., "Enzymatic Synthesis and Characterizations of Cyclic GDp-ribose," The Journal of Biological Chemistry, 269(48): 30260-30267 (1994).

(56) References Cited

OTHER PUBLICATIONS

Green, "Antibody engineering via genetic engineering of the mouse: XenoMouse strains are a vehicle for the facile generation of therapeutic human monoclonal antibodies," Journal of Immunological Methods, 231: 11-23 (1999).
Green, et al., "Antigen-specific human monoclonal antibodies from mice engineered with hyman Ig heavy and light chain YACs," Nature Genetics, 7: 13-21 (1994).
Gupta, R. et al., "The Economic Impact of Childhood Food Allergy in the United States," JAMA Pediatrics, vol. 167; No. 11; 1026-1031 (2013).
Guse et al., "Regulation of calcium signaling in T lymphocytes by the second messenger cyclic ADP-ribose," Nature 398:70-73, (1999).
Haart, et al., "Sepantronium bromide (YM155) improves daratumumab-mediated cellular lysis of multiple myeloma cells by abrogation of bone marrow stromal cell-induced resistance," Haematologica, Letters to the Editor, vol. 101, No. 8, pp. e339-e343, (2016).
Hara-Yokoyama, "Alteration of enzymatic properties of cell-surface antigen CD38 by agonistic anti-CD38 antibodies that prolong B cell survival and induce activation," International Immunopharmacology, 8: 59-70 (2008).
Hartmann, Radioimmunotherapy of Nude Mice Bearing a Human Interleukin 2 Receptor α-expressing Lymphoma Utilizing the α-emitting Radionuclide-conjugated Monoclonal Antibody 212Bi-anti-Tac, Cancer Research, 54: 4362-4370 (1994).
Henry, et al., "the use of basiliximab in solid organ transplantation," Expert Opinion Pharmacotherapy, 3(10): 1657-1663 (2002).
Holgate, S.T., "New strategies with anti-IgE in allergic diseases," World Allergy Organization Journal, vol. 7; No. 17; 6 pages (2014).
Holm, et al., "Functional mapping and single chain construction of the anti-cytokeratin 8 monoclonal antibody TS1," Molecular Immunology, 44: 1075-1084 (2017).
Hoshino, et al., "Mapping of the Catalylic and Epitopic Sites of Human CD38/NAD+ Glycohydrolase to a Functional Domain in the Carboxyl Terminus1," The Journal of Immunology, 158: 741-747 (1997).
Howard, et al., "Formation and Hydrolysis of Cyclic ADP-Ribose Catalyzed by lymphocyte Antigen CD38," Science, 262(5136): 1056-1059 (1993).
Hu, Y., et al., "Immunophenotypic analysis of abnormal plasma cell clones in bone marrow of primary systemic light chain amyloidosis patients," Chin Med J., vol. 127; No. 15; 2765-2770; Abstract only (2014).
Hu, Y. et al., "The Significance of Abnormal Plasma Cell Clone in Bone Marrow of Primary Systemic Light Chain Amyloidosis Patients," Blood, vol. 122; p. 5342 (2013).
Ikehata, et al., "Autoantibodies against CD38 (ADP-ribosyl Cyclase/Cyclic ADP-ribose Hydrolase) that Impair Glucose-induced Insulin Secretion in Noninsulin-dependent Diabetes Patients," Journal of Clinical Investigations, 102(2): 395-401 (1998).
Inaba, H. et al., "Acute lymphoblastic leukaemia," Lancet, vol. 381; 27 pages (2013).
Jackisch, et al., "Subcutaneous versus intravenous formulation of trastuzumab for HER2—positive early breast cancer: updated results from the phase III HannaH study," Annals of Oncology, vol. 26, pp. 320-325, (2015).
Jackson, et al., "Isolation of a cDNA Encoding The Human CD38 (T10) molecule, A Cell Surface Glycoprotein With An Unusual Discontinuous Pattern of Expression During Lymphocyte Differentiation," The Journal of Immunology, 144(7): 2811-2815 (1990).
Jagannath, et al. Treatment (tx) journeys in newly diagnosed multiple myeloma (NDMM) patients (pts): Results from the Connect MM Registry. Multiple Myeloma Update from the American Society of Clinical Oncology. (ASCO) 41$^{st}$ Annual meeting, (Jun. 4, 2018).
Jakob, et al., "Stage-dependent Expression of CD7, CD45RO, CD45RA and CD25 on CD4-positive Peripheral Blood T-lymphocytes in Cutaneous T-cell Lymphoma," Acta Derm Venerology, 76: 34-36 (1996).
Jakobovits, "the long-awaited magic bullets: therapeutic human monoclonal antibodies from transgenic mice", Expert Opinion on Investigational Drugs, 7(4): 607-614 (1998).
Jang, et al., "The structural basis for DNA binding by an anti-DNA autoantibody," Molecular Immunology, 35: 1207-1217 (1998).
Johnson, et al., "Primary plasma cell leukemia: morphologic, immunophenotypic , and cytogenetic features of 4 cases treated with chemotherapy and stem cell transplantation," Annals of Diagnostic Pathology, 10: 263-268 (2006).
Johnson & Johnson, Janssen to Demonstrate Breadth of Oncology Portfolio with 42 Clinical Data Presentation at the 2014 American Society of Hematology (ASH) Annual Meeting, San Francisco, California (Nov. 2014).
Jones, et al., "Depletion of CD25+ regulatory calls results in suppression of melanoma growth and induction of autoreactivity in mice," Cancer Immunity, 2: 1 (2002). Abstract.
Jones, et al., "Replacing the complementarity-determining regions in a human antibody with those from a mouse," Nature, 321: 522-525 (1986).
Kaufman, G.P. et al., "Daratumumab yields rapid and deep hematologic responses in patients with heavily pretreated AL amyloidosis," Blood, vol. 130; No. 7; 900-902 (2017).
Kita et al., "Antitumor effects of YM155, a novel suppressant, against human aggressive non-Hodgkin Lymphoma," Leukemia Research, vol. 35, pp. 787-792, (2011).
Kita, A., et al., "Sepantronium Bromide (YM155) Enhances Response of Human B-Cell Non-Hodgkin Lymphoma to Rituximab," The Journal of Pharmacology and Experimental Therapeutics, vol. 343; No. 1; 178-183 (2012).
Konapleva, et al., "Ligation of Cell Surface CD38 Protein with Agonistic Monoclonal Antibody Induced a Cell Growth Signal in Myeloid Leukemia Cells," The Journal of Immunology, 161: 4702-4708 (1998).
Kong, S.Y., et al., "Daratumumab Directly Induces Human Multiple Myeloma Cell Death and Acts Synergistically with Conventional and Novel Anti-Myeloma Drugs," Blood, vol. 116; Abstract 3013 (2010).
Konopleva, et al., "CD38 in Hematopoietic Malignancies," Chemical Immunol. Basel Karger, 75: 189-206 (2000).
Kreitman, et al., Phase I Trial of Recombinant Immunotoxin Anti-Tac (Fv)-PE38 (LMB-2) in Patients with Hematologic Malignancies, Journal of Clinical Oncology, 18: 1622-1636 (2000).
Krejcik, J. et al., "Daratumumab depletes CD38+ immune regulatory cells, promotes T-cell expansion, and skews T-cell repertoire in multiple myeloma," Blood, vol. 128; No. 3; 384-394 (2016).
Krejcik, J. et al., Immunomodulatory Effects and Adaptive Immune Response to Daratumumab in Multiple Myeloma,: Blood, vol. 126; 3037; 7 pages (2015).
Kreuger, et al., "Successful in vivo blockade of CD25 (high-affinity interleukin 2 receptor) on T cells by administration of humanized anti-Tac antibody to patients with psoriasis," Journal of American Academy of Dermatology, 41(3): 448-458 (2000).
Kropff, et al., "Bortezomib in combination with dexamethoasone for relapsed multiple myeloma," Leukemia Research, 29: 587-590 (2005).
Kumar, S. et al., "Expression of CD52 on plasma cells in plasma cell proliferative disorders," Blood, vol. 102; No. 3; 1075-1077 (2003).
Kupiec-Weglinski, "CD25-Targeted Therapy Revisited," Transplantation, 69(3): 328-330 (2000).
Lakshman, A. et al., "Efficacy of daratumumab-based therapies in patients with relapsed, refractory multiple myeloma treated outside of clinical trials," Am J. Hematol., vol. 92; 1146-1155 (2017).
Lande, et al., "CD38 ligation plays a direct role in the induction of IL-1β, I-6, and IL-10 secretion in resting human monocytes," Cellular Immunology, 220: 30-38 (2002).
Laubach, J.P., "Daratumumab granted breakthrough drug status," Expert Opinion Investig. Drugs, vol. 23; No. 4; 445-452 (2014).
Laurie, et al., "The role of CD4+CD25+ immunoregulatory T cells in the induction of autoimmune gastritis," Immunology and Cell Biology, 80: 567-573 (2002).
Lazar, et al., "Transforming Growth Factor a: Mutation of Aspartic Acid 47 and Leucine 48 Results in Different Biological Activities," Molecular and Cellular Biology, 8(3): 1247-1252 (1988).

(56) References Cited

OTHER PUBLICATIONS

Leonard, et al., "Molecular cloning and expression of cDNAs for the human interleukin-2 receptor," Nature 311(18): 626-631 (1984).
Lepenies, B. and Jacobs, T., "The Role of Negative Costimulators During Parasitic Infections," Endocrine, Metabolic & Immune Disorders—Drug Targets, vol. 8; 279-288 (2008).
Leveque "Subcutaneous Administration of Anticancer Agents" Anticancer Research, Departments of Pharmacy, University Hospital, Strasbourg, France, vol. 34, pp. 1579-1586 (2014).
Li, et al., "Creation of Patient Derived AML Xenografts Displaying Distinct Phenotypes and Genotypes," Blood, vol. 122: No. 21, p. 5018 (2013).
Lin, et al., "Structure-Function Relationships in Glucagon: Properties of Highly Purified Des-His1-, Monoiodi-, and [Des-Asn28, Thr29](homoserine lactone27)-glucagon," Biochemistry, 14(9): 1559-1563 (1975).
Lippincott-Schwartz, "Antibodies as cell Biological Tools," Current Protocols in Cell Biology, 16.0.1-16.0.2, (2002).
Liu et al., "Induction of Chemoresistance by All-Trans Retinoic Acid via a Noncanonical Signaling in Multiple Myeloma Cells," PLOS One, vol. 9, No. 1, page Article No. e85571, Jan. 2014.
Lonberg, et al., "Antigen-specific human antibodies from mice comprising four distinct genetic modifications," Nature: 308: 856-859 (1994).
Lu et al., "Issues Related to Targeted Delivery of Proteins & Peptides," The AAPS Journal, vol. 8, No. 3, Article 55, pp. E466-E478, Jul. 21, 2006.
MacCallum, et al., "Antibody-antigen Interactions: Contact Analysis and Binding Site Topography," Journal of Molecular Biology, 262, 732-745 (1998).
Machida, H. et al., "Aggressive plasma cell leukemia with cleaved, multilobated and monocytoid nuclei," International Journal of Hematol., vol. 73; Suppl 1; 158; Abstract No. 411 (2001).
Mai, E. et al., "Phase III trial of bortezomib, cyclophosphamide and dexamethasone (VCD) versus bortezomib, doxorubicin and dexamethasone (Pad) in newly diagnosed myeloma," Leukemia, vol. 29; 1721-1729 (2015).
Malavasi, et al., "Human CD38: a glycoprotein in search of a function," Immunology Today, 15(3): 95-97 (1994).
Maloney, et al., "Antibody Therapy for Treatment of Multiple Myeloma," Semin Hematol. 36 (Suppl. 3): 30-33 (1999).
Manier, S. et al., "Bone Marrow Microenvironment in Multiple Myeloma Progession," Journal of Biomedicine and Biotechnology, vol. 2012; 5 pages (2012).
Matas-Cespedes, A. et al., "The human CD38 monoclonal antibody daratumumab shows anti-tumor activity and hampers leukemia-microenvironment interactions in chronic lympocytic leukemia," Clinical Cancer Research, vol. 23; No. 6; 1493-1505 (2017).
Mauri, C. and Menon, M., "The expanding family of regulatory B cells," International Immunology, vol. 27; No. 10; 479-486 (2015).
McCarthy, P.L., "Strategies for induction, autologous hematopoietic stem cell transplantation, consolidation, and maintenance for transplantation-eligible multiple myeloma patients", Hematology, vol. 2013, NI. 1, pp. 496-503 (Dec. 2013).
McKelvey, et al., "Hydroxyldaunomycian (Adriamycin) Combination Chemotherapy in Malignant Lymphoma," Cancer, vol. 38, No. 4, pp. 1485-1493 (Oct. 1976).
Merlini, G. and Bellotti, V., "Molecular Mechanisms of Amyloidosis," The New England Journal of Medicine, vol. 349; No. 6; 583-596 (2003).
Mills, et al., Characterization of Monoclonal Antibodies that Inhibit CD38 Adp-ribosyl Cyclase Activity, LSSURP HLB Program, Department of Pharmacology, University of Minnesota, 2007.
Mills, E.N.C. et al., "The prevalence, cost and basis of food allergy across Europe," Allergy, vol. 62; 717-722 (2007).
Mikhael et al., "Cyclophosphamide-Bortezomib-Dexamethasone (CYBORD) Produces Rapid and Complete Hematological Response in Patients with AL Amyloidosis," Blood 119:4391-94 (Year: 2012).
Mohammad et al., "The Addition of Bryostatin 1 to Cyclophosphamide, Doxorubicin, Vincristine, and Prednisone (CHOP) Chemotherapy Improves Response in a CHOP-resistant Human Diffuse Large Cell Lymphoma Xenograft Model," Clinical Cancer Research, vol. 6, 4950-4956 (Dec. 2000).
Morrison, et al., "Chimeric human antibody molecules: Mouse antigen-binding domains with human constant region domains," Proceedings of the National Academy of Science USA, vol. 81; 6851-6855 (1984).
Mrowietz, "Treatment of Severe Psoriasis with Anti-CD25 Monoclonal Antibodies," Arch. Dermatology, 136: 675-676 (2000).
Mukherjee, et al., "Production and Characterization of Protective Human Antibodies against Shiga Toxin 1," Infection and Immunity, 70(10): 5896-5899 (2012).
Muyldermans, "Single domain camel antibodies: current status," Reviews in molecular Biotechnology, 74: 277-302 (2001).
Muyldermans, et al., "Recognition of antigens by single-domain antibody fragments: the superfluous luxury of paired domains," Trends in Biochemical Sciences, 26(4): 230-235 (2001).
Najjar et al., "Abstract P227: Accumulation of MDSC Subsets in Renal Cell Carcinoma Correlates with Grade and Progression Free Survival, and is Associated with Intratumoral Expression of IL-1β, IL-8 and CXCL5," Journal for Immunotherapy of Cancer, Nov. 6, 2014, vol. 2, p. 110-112.
Nijhof, I.S. et al., Preclinical Evidence for the Therapeutic Potential of CD38-Targeted Immuno-Chemotherapy in Multiple Myeloma Patients Refractory to Lenalidomide and Bortezomib. Clin Cancer Res., vol. 21, No. 12, pp. 2802-2810 (2014).
Nijhof, et al.,"Modulation of CD 38 Expression Levels on Multiple Myeloma Tumor Cells By All-Trans Retinoic Acid Improves the Efficacy of the Anti-CD 38 Monoclonal Antibody Daratumumab," Blood, American Society of Hematology, US, vol. 124, No. 21, p. 2096, Dec. 6, 2014. (Abstract Only).
Nijhof, I.S. et al., Combination of the anti-CD38 monoclonal antibody daratumumab and all-trans retinoic acid (Abstract in Proceedings of the AACR Special Conference on Hematologic Malignancies: Translating Discoveries to Novel Therapies). Clin Cancer Res, Sep. 20, 2014, vol. 21, No. 17 Suppl, pages Abstract A12; Abstract.
Nijhof I.S. et al.: "Upregulation of CD38 expression on multiple myeloma cells by all-trans retinoic acid improves the efficacy of daratumumab", Leukemia, vol. 29, No. 10, ISSN 1476-5551, pp. 2039-2049 (2015).
Nikaido, et al., "Molecular cloning of cDNA encoding human interleukin-2 receptor," Nature, 311: 631-635 (1984).
Offidani et al., "An evidence-based review of ixazomib citrate and its potential in the treatment of newly diagnosed multiple myeloma," OncoTargets and Therapy, vol. 7, pp. 1793-1800, 2014.
Onizuka, et al., "Tumor Rejection by in Vivo Administration of Anti-CD25 (Interleukin-2 Receptor α Monoclonal Antibody," Cancer Research, 59: 3128-3133 (1999).
Orlowski, "The Ubiquitin Proteasome pathway from Bench to Bedside," American Society of Hematology, 220-225 (2005).
Ostberg, et al., "Human and humanized monoclonal antibodies: preclinical studies and clinical experience," Biochemical Society Transactions, 23: 1-6 (1995).
Padlan, et al., "Identification of specificity-determining resides in antibodies," FASEB Journal, 9: 135-139 (1995).
Palumbo, A. et al., "Daratumumab, Bortezomib, and Dexamethasone for Multiple Myeloma," The New England Journal of Medicine, vol. 375; No. 8; 754-766 (2016).
Palumbo, A. et al., "Daratumumab, Bortezomib, and Dexamethasone for Multiple Myeloma," The New England Journal of Medicine, vol. 375; No. 8; 754-766; Suppl. Material: the protocol; total pp. 119 (2016).
Park, S. et al., "Successful Treatment by Rituximab of an Ebv-Related Lymphoma after Autologous Transplantation for Angioimmunoblastic T-Cell Lymphoma," International Journal of Hematol., vol. 76; Suppl. 1; 118; Abstract No. P340 (2002).
Parren et al., "HuMax-CD38, a new human CD38 monoclonal antibody, effectively mediates killing of multiple myeloma and plasma cell leukemia cells," American Society of Hematology 47th annual meeting, Atlanta, Georgia, USA, Dec. 10-13, 2005 (Abstract).
Parren, et al., HuMax-CD38, Myconos, Jun. 26, 2006.
Parren, et al., HuMax-CD38, Torino, Jun. 8-10, 2006.

(56) References Cited

OTHER PUBLICATIONS

Pascual, et al., "Anti-interleukin-2 receptor antibodies: basiliximab and daclizumab," Nephrology Dial. Transplant, 16: 1756-1760 (2001).

Patel, J.P., "Prognostic Relevance of Integrated Genetic Profiling in Acute Myeloid Leukemia," The New England Journal of Medicine, vol. 366; No. 12; 1079-1089 (2012).

Patton, D.T. et al., "The P13K p110δ Regulates Expression of CD38 on Regulatory T Cells," PLOS one, vol. 6; No. 3; e17359; 8 pages (2011).

Paul, M.D., "Fundamental Immunology," Chapter 9, Raven Press, New York, $3^{rd}$ ed., 292-295 (1993).

Peipp, et al., "Fully Human CD38 Antibodies Efficiently Trigger ADCC and CDC of Multiple Myeloma Cell Lines and Primary Tumor Cells (Poster)," Blood, vol. 106(11): 944A, $47^{th}$ Annual Meeting of the American Society of Hematology, 2005; published (Nov. 16, 2005).

Peipp, et al., Fully Human CD38 Antibodies Efficiently Trigger ADCC and CDC of Multiple Myeloma and Plasma Cell Leukemia Cells (Poster 2) Conference proceedings, poster presentation at the 2005 Annual Meeting of the American Society of Hematology, (Dec. 12, 2005).

Peipp, et al., $47^{th}$ Annual Meeting of the American Society of Hematology, Atlanta, GA, Dec. 10-13 (2005). (Meeting Abstract).

Peng, et al., "Oncolytic measles viruses displaying a single-chain antibody against CD38, a myeloma cell marker," Blood, 101, 2557-2562 (2003).

Phase 1/2 Dose Escalation and Efficacy Study of Anti-CD38 Monoclonal Antibody in Patients With Selected CD38+ Hematological Malignancies, First posted Mar. 10, 2010, ClinicalTrials.gov. identifier No. NCT01084252.

Prosniak, M. et al.: "Development of a Cocktail of Recombinant-Expressed Human Rabies Virus-Neutralizing Monoclonal Antibodies for Postexposure Prophylaxis of Rabies," The Journal of Infectious Diseases, vol. 187; 53-56 (2003).

Rai, S. et al., "Successful Allogeneic Hematopoietic Stem Cell Transplantation in a Young Patient with Richter Syndrome Presenting with Chronic Lymphocytic Leukemia and Diffuse Large B-Cell Lymphoma with Different Cell Origins," Intern Med, vol. 52; 273-276 (2013).

Richardson, et al., "Daratumumab," Drugs of the Future, 38(8): 545-554 (2013).

Rituxan Hycela Label, "Highlights of prescribing information. Rituxan Hycela™ (rituximab and hyaluronidase human) injection, for subcutaneous use," 32 pages (Jun. 2017).

Sachchithanantham, S. et al., "Use of Plasma Cell Immunophenotype as Prognostic Markers in Patients with Systemic AL Amyloidosis," Blood, vol. 122; p. 3120 (2013).

Sagaster, V. et al., "Bortezomib in relapsed multiple myeloma: response rates and duration of response are independent of a chromosome 13q-deletion," Leukemia, vol. 21; 164-168 (2007).

Saito, M. et al., "A Case of Retroperitoneal Extramedullary Plasmacytoma," Acta Urol. Jpn., vol. 49; 735-739 (2003).

Salar et al., "Comparison of Subcutaneous Versus Intravenous Administration of Rituximab As Maintenance Treatment for Follicular Lymphoma: Results From a Two-Stage, Phase IB Study," Journal of Clinical Oncology, vol. 32, No. 17, pp. 1782-1791, (Jul. 10, 2014).

Sanchez-Gonzalez et al., "Rituximab subcutaneous in B-Cell non-Hodgkin lymphoma: clinical experience in a single center," Leukemia & Lymphoma, vol. 59, No. 4, pp. 1019-1021 (2018).

San-Miguel, J. et al., "Efficacy by cytogenetic risk status for daratumumab in combination with lenalidomide and dexamethasone or bortezomib and dexamethasone in relapsed or refractory multiple myeloma," EHA22; EHA Learning Center; Abstract; 4 pages (2017).

San-Miguel, J., "New approaches to myeloma treatment in 2017," EHA Learning Center; Abstract; 4 pages (2017).

Schonland, S., et al., "Detection and Charaterization of Plasma Cell and B Cell Clones in Patients with Systemic Light Chain Amyloidosis Using Flow Cytometry," Blood, vol. 142, p. 2068 (2014).

Sher, T. et al., "First report of safety and efficacy of daratumumab in 2 cases of advanced immunoglobulin light chain amyloidosis," Blood, vol. 128; No. 15; 1987-1989 (2016).

Shields, et al., "High Resolution mapping of the binding site on human IgG1 for FcγRi, FcγRII, FcγRIII, and FcRn and design of IgG1 variants with improved binding to the FcγR," J. Biol. Chem., vol. 276, No. 9, pp. 6591-6604, (2001).

Shpilberg, et al., "Subcutaneous administration of rituximab (MabThera) and trastuzumab (Herceptin) using hyaluronidase," British Journal of Cancer, vol. 109, pp. 1556-1561, 2013.

Shubinsky, et al., "The CD38 Lymphocyte Differentiation Marker: New Insight into Its Ectoenzymatic Activity and Its Role as a Signal Transducer," Immunity, 7: 315-324 (1997).

Sicherer, S.H. and Sampson, H.A., "Food allergy: Epidemiology, pathogenesis, diagnosis, and treatment," J. Allergy Clin Inmmunol, vol. 133; 291-307 (2014).

Skeel, Handbook of Cancer Gliemotherapy, $3^{rd}$ edition, Little, Brown & Co., pp. 330-350 (1991).

Smithson, G. et al., "TAK-079 is a high affinity monoclonal antibody that effectively mediates CD38+ cell depletion," Journal of Immunol., vol. 198; Suppl. 1; 224.20; Abstract (2017).

Sonneveld, P. and Annemiek Broijl, "Treatment of Relapsed and Refractory Multiple Myeloma," Review Article, Leaders in Hematology, review series, Haematologica, 101(4):396-406 (2016).

Spencer, A. et al., "Daratumumab plus bortezomib and dexamethasone versus bortezomib and dexamethasone in relapsed or refractory multiple myeloma: updated analysis of CASTOR," Haematologica, vol. 103; No. 12; 2079-2087 (2018).

Strome, S.E. et al., "A Mechanistic Perspective of Monoclonal Antibodies in Cancer Therapy Beyond Target-Related Effects," The Oncologist, vol. 12; 1084-1095 (2007).

Swaika, A. et al., "Current state of anti-PD-L1 and anti-PD-1 agents in cancer therapy," Molecular Immunology, vol. 67; 4-17 (2015).

Tabernero, et al., "Adult precursor B-ALL with BCR/ABL gene rearrangements displays a unique 21mmunophenotyped based on the pattern of CD10, CD34, CD13, and CD38 expression," Leukemia, vol. 15, No. 3, pp. 406-414, (2001).

Talmadge, J.E. and Gabrilovich, D.I, "History of myeloid-derived suppressor cells," Nature Reviews, vol. 13; 739-752 (2013).

Terhorst, et al., "Biochemical Studies of the Human Thymocyte Cell-Surface Antigens T6, T9 and T10," Cell, 23: 771-780 (1981).

The Cancer Genome Atlas Research Network et al., "Genomic and Epigenomic Landscapes of Adult De Novo Acute Myeloid Leukemia," N. Engl. J. Med, vol. 368; No. 22; 2059-2074 (2013).

Topalian, S.L., et al., "Immune Checkpoint Blockade: A Common Denominator Approach to Cancer Therapy," Cancer Cell, vol. 27; 450-461 (2015).

Tzartos, S.J., et al., "Epitope Mapping by Antibody Competition," Methods in Molecular Biology, vol. 66; 55-66 (1996).

Usmani, et al., "Clinical efficacy of daratumumab monotherapy in patients with heavily pretreated relapsed or refractory multiple myeloma," Blood, vol. 128, No. 1, pp. 37-44, (May 23, 2016).

Usmani, S.Z. et al., "Efficacy of Daratumumab, Lenalidomide, and Dexamethasone Versus Lenalidomide and Dexamethasone in Relapsed or Refractory Multiple Myeloma Patients with 1 to 3 Prior Lines of Therapy: Updated Analysis of Pollux," Blood, vol. 128; No. 22; 1151; 10 pages (2016).

Usmani, S.Z. et al., "Open-Label, Multicenter, Dose Escalation Phase 1b Study to Assess the Subcutaneous Delivery of Daratumumab in Patients (pts) with Relapsed or Refractory Multiple Myeloma," Blood, vol. 128; No. 22; 1149 (2016).

Usmani, S.Z. et al., "Subcutaneous delivery of daratumumab in relapsed or refractory multiple myeloma," Blood, vol. 134; No. 8; 668-677 (2019).

Vadjos, et al., "Comprehensive Functional Maps of the Antigen-binding Site of an Anti-ErbB2 Antibody Obtained with Shotgun Scanning Mutagenesis," Journal of Molecular Biology, 320: 415-428 (2002).

Van Bueren, et al., "Direct In Vitro Comparison of Daratumumab With Surrogate Analogs of Anti-CD38 Antibodies," New Evidence Oncology Issue, Apr. 2015 [retrieved on Feb. 3, 2016] Retrieved

(56) References Cited

OTHER PUBLICATIONS from the Internet: URL: Http:///www.newevidence.com/oncology/direct-in-vitro-comparison-of-daratumumab-with-surrogate-analogs-of-anti-cd38-antibodies>.
Van de Donk et al., "Monoclonal antibodies targeting CD38 in hematological malignancies and beyond," Immunological Reviews, vol. 270, pp. 95-112, (2016).
Venner et al., "Cyclophosphamide, bortezomib, and dexamethasone therapy in AL amyloidosis is associated with high clonal response rates and prolonged progression-free survival," Blood, vol. 119, No. 9, pp. 4387-4390, (2012).
Vorre, et al., "Multiple Daratumumab Abstracts to be Presented at EHA," ArrayDiagnostica, Abstract Only (2014).
Wagner, V., et al., "Preclinical Efficacy of Sepantronium Bromide (YM155) in multiple myeloma is conferred by down regulation of Mcl-1," Oncotarget, 5(21): 10237-10250 (2014).
Wagner et al., Survivin in Multiple Myeloma: Prognostic and Therapeutic Implications, vol. 118, Article 137, 2011 (Abstract Only).
Wang, L. et al., "VISTA, a novel mouse Ig superfamily ligand that negatively regulates T cell responses," J. Exp. Med., vol. 208; No. 3; 577-592 (2011).
WCJ van de Donk, "A Phase 1 and Phase 2 Study of Daratumumab in Combination With All-Trans Retinoic Acid in Relapsed/Refractory Multiple Myeloma," Clinical Trials.gov Identification No. NCT02751255; (First posted Apr. 26, 2016).
Wei, W. et al., "Roles and mechanisms of the CD38/cyclic adenosine diphosphate ribose/Ca2+ signaling pathway," World Journal of Biological Chemistry, vol. 5; No. 1; 58-67 (2014).
Weisel, K.C. et al., "Efficacy of daratumumab in combination with lenalidomide plus dexamethasone (DRd) or bortezomib plus dexamethasone (RVd) in relapsed or refractory multiple myeloma (RRMM) based on cytogenetic risk status," Journal of Clinical Oncology, vol. 35; No. 15; 8006; Abstract (2017).
Williams, B.A. et al., "Antibody Therapies for Acute Myeloid Leukemia: Unconjugated, Toxin-Conjugated, Radio-Conjugated and Multivalent Formats," Journal of Clinical Medicine, vol. 8; No. 1261; 31 pages (2019).
Ye et al, "Abstract P240: Treg Increases HepG2 Cell Growth by RANK-RANKL pathway." Journal for Immunotherapy of Cancer, vol. 2; Suppl 3; P240 (Nov. 6, 2014).
International Preliminary Report on Patentability issued May 8, 2018 for International Application No. PCT/US2016/59893, entitled "Subcutaneous Formulations of Anti-CD38 Antibodies and Their Uses".
International Search Report and Written Opinion mailed Jan. 24, 2017 for International Application No. PCT/US2016/59893, entitled "Subcutaneous Formulations of Anti-CD38 Antibodies and Their Uses".
International Preliminary Report on Patentability issued Dec. 26, 2017 for International Application No. PCT/US2016/038702, entitled "Combination Therapies for Heme Malignancies With Anti-CD38 Antibodies and Survivin Inhibitors".
International Search Report and Written Opinion mailed Nov. 29, 2016 for International Application No. PCT/US2016/038702, entitled "Combination Therapies for Heme Malignancies With Anti-CD38 Antibodies and Survivin Inhibitors".
International Preliminary Report on Patentability issued Mar. 14, 2017 for International Application No. PCT/US2015/048899, entitled "Combination Therapies With Anti-CD38 Antibodies".
International Search Report and Written Opinion mailed Apr. 8, 2016 for International Application No. PCT/US2015/048899, entitled "Combination Therapies With Anti-CD38 Antibodies".
International Preliminary Report on Patentability issued Nov. 21, 2017 for International Application No. PCT/US2016/033544, entitled "Anti-CD38 Antibodies for Treatment of Light Chain Amyloidosis and Other CD38-Positive Hematological Malignancies".
International Search Report and Written Opinion mailed Oct. 24, 2016 for International Application No. PCT/US2016/033544, entitled "Anti-CD38 Antibodies for Treatment of Light Chain Amyloidosis and Other CD38-Positive Hematological Malignancies".
International Preliminary Report on Patentability issued Jun. 6, 2016 for International Application No. PCT/US2015/063371, entitled "Anti-CD38 Antibodies for Treatment of Acute Myeloid Leukemia".
International Search Report and Written Opinion mailed Feb. 19, 2016 for International Application No. PCT/US2015/063371, entitled "Anti-CD38 Antibodies for Treatment of Acute Myeloid Leukemia".
International Preliminary Report on Patentability issued Dec. 26, 2017 for International Application No. PCT/US2016/039165, entitled "Immune Modulation and Treatment of Solid Tumors With Antibodies That Specifically Bind CD38".
International Search Report and Written Opinion mailed Oct. 14, 2016 for International Application No. PCT/US2016/039165, entitled "Immune Modulation and Treatment of Solid Tumors With Antibodies That Specifically Bind CD38".
International Preliminary Report on Patentability issued Sep. 6, 2016 for International Application No. PCT/US2015/017425, entitled "Anti-CD38 Antibodies for Treatment of Acute Lymphoblastic Leukemia".
International Search Report and Written Opinion mailed Sep. 21, 2015 for International Application No. PCT/US2015/017425, entitled "Anti-CD38 Antibodies for Treatment of Acute Lymphoblastic Leukemia".
International Preliminary Report on Patentability issued Jan. 10, 2019 for International Application No. PCT/EP2017/066063, entitled "Treatment of IgE-MEDIATED Diseases With Antibodies That Specifically Bind CD38".
International Search Report and Written Opinion mailed Sep. 25, 2017 for International Application No. PCT/EP2017/066063, entitled "Treatment of IgE-Mediated Diseases With Antibodies That Specifically Bind CD38".
International Preliminary Report on Patentability mailed May 14, 2020 for International Application No. PCT/US2018/058561, entitled "Methods of Treating High Risk Multiple Myeloma".
International Search Report and Written Opinion mailed Feb. 12, 2019 for International Application No. PCT/US2018/058561, entitled "Methods of Treating High Risk Multiple Myeloma".
International Search Report and Written Opinion mailed Apr. 24, 2020 for International Application No. PCT/US2019/056838, entitled "Method of Providing Subcutaneous Administration of Anti-CD38 Antibodies".
International Preliminary Report on Patentability issued Sep. 6, 2016 for International Application No. PCT/US2015/017420, entitled "Combination Therapies With Anti-CD38 Antibodies".
International Search Report and Written Opinion mailed Jul. 8, 2015 for International Application No. PCT/US2015/017420, entitled "Combination Therapies With Anti-CD38 Antibodies".
Intellectual Property Office of Singapore Written Opinion dated Apr. 17, 2018 for Application No. 11201701867S, entitled "Combination Therapies with Anti-CD38 Antibodies ".
Supplementary European Search Report dated Feb. 21, 2018 for European Application No. EP 15839752 , entitled "Combination Therapies with Anti-CD38 Antibodies".
Non Final Office Action for U.S. Appl. No. 15/340,290 date mailed Nov. 20, 2017.
Final Office Action for U.S. Appl. No. 15/340,290 date mailed May 16, 2018.
Non Final Office Action for U.S. Appl. No. 15/340,290 date mailed Oct. 10, 2018.
Non Final Office Action for U.S. Appl. No. 15/366,474 date mailed Nov. 20, 2017.
Final Office Action for U.S. Appl. No. 15/366,474 date mailed May 16, 2018.
Applicant Initiated Interview for U.S. Appl. No. 15/366,474 date mailed Sep. 17, 2018.
Non Final Office Action for U.S. Appl. No. 15/366,474 date mailed Oct. 11, 2018.
Non Final Office Action for U.S. Appl. No. 15/189,577 date mailed Oct. 31, 2017.

(56) References Cited

OTHER PUBLICATIONS

Final Office Action for U.S. Appl. No. 15/189,577 date mailed Apr. 13, 2018.
Non Final Office Action for U.S. Appl. No. 15/189,577 date mailed Sep. 28, 2018.
Non Final Office Action for U.S. Appl. No. 14/847,428 date mailed Sep. 23, 2016.
Non Final Office Action for U.S. Appl. No. 15/386,391 date mailed Jun. 18, 2018.
Non Final Office Action for U.S. Appl. No. 15/160,476 date mailed Sep. 15, 2017.
Non Final Office Action for U.S. Appl. No. 15/160,476 date mailed Nov. 5, 2018.
Final Office Action for U.S. Appl. No. 15/160,476 date mailed Apr. 23, 2018.
Non Final Office Action for U.S. Appl. No. 14/956,890 date mailed Nov. 25, 2016.
Final Office Action for U.S. Appl. No. 14/956,890 date mailed Jul. 24, 2018.
Non Final Office Action for U.S. Appl. No. 15/340,214 date mailed May 16, 2018.
Non Final Office Action for U.S. Appl. No. 14/629,965 date mailed Dec. 21, 2015.
Final Office Action for U.S. Appl. No. 14/629,965 date mailed Apr. 29, 2016.
Notice of Allowance for U.S. Appl. No. 14/629,965 date mailed Apr. 13, 2017.
Non Final Office Action for U.S. Appl. No. 15/445,225 date mailed Jun. 29, 2018.
Final Office Action for U.S. Appl. No. 15/445,225 date mailed Dec. 17, 2018.
Non Final Office Action for U.S. Appl. No. 15/651,333 date mailed Sep. 27, 2018.
Final Office Action for U.S. Appl. No. 15/386,391 date mailed Dec. 28, 2018.
Final Office Action for U.S. Appl. No. 14/956,890 date mailed Jan. 14, 2019.
Notice of Allowance for U.S. Appl. No. 15/651,333 date mailed Feb. 21, 2019.
Notice of Allowance for U.S. Appl. No. 15/189,577 date mailed Mar. 5, 2019.
Final Office Action for U.S. Appl. No. 15/340,290 date mailed Mar. 11, 2019.
Notice of Allowance for U.S. Appl. No. 15/386,391 date mailed Mar. 29, 2019.
Notice of Allowance for U.S. Appl. No. 15/340,290 date mailed May 22, 2019.
Notice of Allowance for U.S. Appl. No. 15/651,333 date mailed May 31, 2019.
Final Office Action for U.S. Appl. No. 15/160,476 date mailed Jun. 14, 2019.
Notice of Allowance for U.S. Appl. No. 15/445,225 date mailed Jul. 29, 2019.
Notice of Allowance for U.S. Appl. No. 15/386,391 date mailed Jul. 30, 2019.
Non-Final Office Action for U.S. Appl. No. 14/956,890 date mailed Jul. 30, 2019.
Notice of Allowance for U.S. Appl. No. 15/189,577 date mailed Sep. 12, 2019.
Notice of Allowance for U.S. Appl. No. 15/651,333 date mailed Oct. 9, 2019.
Notice of Allowance for U.S. Appl. No. 15/386,391 date mailed Nov. 18, 2019.
Notice of Allowance for U.S. Appl. No. 15/445,225 date mailed Dec. 4, 2019.
Notice of Allowance for U.S. Appl. No. 15/189,577 date mailed Dec. 19, 2019.
Non Final Office Action for U.S. Appl. No. 15/160,476 date mailed Dec. 20, 2019.
Final Office Action for U.S. Appl. No. 14/956,890 date mailed Jan. 7, 2020.
Non-Final Office Action for U.S. Appl. No. 15/798,670 mailed Jan. 22, 2020.
English translation of Office Action for JP Application No. 2016-554350, mailed Nov. 27, 2018.
Notice of Allowance for U.S. Appl. No. 15/445,225 date mailed Mar. 25, 2020.
Notice of Allowance for U.S. Appl. No. 15/189,577 date mailed Mar. 31, 2020.
Notice of Allowance for U.S. Appl. No. 15/160,476 date mailed May 4, 2020.
Notice of Allowance for U.S. Appl. No. 16/380,994 date mailed May 12, 2020.
Notice of Allowance for U.S. Appl. No. 16/460,754 date mailed May 18, 2020.
Notice of Allowance for U.S. Appl. No. 15/445,225 date mailed Jul. 15, 2020.
Notice of Allowance for U.S. Appl. No. 14/956,890 date mailed Jul. 29, 2020.
Non-Final Office Action for U.S. Appl. No. 15/798,670 mailed Aug. 7, 2020.
Notice of Allowance for U.S. Appl. No. 16/380,994 date mailed Aug. 12, 2020.
Non-Final Office Action for U.S. Appl. No. 16/162,355 mailed Aug. 13, 2020.
Non-Final Office Action for U.S. Appl. No. 16/177,239 mailed Aug. 24, 2020.
Notice of Allowance for U.S. Appl. No. 16/460,754 date mailed Sep. 10, 2020.
ASH Clinical News, "Is Daratumumab Plus Lenalidomide-Dexamethasone a New Standard for Transplant-Ineligible Myeloma," Dated Jan. 1, 2019, Retrieved from Internet URL: https://www.ashclinicalnews.org/on-location/ash-annual-meeting/daratumumab-plus-lenalidomid; Retrieved Oct. 28, 2022 (2 pages).
Avet-Loiseau, H. et al., "Evaluation of Minimal Residual Disease (MRD) in Relapsed/Refractory Multiple Myeloma (RRMM) Patients Treated with Daratumumab in Combination with Lenalidomide Plus Dexamethasone or Bortezomib Plus Dexamethasone," Blood, vol. 128; No. 22; 246; 7 pages (2016).
Bauer, Fromming, Fuhrer, "Lehrbuch der Pharmazeutischen Technologie" 8th Edition, Wissenschaftliche Verlagsgesellschaft Stuttgart, Chapter 9; 238-243 (2006). (concise explanation met by submission of the enclosed Opponent's submission filed by Dr. Markus Breuer cited as Other Document 134).
Bittner, B. et al., "Development of a Subcutaneous Formulation for Trastuzumab—Nonclinical and Clinical Bridging Approach to the Approved Intravenous Dosing Regimen," Arzneimittelforschung, vol. 62; 401-409 (2012).
Bittner, B. et al., "Non-Clinical Pharmacokinetic /Pharmacodynamic and Early Clinical Studies Supporting Development of a Novel Subcutaneous Formulation for the Monoclonal Antibody Rituximab," Drug Res., vol. 64; 569-575 (2014).
Bittner, B. et al., "Subcutaneous Administration of Biotherapeutics: An Overview of Current Challenges and Opportunities," BioDrugs, vol. 32; 425-440 (2018).
Bookbinder, L.H. et al., "A recombinant human enzyme for enhanced interstitial transport of therapeutics," Journal of Controlled Release, vol. 114; 230-241 (2006).
CAS Registry Results, dated Oct. 9, 2020, Registry No. 757971-58-7, "36-482-Hyaluronoglucosaminidase PH20 (human)," 6 pages.
Chari, A., et al., "Subcutaneous Daratumumab (DARA) in Patients (Pts) With Relapsed or Refractory Multiple Myeloma (RRMM): Part 2 Update of the Open-label, Multicenter, Dose-escalation Phase 1b Study (PAVO)", Poster Presented at the Annual Meeting of the American Society of Clinical Oncology (ASCO); June Jan. 5, 2018; Chicago, Illinois.
Chaulagain, C.P. et al., "Pre-clinical translational studies of daratumumab in patients with myeloma or AL amyloidosis undergoing autologous hematopoietic stem cell transplantation (SCT)," Journal of Clinical Oncology , May 20, 2015, vol. 33, No. 15 suppl., pp. 8587-8587.
CHMP Assessment Report for Herceptin (trastuzumab), 70 pages (2013).

(56) References Cited

OTHER PUBLICATIONS

CHMP Assessment Report for Mabthera (rituximab), 103 pages (2014).
Chung, C.H., "Managing Premedications and the Risk for Reactions to Infusional Monoclonal Antibody Therapy," The Oncologist, vol. 13; 725-732 (2008).
ClinicalTrials.gov, "Daratumumab (HuMax-CD38) Safety Study in Multiple Myeloma," Identifier: NCT00574288; Latest version posted: Apr. 27, 2018 (10 pages).
ClinicalTrials.gov, "An Investigational Immuno-Therapy Study to Determine the Safety and Effectiveness of Nivolumab and Daratumumab in Patients with Multiple Myeloma," Identifier: NCT01592370; Latest version posted: Jun. 18, 2021 (10 pages).
ClinicalTrials.gov, "History of Changes for Study: NCT02252172: Study Comparing Daratumumab, Lenalidomide, and Dexamethasone With Lenalidomide and Dexamethasone in Participants With Previously Untreated Multiple Myeloma," U.S. National Library of Medicine, ClinicalTrials.gov Archive, Oct. 17, 2017 (24 pages).
ClinicalTrials.gov, "History of Changes for Study: NCT02519452: A Study of Daratumumab With the Addition of Recombinant Human Hyaluronidase (rHuPH20) for the Treatment of Participants with Relapsed or Refractory Multiple Myeloma," U.S. National Library of Medicine, ClinicalTrials.gov Archive, Dec. 3, 2020 (12 pages).
ClinicalTrials.gov, "A Study of Daratumumab with the Addition of Recombinant Human Hyaluronidase (rHuPH20) for the Treatment of Participants with Relapsed or Refractory Multiple Myeloma," Identifier: NCT02519452; First Received: Aug. 6, 2015 (5 pages).
Colson, K., "Treatment-related symptom management in patients with multiple myeloma: a review," Support Care Cancer, vol. 23; 1431-1445 (2015).
Common Terminology Criteria for Adverse Events (CTCAE), Version 4.03, U.S. Department of Health and Human Services, 4 pages (2010).
Complete Specification for Indian Application No. 4718/CHENP/2007; published on Jan. 11, 2008 (225 Pages).
Consolidated list of references from Opposition in parent patent EP No. 3370770, 4 pages; Feb. 24, 2022.
Darzalex, Highlights and Prescribing Information, FDA Label, 24 pages (2015).
Darzalex, Highlights and Prescribing Information, FDA Label, 32 pages (2018).
Davies, A. et al., "Pharmacokinetics and safety of subcutaneous rituximab in follicular lymphoma (SABRINA): stage 1 analysis of a randomised phase 3 study," The Lancet, vol. 15; 343-352 (2014).
Dimopoulos, M.A. et al., "Daratumumab plus pomalidomide and dexamethasone versus pomalidomide and dexamethasone alone in previously treated multiple myeloma (APOLLO): an open-label, randomised, phase 3 trial," Lancet Oncol, vol. 22; 801-812 (2021).
Doessegger, L. and Banholzer, M.L., "Clinical development methodology for infusion-related reactions with monoclonal antibodies," Clinical & Translational Immunology, vol. 4; e39; 9 pages (2015).
Drach, J. et al., "Retinoic Acid-induced Expression of CD38 Antigen in Myeloid Cells is Mediated through Retinoic Acid Receptor-$\alpha^1$," Cancer Research, vol. 54; 1746-1752 (1994).
Durie, B.G.M. et al., "International Uniform Response Criteria for Multiple Myeloma," Leukemia, vol. 20; 1467-1473 (2006).
European Medicines Agency, Summary of Product Characteristics for Rituximab; 153 pages; Oct. 30, 2009, https://www.cma.curopa.cu/cn/documents/product-information/mabthera-cpar-product-information_en.pdf.
European Union Clinical Trials Register Clinical Trials Register, EudraCT No. 2014-002272-88; Title: "A Phase 3, Randomized, Controlled, Open-label Study of VELCADE (Bortezomlb) Melphalan-Prednisone (VMP) Compared to Daratumumab In Combination with VMP (D-VMP), In Subjects with Previously Untreated Multiple Myeloma who are Inellgible for High-dose Therapy," 6 pages (2015).
European Union Clinical Trials Register Clinical Trials Register, EudraCT No. 2014-002273-11; Title: "A Phase 3 Study Comparing Daratumumab, Lenalidomide, and Dexamethasone (DRd) vs Lenalidomide and Dexamethasone (Rd) In Subjects with Previously Untreated Multiple Myeloma who are Ineligible for High Dose Therapy," 7 pages (2015).
European Union Clinical Trials Register Clinical Trials Register, EudraCT No. 2013-005525-23; Title: "Phase 3 Study Comparing Daratumumab, Lenalidomide, and Dexamethasone (DRd) vs Lenalidomide and Dexamethasonc (Rd) in Subjects with Relapsed or Refractory Multiple Myeloma," 7 pages (2014).
European Union Clinical Trials Register Clinical Trials Register, EudraCT No. 2014-000255-85; Title: "Phase 3 Study Comparing Daratumumab, Bortezomlb and Dexamethasone (DVd) vs Bortezomib and Dexamethasone (Vd) In Subjects With Relapsed or Refractory Multiple Myeloma," 6 pages (2014).
Faiman, B. et al., "Steroid-Associated Side Effects in Patents with Multiple Myeloma: Consensus Statement of the IMF Nurse Leadership Board," Clinical Journal of Oncology Nursing, vol. 12; No. 3; 53-63 (2008).
Frost, G.I., "Recombinant human hyaluronidase (rHuPH20): an enabling platform for subcutaneous drug and fluid administration," Expert Opinion Drug Deliv., vol. 4; No. 4; 427-440 (2007).
Gay, F. and Palumbo, A., "Management of Older Patients with Multiple Myeloma," Blood Reviews, vol. 25; 65-73 (2011).
Goel, M. et al., "Plasticity within the Antigen-Combining Site May Manifest as Molecular Mimicry in the Humoral Immune Response," The Journal of Immunology, vol. 173; 7358-7367 (2004).
Haller, M.F., "Converting Intravenous Dosing to Subcutaneous Dosing," Pharmaceutical Technology, 118-132 (2007).
Halozyme, "Halozyme Therapeutics Reports Selection of First Product Candidate Under Janssen Collaboration," Press Release, 4 pages (2015).
Hamizi, S. et al., "Subcutaneous trastuzumab: development of a new formulation for treatment of HER2-positive carly breast cancer," Onco Targets and Therapy, vol. 6; 89-94 (2013).
Herceptin, Highlights and Prescribing Information, FDA Label, 33 pages (1998).
Highlights of Prescribing Information, Rituxan, 53 pages (1997).
Highlights of Prescribing Information, Rituxan (rituximab) injection, 44 pages (1997).
Hydase, Highlights and Prescribing Information, FDA Label, 6 pages (2005).
Hylenex, Highlights and Prescribing Information, FDA Label, 9 pages (2005).
Jaccard, A. et al., "Efficacy of bortezomib, cyclophosphamide and dexamethasone in treatment—naïve patients with high-risk cardiac AL amyloidosis (Mayo Clinic stage III)," Haematologica, vol. 99; No. 9; 1479-1485 (2014).
Jackisch, C. et al., "Subcutaneous Administration of Monoclonal Antibodies in Oncology," Geburtsh Frauenhelk, vol. 74; 343-349 (2014).
Janssen Initiates Rolling Submission of Biologic License Application (BLA) for daratumumab with U.S. FDA for the Treatment of Multiple Myeloma, News Release, 3 pages (2015).
Janssen to Demonstrate Breadth of Oncology Portfolio with 41 Clinical Data Presentations at the 2014 American Society of Hematology (ASH) Annual Meeting [online], Nov. 6, 2014, Internet :<URL: https://www.jnj.com/media-center/press-releases/janssen-to-demonstrate-breadth-of-oncology-portfolio-with-41-clinical-data-presentations-at-the-2014-american-society-of-hematology-ash-annual-meeting>; 8 pages.
Janssen Submits Marketing Authorisation Application for Daratumumab for European Patients with Heavily Pre-treated Multiple Myeloma, Janssen-Cilag International NV; 7 pages (2015).
Jolles, S., "Hyaluronidase facilitated subcutaneous immunoglobulin in primary immunodeficiency," Immuno Targets and Therapy, vol. 2; 125-133 (2013).
Khagi, Y. and Mark, T., "Potential role of daratumumab in the treatment of multiple myeloma," Onco Targets and Therapy, 1095-1100 (2014).
Khan, T. and Salunke, D.M., "Adjustable Locks and Flexible Keys: Plasticity of Epitope-Paratope Interactions in Germline Antibodies," The Journal of Immunology, vol. 192; 5398-5405 (2014).

(56) References Cited

OTHER PUBLICATIONS

Kim, H. et al., "Overview of methods for comparing the efficacies of drugs in the absence of head-to-head clinical trial data," Br. J. Clin. Pharmacol., vol. 77; No. 1; 116-121 (2013).
Knowles, S.P. et al., "Safety of recombinant human hyaluronidase PH20 for subcutaneous drug delivery," Expert Opinion on Drug Delivery, vol. 18; No. 11; 1673-1685 (2021).
Kyle, R.A. and Rajkumar, S.V., "Criteria for diagnosis, staging, risk stratification and response assessment of multiple myeloma," Leukemia, vol. 23; 3-9 (2009).
Kyle, R.A. et al., "Clinical Course and Prognosis of Smoldering (Asymptomatic) Multiple Myeloma," The New England Journal of Medicine, vol. 356; 2582-2590 (2007).
Kyle, R.A. et al., "Review of 1027 Patients with Newly Diagnosed Multiple Myeloma," May Clinic Proc., vol. 78; 21-33 (2003).
Laubach, J.P. et al., "The challenge of cross-trial comparisons using limited data," haematologica, vol. 99; e145; 2 pages (2014).
Laurini, J.A. et al., "Classification of non-Hodgkin lymphoma in Central and South America: a review of 1028 cases," Blood, vol. 120; vol. 24; 4795-4801 (2012).
Lefranc, M. et al., "IMGT unique numbering for immunoglobulin and T cell receptor variable domains and Ig superfamily V-like domains," Developmental & Comparative Immunology, vol. 27; 55-77 (2003).
Lokhorst, H.M. et al., "Targeting CD38 with Daratumumab Monotherapy in Multiple Mycloma," The New England Journal of Medicine, vol. 373; 1207-1219 (2015).
Lokhorst, H.M. et al., "Targeting CD38 with Daratumumab Monotherapy in Multiple Myeloma," The New England Journal of Medicine, vol. 373; 1207-1219 (2015); Supplemental Appendix.
Lonial, S. et al., "Phase II study of daratumumab (DARA) monotherapy in patients with greater than or equal to 3 lines of prior therapy or double refractory multiple myeloma (MM): 54767414MMY2002 (Sirius)," Journal of Clinical Oncology, vol. 33; No. 18_Suppl (2015).
Lonial, S. et al., "Monoclonal antibodies in the treatment of multiple myeloma: current status and future perspectives," Leukemia, vol. 30; 526-535 (2016).
Mahajan, S. et al., "The evolution of stem-cell transplantation in multiple myeloma," Therapeutic Advances in Hematology, vol. 9; No. 5; 123-133 (2018).
Mariuzza, R.A. eet al., "The Structural Basis of Antigen-Antibody Recognition," Ann. Rev. Biophys. Biophys. Chem., vol. 16; 139-159 (1987).
Mateos, M. et al., "Daratumumab plus Bortezomib, Melphalan, and Prednisone for Untreated Myeloma," N England J Med, vol. 378; 518-528 (2018).
Maury, M. et al., "Spray-drying of proteins: effects of sorbitol and trehalose on aggregation and FT-IR amide I spectrum of an immunoglobulin G," European Journal of Pharmaceutics and Biopharmaccutics, vol. 59; 251-261 (2005).
McCudden, C. et al., "Monitoring multiple myeloma patients treated with daratumumab: teasing out monoclonal antibody interference," Clin Chem Lab Med, vol. 54; No. 6; 1095-1104 (2016).
Moreau, P. et al., "Rituximab in CD20 positive multiple myeloma," Leukemia, vol. 21; 835-836 (2007).
Moreau, P. et al., "Practical Considerations for the Use of Daratumumab, a Novel CD38 Monoclonal Antibody, in Myeloma," Drugs, vol. 76; 853-867 (2016).
Nahi, H. et al., "An open-label, dose escalation phase 1b study of subcutaneous daratumumab with recombinant human hyaluronidase in patients with relapsed or refractory multiple myeloma (PAVO)," Journal of Clinical Oncology, vol. 34; No. 15; 4 pages (2016).
Negrin, R., Patient education: Hematopoietic transplantation (bone marrow transplantation) (Beyond the Basics), Retrieved from Internet URL: https://www.uptodate.com/contents/hematopoietic-cell-transplantation-bone-marrow-transplantation-beyond-the-basics, 15 pages; Retrieved on Oct. 27, 2022.
Ocio, E.M. et al., "New drugs and novel mechanisms of action in multiple myeloma in 2013: a report from the International Myeloma Working Group (IMWG)," Leukemia, vol. 28; 525-542 (2014).
Ohaegbulam K C et al.: "Human cancer immunotherapy with antibodies to the PD-1 and PD-L1 pathway", Trends in Molecular Medicine, Jan. 2015; 21 (1): 24-33.
Ortolani, C., "CD38: Antigen: Flow Cytometry of Hematological Malignancies," Blackwell Publishing, 1st Edition, 68-70 (2011).
Palumbo, A. et al., "International Myeloma Working Group guidelines for the management of multiple myeloma patients ineligible for standard high-dose chemotherapy with autologous stem cell transplantation," Leukemia, vol. 23: 1716-1730 (2009).
Palumbo, A. and Anderson, K., "Multiple Mycloma," The New England Journal of Medicine, vol. 364; 1046-1060 (2011).
Patent Assignment Cover Sheet for U.S. Appl. No. 16/380,994, 6 pages; filed Sep. 11, 2019.
Phase 3 COLUMBIA study Investigating a Subcutaneous Formulation of DARZALEX (daratumumab) Showed Non-Inferiority to Intravenous Administration in Patients with Relapsed/Refractory Multiple Myeloma, Chicago, 7 pages (2019).
Phipps, C., et al., "Daratumumab and its potential in the treatment of multiple myeloma: overview of the preclinical and clinical development," Ther. Adv. Hematol., vol. 6; No. 3; 120-127 (2015).
Pivot, X. et al., "Patients' preferences for subcutaneous trastuzumab versus conventional intravenous infusion for the adjuvant treatment of HER2-positive early breast cancer: final analysis of 488 patients in the international, randomized, two-cohort PrefHer study," Annals of Oncology, vol. 25; 1979-1987 (2014).
Poosarla, V.G. et al., "Computational De Novo Design of Antibodies Binding to a Peptide With High Affinity," Biotechnology & Bioengineering, vol. 114; No. 6; 1331-1342 (2017).
Pre-Grant Notice of Opposition filed in Indian Application No. 201617029109, by Indian Pharmaceutical Alliance, dated Feb. 24, 2022 (30 pages).
Preliminary Opinion of the Opposition Division, as cited in EP Opposition against EP Patent No. 3370770; 13 pages; dated Aug. 8, 2022.
Pui, C. and Jeha, S., "New therapeutic strategies for the treatment of acute lymphoblastic leukemia," Nature Reviews, vol. 6; 149-165 (2007).
Rader, C. et al., "A phage display approach for rapid antibody humanization: Designed combinatorial V gene libraries," Proc. Natl. Acad. Sci, vol. 95; 8910-8915 (1998).
Raj, T.A. et al., "Vincristine sulfate liposomal injection for acute lymphoblastic leukemia," International Journal of Nanomedicine, vol. 8; 4361-4369 (2013).
Rajkumar, S.V. et al., "Consensus recommendations for the uniform reporting of clinical trials: Report of the International Myeloma Workshop Consensus Panel 1," Blood, vol. 117; No. 18; 4691-4695 (2011).
Rituxan (tituximab), Highlights of prescribing information. Rituxan (IV administered Rituximab; 35 pages (1997).
Rosengren, S. et al., Clinical Immunogenicity of rHuPH20, a Hyaluronidasc Enabling Subcutaneous Drug Administration, The AAPS Journal, vol. 17; No. 5; 1144-1156 (2015).
Ruberg, E-M. and FrieB, W., "Sensibel und stressanfallig," Pharmazeutische Zeitung, 156 JG, AUSG. 50; 15 pages (2011). concise explanation met by submission of the enclosed Notice of Opposition filed by Dr. Markus Breuer, cited as Other Document 128).
Rudikoff, S. et al., "Single amino acid substitution altering antigen-binding specificity," Proc. Natl. Acad., col. 79; 1979-1983 (1982).
Ryan, et al., "Potentiation of Anti-Myeloma Activity of Daratumumab with Combination of Cyclophosphamide, Lenalidomide or Bortezomib via a Tumor Secretory Response That Greatly Augments Macrophage-Induced ADCP," Annual Meeting at the Haematology Association of Ireland, Oct. 15, 2016; 20 pages.
San-Miguel, J., et al., "Subcutaneous Daratumumab in Patients with Relapsed or Refractory Multiple Myeloma: Part 2 Update of the Open-label, Multicenter, Dose Escalation Phase 1b Study (PAVO)", Poster Presented at the 23rd European Hematology Association (EHA) Annual Congress; Jun. 14-17, 2018; Stockholm, Sweden.

(56) References Cited

OTHER PUBLICATIONS

Solal-Deligny, P., "Rituximab by subcutaneous route," Expert Rev. Hematol., vol. 8; No. 2; 147-153 (2015).
Sondergeld, P. et al., "Monclonal Antibodies in Myeloma," Clinical Advances in Hematology & Oncology, vol. 13; Issue 9; 599-609 (2015).
Statement on a Nonproprietary Name Adopted by the USAN Council, Hyaluronidase, CAS Registry No. 757971-58-7; 1 page; No date provided.
Strickley, R.G. and Lambert, W.J., "A review of formulations of commercially available antibodies," Journal of Pharmaceutical Sciences, vol. 110; 2590-2608 (2021).
Taussig, D.C. et al., "Anti-CD38 antibody-mediated clearance of human repopulating cells masks the heterogeneity of leukemia-initiating cells," Blood, vol. 112; No. 3; 568-575 (2008).
Thomas, D.A. et al., "Chemoimmunotherapy with Hyper-CVAD plus Rituximab for the Treatment of Adult Burkitt and Burkitt-Type Lymphoma or Acute Lymphoblastic Leukemia," The American Cancer Society, vol. 106; No. 7; 1569-1580 (2006).
Usmani, S.Z. et al., "Final analysis of the phase III non-inferiority COLUMBA study of subcutaneous versus intravenous daratumumab in patients with relapsed or refractory multiple myeloma," Haematologica, vol. 107; 2408-2417 (2022).
Wang, W. et al., "Antibody Structure, Instability, and Formulation," Journal of Pharmaceutical Sciences, vol. 96; 1-26 (2007).
Warne, N.W., "Development of high concentration protein biopharmaceuticals: The use of platform approaches in formulation development," European Journal of Pharmaceutics and Biopharmaceutics, vol. 78; 208-212 (2011).
Wasserman, R.L., "Progress in Gammaglobulin Therapy for Immunodeficiency: From Subcutaneous to Intravenous Infusions and Back Again," J. Clin. Immunol., vol. 32 ;1153-1164 (2012).
Wasserman, R.L., "Overview of recombinant human hyaluronidase-facilitated subcutaneous infusion of IgG in primary immunodeficiencies," Immunotherapy, vol. 6; No. 5; 553-567 (2014).
WHO Drug Information, International Nonproprietary Names for Pharmaceutical Substances (INN), Proposed INN: List 101, vol. 23; No. 2; 64 pages (2009).
WHO Drug Information, International Nonproprietary Names for Pharmaceutical Substances (INN), Recommended INN: List 63, 40 pages (2010).
Wu, et al., An Analysis of the Sequences of the Variable Regions of Bence Jones Proteins and Myeloma Light Chains and Their Implications for Antibody Complementarity, Journal of Experimental Medicine, 132: 211-250 (1970).
Wunderlich, M. et al., "AML cells are differentially sensitive to chemotherapy treatment in a human xenograft model," eBlood, vol. 121; No. 12; e90-e97 (2013).
Yamamoto, H. et al., "A mammalian homolog of the zebrafish transmembrane protein 2 (TMEM2) is the long-sought-after cell-surface hyaluronidase," J. Biol. Chem., vol. 292; No. 18; 7304-7313 (2017).
Zadnikova, P. et al., "The Degradation of Hyaluronan in the skin," Biomolecules, vol. 12; 251, 17 pages (2022).
Zagouri, F. et al., "Emerging antibodies for the treatment of multiple myeloma," Expert Opinion on Emerging Drugs, vol. 21; No. 2; 225-237 (2016).
Zojer, N. et al., "Rituximab treatment provides no clinical benefit in patients with pretreated advanced multiple myeloma," Leukemia & Lymphoma, vol. 47; No. 6; 1103-1109 (2006).
International Preliminary Report on Patentability mailed Apr. 29, 2021 for International Application No. PCT/US2019/056838, entitled "Method of Providing Subcutaneous Administration of Anti-CD38 Antibodies".
International Preliminary Report on Patentability for International Application No. PCT/IB2020/051484, mailed Sep. 2, 2021.
International Search Report and Written Opinion for International Application No. PCT/IB2020/051484, mailed Jul. 2, 2020.

Declaration of Professor Paul Anthony Dalby, in Opposition Proceedings against European Patent No. 3370770, 20 pages (Dated May 2022).
Declaration of Professor Christian Jackisch, in Opposition Proceedings against European Patent No. 3370770, 8 pages (Dated May 10, 2022).
Declaration of Professor Adrian Llewellyn Harris, in Opposition Proceedings against European Patent No. 3370770, 109 pages (Dated Dec. 20, 2022).
Declaration of Dr. Richard Senderoff, in Opposition Proceedings against European Patent No. 3370770, 28 pages (Dated Dec. 20, 2022).
Declaration of Professor Dr. Andreas Zimmer, in Opposition Proceedings against European Patent No. 3370770, 5 pages (Dated Jan. 9, 2023).
Second Declaration of Professor Christian Jackisch, in Opposition Proceedings against European Patent No. 3370770, 8 pages (Dated Jan. 6, 2023).
Notice of Opposition Dated Oct. 20, 2021 by Opponent König Szynka Tilmann von Renesse, filed in European Patent No. 3 370 770 B1.
Notice of Opposition Dated Oct. 19, 2021 by Opponent Patent Boutique LLP, filed in European Patent No. 3 370 770 B1.
Notice of Opposition Dated Oct. 20, 2021 by Opponent Dr. Markus Breuer, filed in European Patent No. 3 370 770 B1.
Notice of Opposition Dated Dec. 22, 2022 by Opponent Dr. Hans Ulrich Dorries, filed in European Patent No. 3 827 845 B1; 44 Pages.
Notice of Opposition Dated Dec. 27, 2022 by Opponent Konig Szynka Tilmann von Renesse, filed in European Patent No. 3 827 845 B1; 49 Pages.
Notice of Opposition Dated Dec. 28, 2022 by Opponent Michalski Huttermann & Partner, filed in European Patent No. 3 827 845 B1; 44 Pages.
Notice of Opposition Dated Dec. 29, 2022 by Opponent Patent Boutique LLP, filed in European Patent No. 3 827 845 B1; 49 Pages.
Notice of Opposition Dated Dec. 21, 2022 by Opponent Xbrane Biopharma AB, filed in European Patent No. 3 827 845 B1; 68 Pages.
Opponent's submission by Dr. Markus Breuer dated Oct. 4, 2022 filed in European Patent No. 3 370 770 B1.
Opponent's submission by Konig Szynka Tilmann von Renesse dated Jan. 11, 2023, filed in European Patent No. 3 370 770 B1; 27 Pages.
Opponent's submission by Dr. Markus Breuer dated Jan. 13, 2023, filed in European Patent No. 3 370 770 B1; 11 Pages.
Opponent's submission by Patent Boutique LLP dated Jan. 12, 2023, filed in European Patent No. 3 370 770 B1; 56 Pages.
Reply to Notice of Opposition, filed in European Patent No. 3 370 770 B1, entitled: "Subcutaneous Formulations Of Anti-CD38 Antibodies And Their Uses," 416 pages, dated May 12, 2022.
Reply to Notice of Opposition, filed in European Patent No. 3 370 770 B1, entitled: "Subcutaneous Formulations Of Anti-CD38 Antibodies And Their Uses," 19 pages, dated Jan. 13, 2023.
Non Final Office Action for U.S. Appl. No. 16/840,153 date mailed Aug. 16, 2022.
Applicant Initiated Interview Summary for U.S. Appl. No. 16/840,153 date mailed Jun. 8, 2022.
Non Final Office Action for U.S. Appl. No. 16/840,153 date mailed Mar. 22, 2022.
Applicant Initiated Interview Summary for U.S. Appl. No. 16/840,153 date mailed Apr. 6, 2022.
Notice of Allowance for U.S. Appl. No. 16/840,153 date mailed Dec. 21, 2022.
Non Final Office Action for U.S. Appl. No. 16/927,947 date mailed Mar. 7, 2023.
Non Final Office Action for U.S. Appl. No. 17/116,822 date mailed Mar. 8, 2023.
Non Final Office Action for U.S. Appl. No. 17/116,835 date mailed Mar. 8, 2023.
Non Final Office Action for U.S. Appl. No. 16/986,214 date mailed Feb. 28, 2023.

(56) References Cited

OTHER PUBLICATIONS

Notice of Allowance for U.S. Appl. No. 16/162,355 mailed Apr. 9, 2021.
Non Final Office Action for U.S. Appl. No. 16/741,542 date mailed Jul. 12, 2022.
Notice of Allowance for U.S. Appl. No. 16/741,542 date mailed Nov. 2, 2022.
Non Final Office Action for U.S. Appl. No. 16/741,542 date mailed Mar. 17, 2023.
Non-Final Office Action for U.S. Appl. No. 16/312,133 mailed Oct. 28, 2021.
Notice of Allowance for U.S. Appl. No. 16/312,133 mailed Sep. 2, 2022.
Final Office Action for U.S. Appl. No. 16/312,133 mailed May 12, 2022.
Final Office Action for U.S. Appl. No. 15/798,670 mailed Aug. 10, 2021.
Non-Final Office Action for U.S. Appl. No. 15/798,670 mailed Apr. 2, 2021.
Final Office Action for U.S. Appl. No. 15/798,670 mailed Dec. 16, 2020.
Non-Final Office Action for U.S. Appl. No. 15/798,670 mailed Feb. 4, 2022.
Non-Final Office Action for U.S. Appl. No. 16/177,239 mailed Sep. 21, 2021.
Final Office Action for U.S. Appl. No. 16/177,239 mailed Feb. 10, 2021.
Notice of Allowance for U.S. Appl. No. 16/177,239, mailed Oct. 13, 2022.
Final Office Action for U.S. Appl. No. 16/177,239 date mailed Mar. 4, 2022.
Notice of Allowance for U.S. Appl. No. 16/177,239 date mailed Feb. 3, 2023.
Notice of Allowability for U.S. Appl. No. 16/177,239, mailed Feb. 27, 2023.
Non-Final Office Action for U.S. Appl. No. 16/656,569 mailed Aug. 26, 2021.
Non Final Office Action for U.S. Appl. No. 17/015,017 date mailed Dec. 23, 2022.
Final Office Action for U.S. Appl. No. 17/015,017 date mailed Apr. 3, 2023.
Non Final Office Action for U.S. Appl. No. 16/797,301 date mailed Jul. 28, 2022.
Final Office Action for U.S. Appl. No. 16/797,301 date mailed Feb. 17, 2023.
Notice of Allowance for U.S. Appl. No. 16/741,542 date mailed Apr. 10, 2023.
Final Office Action for U.S. Appl. No. 16/830,585 date mailed Oct. 26, 2022.
Final Office Action for U.S. Appl. No. 16/830,763 date mailed Oct. 24, 2022.
Final Office Action for U.S. Appl. No. 16/830,810 date mailed Oct. 25, 2022.
Final Office Action for U.S. Appl. No. 16/830,909 date mailed Oct. 26, 2022.
Non Final Office Action for U.S. Appl. No. 17/475,975 date mailed Mar. 10, 2023.
Non Final Office Action for U.S. Appl. No. 16/830,585 date mailed Mar. 17, 2022.
Non Final Office Action for U.S. Appl. No. 16/830,763 date mailed Mar. 17, 2022.
Non Final Office Action for U.S. Appl. No. 16/830,810 date mailed Mar. 15, 2022.
Non Final Office Action for U.S. Appl. No. 16/830,909 date mailed Mar. 17, 2022.
AstraZeneca 206162 Clinical Pharmacology Review 2014, (https://www.accessdata.fda.gov/drugsatfda_docs/nda/2014/206162Orig1s000ClinPharmR.pdf; Application No. 206162Orig1s000; 117 pages.
Child, J.A. et al., "High-Dose Chemotherapy with Hematopoietic Stem-Cell Rescue for Multiple Myeloma," N Engl J Med, vol. 348; 1875-1883 (2003).
City of Hope, "What's the Difference? Biosimilar and generic drug," City of Hope, retrieved from: https://www.cancercenter.com/community/blog/2018/12/whats-the-difference-biosimilar-and-generic-drugs; 3 Pages (Year: 2018).
ClinicalTrials.gov, "A Study to Evaluate Daratumumab in Transplant Eligible Participants with Previously Untreated Multiple Myeloma (Cassiopeia)," Identifier: NCT02541383; First Posted: Sep. 4, 2015 (29 pages).
Darzalex, Highlights and Prescribing Information, FDA Label, 11 pages (2017).
Demarest, T.G. et al., "NAD+ Metabolism in Aging and Cancer," Annual Rev. Cancer Biol., vol. 3; 105-130 (2019).
Gariani, K. et al., "Inhibiting poly ADP-ribosylation increases fatty acid oxidation and protects against fatty liver disease," Journal of Hepatology, vol. 66; 132-141 (2017).
Kaufman, J.L. et al., "Bortezomib, Thalidomide, and Dexamethasone as Induction Therapy for Patients with Symptomatic Multiple Myeloma," Cancer, vol. 116; 3143-3151 (2010).
King, T. et al., "Best Practice for the Administration of Daratumumab in Multiple Myeloma: Australian Myeloma Nurse Expert Opinion," Asia Pac J Oncol Nurs, vol. 5; 270-284 (2018).
Moreau, P. et al., "Multiple Myeloma: ESMO Clinical Practice Guidelines for dianosis, treatment and follow up," Annals of Oncology, vol. 28; Suppl 4; iv52-iv61 (2017).
Multiple Myeloma Treatment Regiments (MMTR), Multiple Myeloma Treatment Regiments (Part 1 of 9), Haymarket Media, Inc., 9 Pages (2017).
Myeloma Australia, "Steroids," Treatment Fact Sheet, Myeloma Australia, retrieved from: https://myeloma.org.au/wp-content/uploads/2018/09/Steroid-FS-Sep18.pdf 2 Pages (2018).
Decision Revoking the European Patent issued in EP Patent No. 3370770, mailed Apr. 20, 2023; 22 Pages.
Provision of the Minutes in Accordance with Rule 124(4) EPC regarding EP Patent No. 3370770, mailed Apr. 20, 2023, 14 pages.
Applicant Initiated Interview Summary for U.S. Appl. No. 16/927,947 date mailed Apr. 19, 2023.
Notice of Allowance for U.S. Appl. No. 16/927,947 date mailed Jun. 22, 2023.
Applicant Initiated Interview Summary for U.S. Appl. No. 17/116,822 date mailed Apr. 19, 2023.
Notice of Allowance for U.S. Appl. No. 17/116,822 date mailed May 12, 2023.
Applicant Initiated Interview Summary for U.S. Appl. No. 17/116,835 date mailed Apr. 19, 2023.
Notice of Allowance for U.S. Appl. No. 17/116,835 date mailed May 11, 2023.
Non-Final Office Action for U.S. Appl. No. 16/312,133 mailed Dec. 8, 2022.
Non Final Office Action for U.S. Appl. No. 17/002,860 date mailed Jun. 27, 2023.
Non Final Office Action for U.S. Appl. No. 17/674,397 date mailed Apr. 24, 2023.
BC Cancer Agency Cancer drug Manual, Oct. 1, 2013, "Hydroxyurea". http://www.bccancer.bc.ca/drug-database-site/Drug%20Index/Hydroxyurea_monograph_1Oct2013.pdf; Retrieved on Nov. 20, 2023; 7 pages (No Author given).
ClinicalTrials.gov, "Safety and Efficacy Study of Eculizumab in Patients with Refractory Generalized Myasthenia Gravis," Identifier: NCT00727194; Latest version: Sep. 13, 2019 (6 pages).
Davies, A. et al., "Pharmacokinetics and safety of subcutaneous rituximab in follicular lymphoma (SABRINA): stage 1 analysis of a randomised phase 3 study," The Lancet, vol. 15; 343-352 (2014); Supplemental Appendix (8 Pages).
Davis, T.A. et al., "Rituximab Anti-CD20 Monoclonal Antibody Therapy in Non-Hodgkin's Lymphoma: Safety and Efficacy of Re-Treatment," Journal of Clinical Oncology, vol. 18; No. 17; 3135-3143 (2000).
Freeley et al., "The 'Ins and Outs' of complement-driven immune responses", Immunol Rev., 274(1), pp. 16-32, Nov. 2016.

(56) References Cited

OTHER PUBLICATIONS

Karakasheva et al., "CD38-Expressing Myeloid-Derived Suppressor Cells Promote Tumor Growth in a Murine Model of Esophageal Cancer", Microenvironment and Immunol., 75(19), pp. 4074-4085, Oct. 1, 2015.
Kwan et al., "Complement regulation of T cell immunity", Immunol Res, 54(0), pp. 247-253, Dec. 2012.
Leukemia—Acute Myeloid—AML—Treatment Options. Cancer. Net, Nov. 19, 2013. archived by the Wayback Machine at https://web.archive.org/web/20131120003806/http://www.cancer.net/print/19072; Retrieved on Nov. 20, 2023; 6 pages (No Author Listed).
Matsuda, M. et al., "Phenotypic analysis of plasma cells in bone marrow using flow cytometry in AL amyloidosis," Amyloid, 10(2), 110-116 (2003).
McLaughlin, P. et al., "Pituximab Chimeric Anti-CD20 Monoclonal Antibody Therapy for Relapsed Indolent Lymphoma: Half of Patients Respond to a Four-Dose Treatment Program," Journal of Clinical Oncology, vol. 16; No. 8; 2825-2833 (1998).
Piro, L.D. et al., "Extended Rituximab )anti-CD20 monoclonal antibody) therapy for relapsed or refractory low-grade or follicular non-Hodgkins lymphoma," Annals of Oncology, vol. 10; 655-661 (1999).
Rituxan (tituximab), Highlights of prescribing information. Rituxan (IV administered Rituximab; 44 pages (1997); Revised 2014.
Van Beurden-Tan et al., "Systemic Literature Review and Network Meta-Analysis of Treatment Outcomes in Relapsed and/or Refractory Multiple Myeloma," Journal of Clinical Oncology, vol. 35; No. 12; 1312-1319 (2017).
Whatcott et al., "Targeting the tumor microenvironment in cancer: why hyaluronidase deserves a second look", Cancer Discov., 1(4), pp. 291-296, Sep. 2011.
Declaration of Professor Paul Anthony Dalby, in Opposition Proceedings against European Patent No. 3827845, 20 pages (Dated Jul. 19, 2023).
Declaration of Peter Hellemans, in Opposition Proceedings against European Patent No. 3827845, 5 pages (Dated Jul. 21, 2023).
Declaration of Tara Masterson, in Opposition Proceedings against European Patent No. 3827845, 4 pages (Dated Jul. 2023).
Declaration of Professor Christian Jackisch, in Opposition Proceedings against European Patent No. 3827845, 11 pages (Dated Jul. 19, 2023).
Reply of the Patentee to the Notices of Opposition in European Patent No. 3 827 845 B1, Jul. 23, 2023 (203 pages).
Final Office Action for U.S. Appl. No. 16/986,214 date mailed Aug. 23, 2023.
Applicant Initiated Interview for U.S. Appl. No. 16/986,214 date mailed Oct. 17, 2023.
Non Final Office Action for U.S. Appl. No. 17/015,017 date mailed Aug. 18, 2023.
Non Final Office Action for U.S. Appl. No. 17/691,050 date mailed Oct. 3, 2023.
Final Office Action for U.S. Appl. No. 17/674,397 date mailed Oct. 18, 2023.
Non Final Office Action for U.S. Appl. No. 16/797,301 date mailed Sep. 22, 2023.
Caraccioio, D. et al., "Exploiting MYC-induced PARPness to target genomic instability in multiple myeloma," Haematologica, vol. 106; No. 1; 185-195 (2021).
CAS Registry Results, Registry No. 945721-28-8, "Daratumumab," 3 pages (2024).
Cavo, M. et al., "Bortezomib-thalidomide-dexamethasone is superior to thalidomide-dexamethasone as consolidation therapy after autologous hematopoietic stem cell transplantation in patients with newly diagnosed multiple myeloma," Blood, vol. 120; No. 1; 9-19 (2012).
CHMP Assessment Report for HyQvia, 68 pages (2013).
ClinicalTrials.gov, "Daratumumab, Thalidomide and Dexamethasone in Relapse and/or Refractory Myeloma," Identifier: NCT03143036; Last Update: Jun. 7, 2018 (15 pages).
Consolidated list of references from Opposition in patent EP No. 3827845, 6 pages; Jul. 24, 2023.
Consolidated list of references from Opposition in patent EP No. 3370770, 4 pages; 2023.
Dakhil, S. et al., "Phase III safety study of rituximab administered as a 90-minute infusion in patients with previously untreated diffuse large B-cell and follicular lymphoma," Leukemia & Lymphoma, vol. 55; No. 10; 2335-2340 (2014).
Felgar, R.E. et al., CD38: an 'orphan' protein that may be finding a home? Leukemia Research, 24.2; 161-162 (2000).
Genmab, "Genmab Announces Positive Topline Results in Phase III CASSIOPEIA Study of Daratumumab in Front Line Multiple Myeloma," Genmab News, 4 Pages (2018).
Green, C. L. et al., The prognostic significance of IDH2 mutations in AML depends on the location of the mutation. Blood, The Journal of the American Society of Hematology, 118.2: 409-412 (2011).
Highlights of Prescribing Information, Darzalex, 27 pages (2015); Revised Nov. 2016.
Kumar, S.K. et al., "Treating Multiple Myeloma Patients with Oral Therapies," Clinical Lymphoma, Myeloma & Leukemia, vol. 17; No. 5; 243-251 (2017).
Ley, T.J. et al., "DNMT3A mutations in acute myeloid leukemia," New England Journal of Medicine, 363.25: 2424-2433 (2010).
Lokhorst, H.M., "Dose-Dependent efficacy of daratumumab (DARA) as monotherapy in patients with relapsed or refractory multiple myeloma (RR MM)," Journal of Clinical Oncology, vol. 32; No. 15; 4 pages (2014).
Lonial, S. et al., "Phase II study of daratumumab (DARA) monotherapy in patients with greater than or equal to 3 lines of prior therapy or double refractory multiple myeloma (MM): 54767414MMY2002 (Sirius)," Identifier: NCT01985126; Presented at ASC Annual Meeting (2015).
Morcos, P.N. et al., "Pharmacokinetics and pharmacodynamics of single subcutaneous doses of tocilizumab administered with or without rHuPH20," International Journal of Clinical Pharmacology and Therapeutics, vol. 15, No. 7/2013; 537-548 (2013).
Moreau, P. et al., "An Open-Label, Multicenter, Phase 1b Study of Daratumumab in Combination with Backbone Regimens in Patients with Multiple Myeloma," Blood, vol. 124; No. 21; 176 (2014).
Palumbo, A. et al., "Melphalan 200 mg/m2 versus melphalan 100 mg/m2 in newly diagnosed myeloma patients: a prospective, multicenter phase 3 study," Blood, vol. 115; No. 10; 1873-1879 (2010).
Quartino, A.L. et al., "Population pharmacokinetic and exposure-response analysis for trastuzumab administered using a subcutaneous "manual syringe" injection or intravenously in women with HER2-positive early breast cancer," Cancer Chemother Pharmacol, vol. 77; 77-88 (2016).
Rajkumar, S.V. et al., "Multiple Myeloma: 2018 update on Diagnosis, Risk-stratification and Management," Am J. Hematol, vol. 93; No. 8; 981-1114 (2019).
Rituxan (tituximab), Highlights of prescribing information. Rituxan (IV administered Rituximab; 53 pages (1997); Revised 2021.
Small, D. et al., "FLT3 mutations: biology and treatment," ASH Education Program Book, 1: 178-184 (2006).
Wasserman, R.L. et al., "Recombinant human hyaluronidase-facilitated subcutaneous infusion of human immunoglobulins for primary immunodeficiency," J Allergy Clin Immunol, vol. 130; 951-957 (2012).
Wynne, C. et al., "Comparison of Subcutaneous and Intravenous Administration of Trastuzumab: A Phase I/Ib Trial in Healthy Male Volunteers and Patients with HER2-Positive Breast Cancer," The Journal of Clinical Pharmacology, vol. 53; No. 2; 192-201 (2012).
Annex to Form 2300—Notice of Opposition, filed on behalf of Konig Szynka Tilmann von Renesse, filed in Opposition for EP Patent 3370770, 39 pages (2024).
Second Declaration of Professor Adrian Llewellyn Harris, in Opposition Proceedings against European Patent No. 3370770, 5 pages (Dated Jan. 3, 2024).
Declaration of Peter Hellemans, in Opposition Proceedings against European Patent No. 3370770, 5 pages (Dated Aug. 24, 2023).
Declaration of Tara Masterson, in Opposition Proceedings against European Patent No. 3370770, 4 pages (Dated Aug. 2023).

(56) References Cited

OTHER PUBLICATIONS

Opponent's submission by Dr. Markus Breuer dated Jan. 15, 2024, filed in European Patent No. 3 370 770 B1; 53 Pages.
Opponents Submission by Dr. Markus Breuer to Comments on Proprietor's Submission , filed in EP Opposition for EP Patent 3370770, 17 pages; dated Oct. 4, 2022.
Representation for Indian Pharmaceutical Alliance in Opposition of Patent for IN Application No. 201617029321, dated May 10, 2022 (29 pages).
Reply of the Patentee, Janssen Biotech, Inc., to the Notices of Opposition in European Patent No. 3370770, Aug. 2023 (63 pages).
Response to Patentee's Statement of Grounds of Appeal, filed by Patent Boutique LLP in European Patent No. 3370770 , dated Jan. 12, 2024 (74 pages).
Response to Patentee's Statement of Grounds of Appeal, filed on behalf of Konig Szynka Tilmann von Renesse in European Patent No. 3370770 , dated Jan. 15, 2024 (106 pages).
Response to Summons to Attend Oral Proceedings in Opposition against EP 3770770, filed on behalf of Dr. Markus Breuer, 11 pages; filed on Jan. 13, 2023.
Non Final Office Action for U.S. Appl. No. 16/986,214 date mailed Dec. 26, 2023.
Notice of Allowance for U.S. Appl. No. 16/986,214 date mailed Jun. 7, 2024.
Non-Final Office Action for U.S. Appl. No. 17/329,057 mailed Dec. 12, 2023.
Final Office Action for U.S. Appl. No. 17/329,057 mailed Apr. 5, 2024.
Non-Final Office Action for U.S. Appl. No. 18/329,443 mailed Jun. 18, 2024.
Notice of Allowance for U.S. Appl. No. 17/015,017 date mailed Nov. 29, 2023.
Notice of Allowance for U.S. Appl. No. 17/015,017 date mailed Apr. 11, 2024.
Final Office Action for U.S. Appl. No. 17/002,860 date mailed Nov. 30, 2023.
Final Office Action for U.S. Appl. No. 17/691,050 date mailed Mar. 8, 2024.
Non Final Office Action for U.S. Appl. No. 17/005,825 date mailed Feb. 28, 2024.
Non Final Office Action for U.S. Appl. No. 17/674,397 date mailed Mar. 1, 2024.
Final Office Action for U.S. Appl. No. 16/797,301 date mailed Jan. 29, 2024.
Bashir, Q. and Acosta, M., "Comparative Safety, Bioavailability, and Pharmacokinetic of Oral Dexamethasone, 4-mg and 20-mg tablets, in Healthy Volunteers Under Fasting and Fed Conditions: A Randomized Open-Label, 3-way Crossover Study," Clinical Lymphoma, Myeloma & Leukemia, vol. 20; No. 11; 768-773 (2020).
Briney, B. et al., "Commonality despite exceptional diversity in the baseline human antibody repertoire," Nature, vol. 566; No. 7744; 393-397 (2019).
Cavo et al. "Bortezomib with thalidomide plus dexamethasone compared with thalidomide plus dexamethasone as induction therapy before, and consolidation therapy after, double autologous stem-cell transplantation in newly diagnosed multiple myeloma: a randomised phase 3 study." Lancet (Year: 2010).
Chen, L. et al., "CD38-Mediated Immunosuppression as a Mechanism of Tumor Cell Escape from PD-1/PD-L1 Blockade," Cancer Discovery, vol. 8; No. 9; 1156-1175 (2018).
De la Lastra, P. et al., "Epitope mapping of 10 monoclonal antibodies against the pig analogue of human membrane cofactor protein (MCP)," Immunology, vol. 96; No. 4; 663-670 (1999).
Fasan, A. et al., "The role of different genetic subtypes of CEBPA mutated AML," Leukemia, 28.4: 794-803 (2014).
Heath, E.M. et al., "Biological and clinical consequences of NPM1 mutations in AML," Leukemia, 31.4: 798-807 (2017).
Janeway, C.A. et al., "Structure of the Antibody Molecule and Immunoglobulin Genes," Immunobiology: The Immune System in Health and Disease, 1997 Garland Publishing Inc., 3:1-3:11 (1997).

KEGG Drug: Daratumumab; Retrieved from Internet URL: https://www.genome.jp/dbget-bin/www_bget?dr:D10777; retrieved on Oct. 17, 2024; 2 pages.
Keyhani, A. et al., "Increased CD38 expression is associated with favorable prognosis in adult acute leukemia," Leukemia research, 24.2: 153-159 (2000).
Macro, M. et al., "Ixazomib and Daratumumab without Dexamethasone (I-Dara) in Elderly Frail RRMM Patients. A Multicenter Phase 2 Study (IFM 2018-02) of the Intergroupe Francophone Du Myelome (IFM)," Blood, Volo. 138; Supplemental_1; 83; 2 pages (2021).
Moreau, P. et al., "Bortezomib, thalidomide, and dexamethasone with or without daratumumab before and after autologous stem-cell transplantation for newly diagnosed multiple myeloma (CASSIOPEIA): a randomised, open label, phase 3 study," Lancet, vol. 394; 29-38 (2019).
San-Miguel J, et al. "Depth of Response and MRD with Daratumumab Plus Lenalidomide and Dexamethasone (DRd) vs Lenalidomide and Dexamethasone (Rd) in RRMM: POLLUX". 16th International Myeloma Workshop; Mar. 2017. OP-028, p. e17-18.
Shibayama, H. et al., "Subcutaneous delivery of daratumumab in Japanese patients with relapsed/refractory multiple myeloma," Internationl Journal of Hematology, vol. 113; 112-121 (2021).
Siddiqui, B.A. et al., "Immune and pathologic responses in patients with localized prostate cancer who received daratumumab (anti-CD38) or edicotinib (CSF-1R inhibitor)," ImmunoTherapy of Cancer, vol. „,; e006262; 12 pages (2023).
Spencer A, et al. "Depth of Response and MRD with Daratumumab Plus Bortezomib and Dexamethasone (DVd) vs Bortezomib and Dexamethasone (Vd) in RRMM: CASTOR". 16th International Myeloma workshop; Mar. 2017. PS-151(d), p. e85.
Stege, C.A.M. et al., "Efficacy and Tolerability of Ixazomib, Daratumumab and Low Dose Dexamethasone (Ixa Dara dex) in Unfit and Frail Newly Diagnosed Multiple Myeloma (NDMM) Patients; Results of the Interim Efficacy Analysis of the Phase II HOVON 143 Trial," Blood, vol. 134; Supplemental_1; 695; 4 pages (2019).
International Preliminary Report on Patentability mailed May 16, 2024 for International Application No. PCT/IB2022/060616, entitled "Corticosteroid Reduction in Treatment with Anti-CD38 Antibodies".
Opponent's submission by Xbrane Biopharma AB dated Jul. 15, 2024, filed in European Patent No. 3 827 845 B1; 7 Pages.
Opponent's submission by Patent Boutique LLP dated Aug. 23, 2024, filed in European Patent No. 3 827 845 B1; 52 Pages.
Opponent's submission by Huttermann, dated Aug. 22, 2024, filed in European Patent No. 3 827 845 B1; 32 Pages.
Opponent's submission by Ulrich Dorries, dated Aug. 23, 2024, filed in European Patent No. 3 827 845 B1; 22 Pages.
Opponent's submission by Renesse, dated Aug. 22, 2024, filed in European Patent No. 3 827 845 B1; 14 Pages.
Representation for Indian Pharmaceutical Alliance in Opposition of Patent for IN Application No. 201617029109, dated Feb. 24, 2022 (30 pages).
Reply to Notice of Opposition, filed in European Patent No. 3827845 B1, entitled: "Subcutaneous Formulations Of Anti-CD38 Antibodies And Their Uses," 18 pages, dated Oct. 14, 2024.
Information about results of Oral Proceedings for in Opposition against EP 3827845, dated Oct. 28, 2024, 2 pages.
Final Office Action for U.S. Appl. No. 17/002,860 date mailed Aug. 5, 2024.
Non Final Office Action for U.S. Appl. No. 17/691,050 date mailed Aug. 14, 2024.
Non Final Office Action for U.S. Appl. No. 17/005,825 date mailed Nov. 5, 2024.
Final Office Action for U.S. Appl. No. 17/674,397 date mailed Oct. 9, 2024.
Non Final Office Action for U.S. Appl. No. 17/980,149 date mailed Nov. 5, 2024.
Non Final Office Action for U.S. Appl. No. 16/797,301 date mailed Sep. 25, 2024.

ANTI-CD38 ANTIBODIES FOR TREATMENT OF ACUTE MYELOID LEUKEMIA

RELATED APPLICATIONS

This application is a continuation of U.S. application Ser. No. 14/956,890, filed Dec. 2, 2015, which claims the benefit of U.S. Provisional Application No. 62/087,442, filed on Dec. 4, 2014. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
   a) File name: 0148_2018_054 SequenceListing.txt; created Aug. 27, 2020, 21 KB in size.

FIELD OF THE INVENTION

The present invention relates to methods of treatment of acute myeloid leukemia with anti-CD38 antibodies.

BACKGROUND OF THE INVENTION

CD38 is a type II membrane protein with ADP ribosyl cyclase activity, catalyzing formation of second messengers cyclic ADP-ribose (cADPR) and nicotinic acid adenine dinucleotide phosphate (NAADP) from NAD and NADP, respectively. CD38 mediates calcium mobilization and regulates intracellular NAD levels, and is implicated having role in various physiological functions (Funaro et al., J Immunology 145:2390-6, 1990; Terhorst et al., Cell 771-80, 1981; Guse et al., Nature 398:70-3, 1999; Adriouch et al., 14:1284-92, 2012; Chiarugi et al., Nature Reviews 12:741-52, 2012; Wei et al., WJBC 5:58-67, 2014)

Acute myeloid leukemia (AML) is a heterogeneous hematologic disorder characterized by clonal expansion of myeloid blasts in bone marrow, peripheral blood and other tissues. Despite recent progress, current treatment of AML remains unsatisfactory with a 5-year relapse-free survival rate lower than 30%.

Therefore, there remains a need for effective treatments for AML.

SUMMARY OF THE INVENTION

One embodiment of the invention is a method of treating a subject having acute myeloid leukemia (AML), comprising administering to the subject in need thereof an anti-CD38 antibody for a time sufficient to treat AML.

One embodiment of the invention is a method of treating a subject having acute myeloid leukemia (AML), comprising administering to the subject in need thereof an anti-CD38 antibody that competes for binding to CD38 with an antibody comprising a heavy chain variable region (VH) of SEQ ID NO: 4 and a light chain variable region (VL) of SEQ ID NO: 5 for a time sufficient to treat AML.

DETAILED DESCRIPTION OF THE INVENTION

Figure 1A:
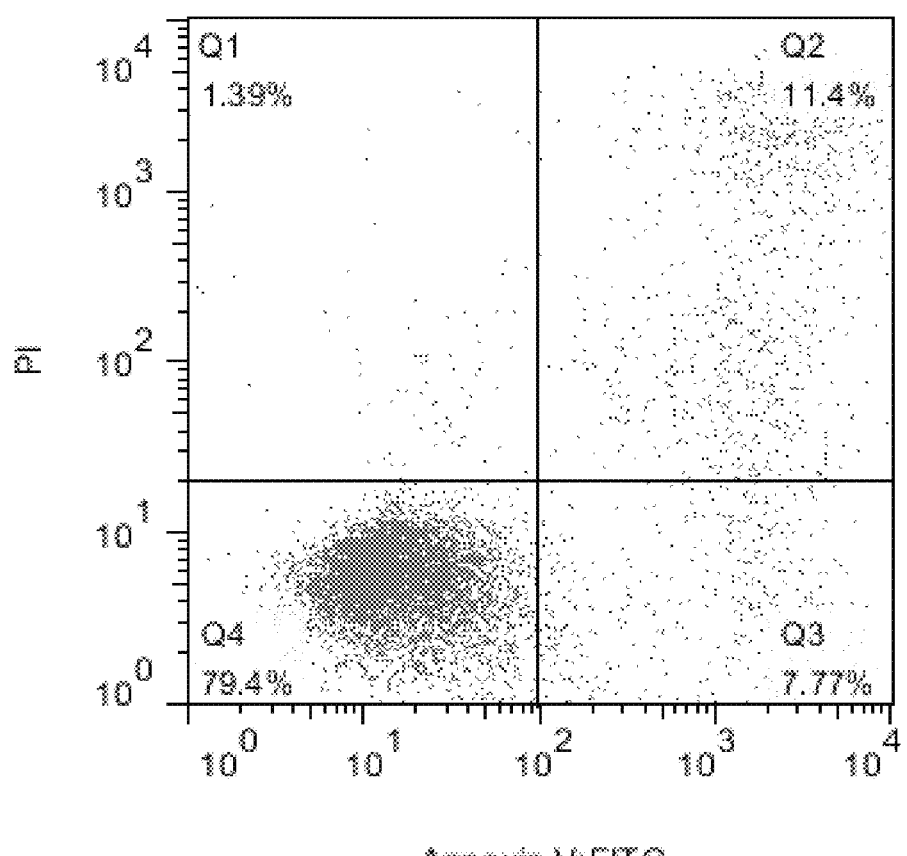
FIG. 1A shows daratumumab-induced apoptosis in the absence of crosslinking in NB-4 AML cell line. PI: propidium iodide.

"CD38" refers to the human CD38 protein (synonyms: ADP-ribosyl cyclase 1, cADPr hydrolase 1, cyclic ADP-ribose hydrolase 1). Human CD38 has an amino acid sequence shown in SEQ ID NO: 1

"Antibodies" as used herein is meant in a broad sense and includes immunoglobulin molecules including monoclonal antibodies including murine, human, human-adapted, humanized and chimeric monoclonal antibodies, antibody fragments, bispecific or multispecific antibodies, dimeric, tetrameric or multimeric antibodies, and single chain antibodies.

Immunoglobulins may be assigned to five major classes, namely IgA, IgD, IgE, IgG and IgM, depending on the heavy chain constant domain amino acid sequence. IgA and IgG are further sub-classified as the isotypes IgA$_1$, IgA$_2$, IgG$_1$, IgG$_2$, IgG$_3$ and IgG$_4$. Antibody light chains of any vertebrate species may be assigned to one of two clearly distinct types, namely kappa (κ) and lambda (λ), based on the amino acid sequences of their constant domains.

"Antibody fragments" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include a Fab fragment, a monovalent fragment consisting of the VL, VH, CL and CH1 domains; a F(ab)$_2$ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a domain antibody (dAb) fragment (Ward et al (1989) Nature 341:544-546), which consists of a VH domain. VH and VL domains may be engineered and linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in PCT Intl. Publ. Nos. WO1998/44001, WO1988/01649, WO1994/13804, and WO1992/01047. These antibody fragments are obtained using well known techniques known to those of skill in the art, and the fragments are screened for utility in the same manner as are full length antibodies.

The phrase "isolated antibody" refers to an antibody or antibody fragment that is substantially free of other antibodies having different antigenic specificities (e.g., an isolated antibody specifically binding CD38 is substantially free of antibodies that specifically bind antigens other than human CD38). An isolated antibody that specifically binds CD38, however, may have cross-reactivity to other antigens, such as orthologs of human CD38, such as *Macaca fascicularis* (cynomolgus) CD38. Moreover, an isolated antibody may be substantially free of other cellular material and/or chemicals.

An antibody variable region consists of a "framework" region interrupted by three "antigen binding sites". The antigen binding sites are defined using various terms: Complementarity Determining Regions (CDRs), three in the VH (HCDR1, HCDR2, HCDR3) and three in the VL (LCDR1, LCDR2, LCDR3) are based on sequence variability (Wu and Kabat J Exp Med 132:211-50, 1970; Kabat et al Sequences of Proteins of Immunological Interest, 5th Ed. Public Health Service, National Institutes of Health, Bethesda, Md., 1991), "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro, Mol Recognit 17:132-43, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003.

"Chothia residues" as used herein are the antibody VL and VH residues numbered according to Al-Lazikani (Al-Lazikani et al., J Mol Biol 273:927-48, 1997).

"Framework" or "framework sequences" are the remaining sequences of a variable region other than those defined to be antigen binding sites. Because the antigen binding sites may be defined by various terms as described above, the exact amino acid sequence of a framework depends on how the antigen-binding site was defined.

"Humanized antibody" refers to an antibody in which the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

"Human-adapted" antibodies or "human framework adapted (HFA)" antibodies refers to humanized antibodies adapted according to methods described in U.S. Pat. Publ. No. US2009/0118127. Human-adapted antibodies are humanized by selecting the acceptor human frameworks based on the maximum CDR and FR similarities, length compatibilities and sequence similarities of CDR1 and CDR2 loops and a portion of light chain CDR3 loops.

"Human antibody" refers to an antibody having heavy and light chain variable regions in which both the framework and the antigen binding sites are derived from sequences of human origin. If the antibody contains a constant region, the constant region also is derived from sequences of human origin.

A human antibody comprises heavy or light chain variable regions that are "derived from" sequences of human origin wherein the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. A "human antibody" may contain amino acid differences when compared to the human germline or rearranged immunoglobulin sequences due to for example naturally occurring somatic mutations or intentional introduction of substitutions in the framework or antigen binding sites. Typically, a human antibody is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, "human antibody" may contain consensus framework sequences derived from human framework sequence analyses, for example as described in Knappik et al., J Mol Biol 296:57-86, 2000), or synthetic HCDR3 incorporated into human immunoglobulin gene libraries displayed on phage, for example as described in Shi et al., J Mol Biol 397:385-96, 2010 and Intl. Pat. Publ. No. WO2009/085462). Antibodies in which antigen binding sites are derived from a non-human species are not included in the definition of human antibody.

Isolated humanized antibodies may be synthetic. Human antibodies may be generated using systems such as phage display incorporating synthetic CDRs and/or synthetic frameworks, or can be subjected to in vitro mutagenesis to improve antibody properties.

"Recombinant antibody" as used herein includes all antibodies that are prepared, expressed, created or isolated by recombinant means, such as antibodies isolated from an animal, for example a mouse or a rat, that is transgenic or transchromosomal for human immunoglobulin genes or a hybridoma prepared therefrom (described further below), antibodies isolated from a host cell transformed to express the antibody, antibodies isolated from a recombinant, combinatorial antibody library, and antibodies prepared, expressed, created or isolated by any other means that involve splicing of human immunoglobulin gene sequences to other DNA sequences, or antibodies that are generated in vitro using for example Fab arm exchange to generate bispecific antibodies.

"Monoclonal antibody" as used herein refers to a preparation of antibody molecules of single molecular composition. A monoclonal antibody composition displays a single binding specificity and affinity for a particular epitope, or in a case of a bispecific monoclonal antibody, a dual binding specificity to two distinct epitopes.

"Epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. Epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Variant" as used herein refers to a polypeptide or a polynucleotide that differs from a reference polypeptide or a reference polynucleotide by one or more modifications for example, substitutions, insertions or deletions.

"Synergy", "synergism" or "synergistic" mean more than the expected additive effect of a combination.

The term "in combination with" as used herein means that two or more therapeutics can be administered to a subject together in a mixture, concurrently as single agents or sequentially as single agents in any order.

"Treat" or "treatment" refers to therapeutic treatment wherein the object is to slow down (lessen) an undesired physiological change or disease, such as the development, expansion or spread of tumor or tumor cells, or to provide a beneficial or desired clinical outcome during treatment. Beneficial or desired clinical outcomes include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" may also mean prolonging survival as compared to expected survival if a subject was not receiving treatment. Those in need of treatment include those subjects already with the undesired physiological change or disease as well as those subjects prone to have the physiological change or disease.

"Inhibits growth" (e.g. referring to cells, such as tumor cells) refers to a measurable decrease in the cell growth in vitro or in vivo when contacted with a therapeutic or a combination of therapeutics or drugs when compared to the growth of the same cells grown in appropriate control conditions well known to the skilled in the art. Inhibition of growth of a cell in vitro or in vivo may be at least about 10%, 20%, 30%, 40%, 50%, 60%, 70%, 80%, 90%, 99%, or 100%. Inhibition of cell growth may occur by a variety of mechanisms, for example by antibody-dependent cell-mediated cytotoxicity (ADCC), antibody-dependent cellular phagocytosis (ADCP), complement dependent cytotoxicity (CDC), apoptosis, necrosis, inhibition of CD38 enzymatic activity, or by inhibition of cell proliferation.

A "therapeutically effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective therapeutic or combination of therapeutics include, for example, improved well-being of the patient, reduction of a tumor burden, arrested or slowed growth of a tumor, and/or absence of metastasis of cancer cells to other locations in the body.

One embodiment of the invention described herein, and in some embodiments of each and every one of the numbered embodiments listed below, is a method of treating a subject having acute myeloid leukemia (AML), comprising administering to the subject in need thereof an anti-CD38 antibody for a time sufficient to treat AML.

Another embodiment of the invention described herein, and in some embodiments of each and every one of the numbered embodiments listed below, is a method of treating a subject having acute myeloid leukemia (AML), comprising administering to the subject in need thereof an anti-CD38 antibody that competes for binding to CD38 with an antibody comprising a heavy chain variable region (VH) of SEQ ID NO: 4 and a light chain variable region (VL) of SEQ ID NO: 5 for a time sufficient to treat AML.

Another embodiment of the invention described herein, and in some embodiments of each and every one of the numbered embodiments listed below, is a method of treating a subject having acute myeloid leukemia (AML), comprising administering to the subject in need thereof an anti-CD38 antibody that binds to the region SKRNIQFSCKNIYR (SEQ ID NO: 2) and the region EKVQTLEAWVIHGG (SEQ ID NO: 3) of human CD38 (SEQ ID NO: 1) for a time sufficient to treat AML.

An anti-CD38 antibody binds to the region SKRNIQFSCKNIYR (SEQ ID NO: 2) and the region EKVQTLEAWVIHGG (SEQ ID NO: 3) of human CD38 (SEQ ID NO: 1) when the antibody binds at least 1, 2, 3, 4, 5, 6, 7, 8, 9, 10, 11, 12, 13 or 14 residues within SEQ ID NO: 2 and SEQ ID NO: 3. In some embodiments disclosed herein, including the numbered embodiments listed below, the anti-CD38 antibody binds at least one amino acid in the region SKRNIQFSCKNIYR (SEQ ID NO: 2) and at least one amino acid in the region EKVQTLEAWVIHGG (SEQ ID NO: 3) of human CD38 (SEQ ID NO: 1). In some embodiments disclosed herein, including in the numbered embodiments listed below, the anti-CD38 antibody binds at least two amino acids in the region SKRNIQFSCKNIYR (SEQ ID NO: 2) and at least two amino acids in the region EKVQTLEAWVIHGG (SEQ ID NO: 3) of human CD38 (SEQ ID NO: 1). In some embodiments disclosed herein, including in the numbered embodiments listed below, the anti-CD38 antibody binds at least three amino acids in the region SKRNIQFSCKNIYR (SEQ ID NO: 2) and at least three amino acids in the region EKVQTLEAWVIHGG (SEQ ID NO: 3) of human CD38 (SEQ ID NO: 1). In some embodiments disclosed herein, including in the numbered embodiments listed below, the anti-CD38 antibody binds at least residues KRN in the region SKRNIQFSCKNIYR (SEQ ID NO: 2) and at least residues VQLT (SEQ ID NO: 14) in the region EKVQTLEAWVIHGG (SEQ ID NO: 3) of human CD38 (SEQ ID NO: 1).

An exemplary antibody that binds to the region SKRNIQFSCKNIYR (SEQ ID NO: 2) and the region EKVQTLEAWVIHGG (SEQ ID NO: 3) of human CD38 (SEQ ID NO: 1) or minimally to residues KRN and VQLT (SEQ ID NO: 14) as shown above is daratumumab (see Intl. Pat. Publ. No. WO2006/0998647). Daratumumab comprises the VH and the VL amino acid sequences shown in SEQ ID NO: 4 and 5, respectively, heavy chain CDRs HCDR1, HCDR2 and HCDR3 of SEQ ID NOs: 6, 7 and 8, respectively, and light chain CDRs LCDR1, LCDR2 and LCDR3 of SEQ ID NOs: 9, 10 and 11, respectively, and is of IgG1/κ subtype. Daratumumab heavy chain amino acid sequence is shown in SEQ ID NO: 12 and light chain amino acid sequence shown in SEQ ID NO: 13.

Another embodiment of the invention described herein, and in some embodiments of each and every one of the numbered embodiments listed below, is a method of treating a subject having acute myeloid leukemia (AML), comprising administering to the subject in need thereof an anti-CD38 antibody comprising a heavy chain variable region (VH) and a light chain variable region (VL) of SEQ ID NOs: 4 and 5, respectively, for a time sufficient to treat AML.

Another embodiment of the invention described herein, and in some embodiments of each and every one of the numbered embodiments listed below, is a method of treating a subject having acute myeloid leukemia (AML), comprising administering to the subject in need thereof an anti-CD38 antibody comprising heavy chain CDRs HCDR1, HCDR2 and HCDR3 of SEQ ID NOs: 6, 7 and 8, respectively, and light chain CDRs LCDR1, LCDR2 and LCDR3 of SEQ ID NOs: 9, 10 and 11, respectively, for a time sufficient to treat AML.

```
                                          SEQ ID NO: 1
MANCEFSPVSGDKPCCRLSRRAQLCLGVSILVLILVVVLAVVVPRWRQQW

SGPGTTKRFPETVLARCVKYTEIHPEMRHVDCQSVWDAFKGAFISKHPCN

ITEEDYQPLMKLGTQTVPCNKILLWSRIKDLAHQFTQVQRDMFTLEDTLL

GYLADDLTWCGEFNTSKINYQSCPDWRKDCSNNPVSVFWKTVSRRFAEAA

CDVVHVMLNGSRSKIFDKNSTFGSVEVHNLQPEKVQTLEAWVIHGGREDS

RDLCQDPTIKELESIISKRNIQFSCKNIYRPDKFLQCVKNPEDSSCTSEI

SEQ ID NO: 2
SKRNIQFSCKNIYR

SEQ ID NO: 3
EKVQTLEAWVIHGG

SEQ ID NO: 4
EVQLLESGGGLVQPGGSLRLSCAVSGFTFNSFAMSWVRQAPGKGLEWVSA

ISGSGGGTYYADSVKGRFTISRDNSKNTLYLQMNSLRAEDTAVYFCAKDK

ILWFGEPVFDYWGQGTLVTVSS

SEQ ID NO: 5
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPTFGQ

GTKVEIK

SEQ ID NO: 6
SFAMS

SEQ ID NO: 7
AISGSGGGTYYADSVKG

SEQ ID NO: 8
DKILWFGEPVFDY

SEQ ID NO: 9
RASQSVSSYLA

SEQ ID NO: 10
DASNRAT

SEQ ID NO: 11
QQRSNWPPTF

SEQ ID NO: 12
EVQLLESGGGLVQPGGSLRLSCAVSGFTFNSFAMSWVRQAPGKGLEWVSA

ISGSGGGTYYADSVKGRFTISRDNSKNTLYLQMNSLRAEDTAVYFCAKDK

ILWFGEPVFDYWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFPP
```

```
KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK

SEQ ID NO: 13
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NO: 14
VQLT
```

Antibodies may be evaluated for their competition with daratumumab having VH of SEQ ID NO: 4 and VL of SEQ ID NO: 5 for binding to CD38 using well known in vitro methods. In an exemplary method, CHO cells recombinantly expressing CD38 may be incubated with unlabeled daratumumab for 15 min at 4° C., followed by incubation with an excess of fluorescently labeled test antibody for 45 min at 4° C. After washing in PB SB SA, fluorescence may be measured by flow cytometry using standard methods. In another exemplary method, extracellular portion of human CD38 may be coated on the surface of an ELISA plate. Excess of unlabelled daratumumab may be added for about 15 minutes and subsequently biotinylated test antibodies may be added. After washes in PBS/Tween, binding of the test biotinylated antibody may be detected using horseradish peroxidase (HRP)-conjugated streptavidine and the signal detected using standard methods. It is readily apparent that in the competition assays, daratumumab may be labelled and the test antibody unlabeled. The test antibody competes with daratumumab when daratumumab inhibits binding of the test antibody, or the test antibody inhibits binding of daratumumab by 20%, 30%, 40%, 50%, 60%, 70%, 80%, 85%, 90%, 95% or 100%. The epitope of the test antibody may further be defined for example by peptide mapping or hydrogen/deuterium protection assays using known methods, or by crystal structure determination.

Antibodies binding to the same region on CD38 as daratumumab may be generated for example by immunizing mice with peptides having the amino acid sequences shown in SEQ ID NOs: 2 and 3 using standard methods and as described herein. Antibodies may be further evaluated for example by assaying competition between daratumumab and a test antibody for binding to CD38 using well known in vitro methods and as described herein.

Other exemplary anti-CD38 antibodies that may be used in any embodiment of the invention described herein, and in some embodiments of each and every one of the numbered embodiments listed below, are:

mAb003 comprising the VH and VL sequences of SEQ ID NOs: 15 and 16, respectively and described in U.S. Pat. No. 7,829,673. The VH and the VL of mAb003 may be expressed as IgG1/κ.

```
                                           SEQ ID NO: 15
QVQLVQSGAEVKKPGSSVKVSCKASGGTFSSYAFSWVRQAPGQGLEWMGR

VIPFLGIANSAQKFQGRVTITADKSTSTAYMDLSSLRSEDTAVYYCARDD

IAALGPFDYWGQGTLVTVSSAS

SEQ ID NO: 16
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPRTFGQ

GTKVEIK;
``` mAb024 comprising the VH and VL sequences of SEQ ID NOs: 17 and 18, respectively, described in U.S. Pat. No. 7,829,673. The VH and the VL of mAb024 may be expressed as IgG1/κ.

```
                                           SEQ ID NO: 17
EVQLVQSGAEVKKPGESLKISCKGSGYSFSNYWIGWVRQMPGKGLEWMG

IIYPHDSDARYSPSFQGQVTFSADKSISTAYLQWSSLKASDTAMYYCAR

HVGWGSRYWYFDLWGRGTLVTVSS

SEQ ID NO: 18
EIVLTQSPATLSLSPGERATLSCRASQSVSSYLAWYQQKPGQAPGLLIY

DASNRASGIPARFSGSGSGTDFTLTISSLEPEDFAVYYCQQRSNWPLTF

GGGTKVEIK
```

MOR-202 (MOR-03087) comprising the VH and VL sequences of SEQ ID NOs: 19 and 20, respectively, described in U.S. Pat. No. 8,088,896. The VH and the VL of MOR-202 may be expressed as IgG1/κ.

```
                                           SEQ ID NO: 19
QVQLVESGGGLVQPGGSLRLSCAASGFTFSSYYMNWVRQAPGKGLEWVSG

ISGDPSNTYYADSVKGRFTISRDNSKNTLYLQMNSLRAEDTAVYYCARDL

PLVYTGFAYWGQGTLVTVSS

SEQ ID NO: 20
DIELTQPPSVSVAPGQTARISCSGDNLRHYYVYWYQQKPGQAPVLVIYGD

SKRPSGIPERFSGSNSGNTATLTISGTQAEDEADYYCQTYTGGASLVFGG

GTKLTVLGQ;
```

Isatuximab; comprising the VH and VL sequences of SEQ ID NOs: 21 and 22, respectively, described in U.S. Pat. No. 8,153,765. The VH and the VL of Isatuximab may be expressed as IgG1/κ.

```
SEQ ID NO 21:
QVQLVQSGAEVAKPGTSVKLSCKASGYTFTDYWMQWVKQRPGQGLEWIGT

IYPGDGDTGYAQKFQGKATLTADKSSKTVYMHLSSLASEDSAVYYCARGD

YYGSNSLDYWGQGTSVTVSS

SEQ ID NO: 22:
DIVMTQSHLSMSTSLGDPVSITCKASQDVSTVVAWYQQKPGQSPRRLIYS

ASYRYIGVPDRFTGSGAGTDFTFTISSVQAEDLAVYYCQQHYSPPYTFGG

GTKLEIK.
```

Other exemplary anti-CD38 antibodies that may be used in the methods of the invention include those described in Int. Pat. Publ. No. WO05/103083, Intl. Pat. Publ. No.

WO06/125640, Intl. Pat. Publ. No. WO07/042309, Intl. Pat. Publ. No. WO08/047242 or Intl. Pat. Publ. No. WO14/178820.

Another embodiment of the invention described herein, and in some embodiments of each and every one of the numbered embodiments listed below, is a method of treating a subject having acute myeloid leukemia (AML), comprising administering to the subject in need thereof an anti-CD38 antibody comprising a heavy chain variable region (VH) and a light chain variable region (VL) of SEQ ID NOs: 15 and 16, respectively, for a time sufficient to treat AML.

Another embodiment of the invention described herein, and in some embodiments of each and every one of the numbered embodiments listed below, is a method of treating a subject having acute myeloid leukemia (AML), comprising administering to the subject in need thereof an anti-CD38 antibody comprising a heavy chain variable region (VH) and a light chain variable region (VL) of SEQ ID NOs: 17 and 18, respectively, for a time sufficient to treat AML.

Another embodiment of the invention described herein, and in some embodiments of each and every one of the numbered embodiments listed below, is a method of treating a subject having acute myeloid leukemia (AML), comprising administering to the subject in need thereof an anti-CD38 antibody comprising a heavy chain variable region (VH) and a light chain variable region (VL) of SEQ ID NOs: 19 and 20, respectively, for a time sufficient to treat AML.

Another embodiment of the invention described herein, and in some embodiments of each and every one of the numbered embodiments listed below, is a method of treating a subject having acute myeloid leukemia (AML), comprising administering to the subject in need thereof an anti-CD38 antibody comprising a heavy chain variable region (VH) and a light chain variable region (VL) of SEQ ID NOs: 21 and 22, respectively, for a time sufficient to treat AML.

The Fc portion of the antibody may mediate antibody effector functions such as antibody-dependent cell-mediated cytotoxicity (ADCC), antibody-dependent cellular phagocytosis (ADCP) or complement dependent cytotoxicity (CDC). Such function may be mediated by binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of target cells, for example CD38-expressing cells. Human IgG isotypes IgG1, IgG2, IgG3 and IgG4 exhibit differential capacity for effector functions. ADCC may be mediated by IgG1 and IgG3, ADCP may be mediated by IgG1, IgG2, IgG3 and IgG4, and CDC may be mediated by IgG1 and IgG3.

In the methods described herein, and in some embodiments of each and every one of the numbered embodiments listed below, the anti-CD38 antibody is of IgG1, IgG2, IgG3 or IgG4 isotype.

In the methods described herein, and in some embodiments of each and every one of the numbered embodiments listed below, the anti-CD38 antibody induces killing of AML cells that express CD38 by apoptosis.

The anti-CD38 antibodies used in the methods described herein, and in some embodiments of each and every one of the numbered embodiments listed below, may induce killing of AML cells by apoptosis. Methods for evaluating apoptosis are well known, and include for example annexin IV staining using standard methods. The anti-CD38 antibodies used in the methods of the invention may induce apoptosis in about 10%, 15%, 20%, 25%, 30%, 35%, 40%, 45%, 50%, 55%, 60%, 65%, 70%, 75%, 80%, 85%, 90%, 95% or 100% of cells.

In the methods described herein, and in some embodiments of each and every one of the numbered embodiments listed below, the anti-CD38 induces killing of AML cells that express CD38 by ADCC.

In the methods described herein, and in some embodiments of each and every one of the numbered embodiments listed below, the anti-CD38 induces killing of AML cells that express CD38 by CDC.

In the methods described herein, and in some embodiments of each and every one of the numbered embodiments listed below, the anti-CD38 antibody induces killing of AML cells that express CD38 by ADCP.

In the methods described herein, and in some embodiments of each and every one of the numbered embodiments listed below, the anti-CD38 antibody induces killing of AML cells that express CD38 by ADCC and CDC.

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIa, whereas monocytes express FcγRI, FcγRII and FcvRIIIa. Death of the antibody-coated target cell, such as CD38-expressing cells, occurs as a result of effector cell activity through the secretion of membrane pore-forming proteins and proteases. To assess ADCC activity of an anti-CD38 antibody, the antibody may be added to CD38-expressing cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Exemplary effector cells for such assays include peripheral blood mononuclear cells (PBMC) and NK cells. Exemplary target cells include Daudi cells (ATCC® CCL-213™) or B cell leukemia or lymphoma tumor cells expressing CD38. In an exemplary assay, target cells are labeled with 20 µCi of $^{51}$Cr for 2 hours and washed extensively. Cell concentration of the target cells may be adjusted to $1 \times 10^6$ cells/ml, and anti-CD38 antibodies at various concentrations are added. Assays are started by adding Daudi cells at an effector:target cell ratio of 40:1. After incubation for 3 hr at 37° C. assays are stopped by centrifugation, and $^{51}$Cr release from lysed cells are measured in a scintillation counter. Percentage of cellular cytotoxicity may be calculated as % maximal lysis which may be induced by adding 3% perchloric acid to target cells. Anti-CD38 antibodies used in the methods of the invention may induce ADCC by about 20%, 25%, 30%, 35%, 40%, 45%, 50%, 55%, 60%, 65%, 70%, 75%, 80%, 85%, 90%, 95% or 100% of control (cell lysis induced by 3% perchloric acid).

"Antibody-dependent cellular phagocytosis" ("ADCP") refers to a mechanism of elimination of antibody-coated target cells by internalization by phagocytic cells, such as macrophages or dendritic cells. ADCP may be evaluated by using monocyte-derived macrophages as effector cells and Daudi cells (ATCC® CCL-213™) or B cell leukemia or lymphoma tumor cells expressing CD38 as target cells engineered to express GFP or other labeled molecule. Effector:target cell ratio may be for example 4:1. Effector cells may be incubated with target cells for 4 hours with or without anti-CD38 antibody. After incubation, cells may be detached using accutase. Macrophages may be identified with anti-CD11b and anti-CD14 antibodies coupled to a fluorescent label, and percent phagocytosis may be determined based on % GFP fluorescent in the CD11$^+$CD14$^+$ macrophages using standard methods. Anti-CD38 antibodies used in the methods of the invention may induce ADCP by about 20%, 25%, 30%, 35%, 40%, 45%, 50%, 55%, 60%, 65%, 70%, 75%, 80%, 85%, 90%, 95% or 100%.

"Complement-dependent cytotoxicity", or "CDC", refers to a mechanism for inducing cell death in which an Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes. CDC of CD38-expressing cells may be measured for example by plating Daudi cells at $1\times10^5$ cells/well (50 µl/well) in RPMI-B (RPMI supplemented with 1% BSA), adding 50 µl anti-CD38 antibodies to the wells at final concentration between 0-100 µg/ml, incubating the reaction for 15 min at room temperature, adding 11 µl of pooled human serum to the wells, and incubating the reaction for 45 min at 37° C. Percentage (%) lysed cells may be detected as % propidium iodide stained cells in FACS assay using standard methods. Anti-CD38 antibodies used in the methods of the invention may induce CDC by about 20%, 25%, 30%, 35%, 40%, 45%, 50%, 55%, 60%, 65%, 70%, 75%, 80%, 85%, 90%, 95% or 100%.

The ability of monoclonal antibodies to induce ADCC may be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs may be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α 1,6-fucosyltrasferase (FUT8) gene (Mori et al., Biotechnol Bioeng 88:901-908, 2004), or coexpression of β-1,4-N-acetylglucosaminyltransferase III and Golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008). ADCC elicited by anti-CD38 antibodies used in the methods of the invention, and in some embodiments of each and every one of the numbered embodiments listed below, may also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

In some methods described herein, and in some embodiments of each and every one of the numbered embodiments listed below, the anti-CD38 antibodies comprise a substitution in the antibody Fc.

In some methods described herein, and in some embodiments of each and every one of the numbered embodiments listed below, the anti-CD38 antibodies comprise a substitution in the antibody Fc at amino acid positions 256, 290, 298, 312, 356, 330, 333, 334, 360, 378 or 430 (residue numbering according to the EU index).

In some methods described herein, and in some embodiments of each and every one of the numbered embodiments listed below, the anti-CD38 antibody has a biantennary glycan structure with fucose content of about between 0% to about 15%, for example 15%, 14%, 13%, 12%, 11% 10%, 9%, 8%, 7%, 6%, 5%, 4%, 3%, 2%, 1% or 0%.

In some methods described herein, and in some embodiments of each and every one of the numbered embodiments listed below, the anti-CD38 antibody has a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%

Substitutions in the Fc and reduced fucose content may enhance the ADCC activity of the anti-CD38 antibody.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Intl. Pat. Publ. No. WO2008/077546; 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS) or 5) separation of the mAb oligosaccharides from the mAb protein by specific enzymatic deglycosylation with PNGase F at Asn 297. The oligosaccharides released can be labeled with a fluorophore, separated and identified by various complementary techniques which allow: fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosacharride forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" as used in the application refers to antibodies with fucose content of about 0%-15%.

"Normal fucose" or "normal fucose content" as used herein refers to antibodies with fucose content of about over 50%, typically about over 60%, 70%, 80% or over 85%.

The anti-CD38 antibodies used in the methods described herein, and in some embodiments of each and every one of the numbered embodiments listed below, may induce killing of AML cells by modulation of CD38 enzymatic activity. CD38 is a multifunctional ectoenzme with ADP-ribosyl cyclase activity catalyzing the formation of cyclic ADP-ribose (cADPR) and ADPR from NAD'. CD38 also catalyzes the exchange of the nicotinamide group of NADP$^+$ with nicotinic acid under acidic conditions, to yield NAADP$^+$ (nicotinic acid-adenine dinucleotide phosphate). Modulation of the enzymatic activity of human CD38 with anti-CD38 antibodies used in the methods of the invention may be measured in an assay described in Graeff et al., J. Biol. Chem. 269, 30260-30267 (1994). For example, substrate NGD$^+$ may be incubated with CD38, and the modulation of the production of cyclic GDP-ribose (cGDPR) may be monitored spectrophotometrically at excitation at 340 nM and emission at 410 nM at different time points after addition of the antibody at various concentrations. Inhibition of the synthesis of cADPR can be determined according to the HPLC method described in Munshi et al., J. Biol. Chem. 275, 21566-21571 (2000). The anti-CD38 antibodies used in the methods of the invention described herein, and in some embodiments of each and every one of the numbered embodiments listed below, may inhibit CD38 enzymatic activity by at least about 20%, 25%, 30%, 35%, 40%, 45%, 50%, 55%, 60%, 65%, 70%, 75%, 80%, 85%, 90%, 95% or 100%.

In some methods of the invention described herein, and in some embodiments of each and every one of the numbered embodiments listed below, the anti-CD38 antibody comprises the heavy chain complementarity determining regions (HCDR) 1 (HCDR1), 2 (HCDR2) and 3 (HCDR3) sequences of SEQ ID NOs: 6, 7 and 8, respectively.

In some methods of the invention described herein, and in some embodiments of each and every one of the numbered embodiments listed below, the anti-CD38 antibody comprises the light chain complementarity determining regions (LCDR) 1 (LCDR1), 2 (LCDR2) and 3 (LCDR3) sequences of SEQ ID NOs: 9, 10 and 11, respectively.

In some methods of the invention described herein, and in some embodiments of each and every one of the numbered embodiments listed below, the anti-CD38 antibody comprises the heavy chain complementarity determining regions (HCDR) 1 (HCDR1), 2 (HCDR2) and 3 (HCDR3) sequences of SEQ ID NOs: 6, 7 and 8, respectively, and the light chain complementarity determining regions (LCDR) 1 (LCDR1), 2 (LCDR2) and 3 (LCDR3) sequences of SEQ ID NOs: 9, 10 and 11, respectively.

In some methods of the invention described herein, and in some embodiments of each and every one of the numbered embodiments listed below, the anti-CD38 antibody comprises the heavy chain variable region (VH) of SEQ ID NO: 4 and the light chain variable region (VL) of SEQ ID NO: 5.

In some methods of the invention described herein, and in some embodiments of each and every one of the numbered embodiments listed below, the anti-CD38 antibody comprises a heavy chain of SEQ ID NO: 12 and a light chain of SEQ ID NO: 13.

In some methods of the invention described herein, and in some embodiments of each and every one of the numbered embodiments listed below, the anti-CD38 antibody comprises a heavy chain comprising an amino acid sequence that is 95%, 96%, 97%, 98% or 99% identical to that of SEQ ID NO: 12 and a light chain comprising an amino acid sequence that is 95%, 96%, 97%, 98% or 99% identical to that of SEQ ID NO: 13.

Antibodies that are substantially identical to the antibody comprising the heavy chain of SEQ ID NO: 12 and the light chain of SEQ ID NO: 13 may be used in the methods of the invention. "Substantially identical" as used herein means that the two antibody heavy chain or light chain amino acid sequences being compared are identical or have "insubstantial differences". Insubstantial differences are substitutions of 1, 2, 3, 4, 5, 6, 7, 8, 9, 10, 11, 12, 13, 14, or 15 amino acids in an antibody heavy chain or light chain that do not adversely affect antibody properties. Percent identity can be determined for example by pairwise alignment using the default settings of the AlignX module of Vector NTI v.9.0.0 (Invitrogen, Carlsbad, CA). The protein sequences of the present invention may be used as a query sequence to perform a search against public or patent databases to, for example, identify related sequences. Exemplary programs used to perform such searches are the XBLAST or BLASTP programs (http_//www_ncbi_nlm/nih_gov), or the GenomeQuest™ (GenomeQuest, Westborough, MA) suite using the default settings. Exemplary substitutions that may be made to the anti-CD38 antibodies used in the methods of the invention are for example conservative substitutions with an amino acid having similar charge, hydrophobic, or stereochemical characteristics. Conservative substitutions may also be made to improve antibody properties, for example stability or affinity, or to improve antibody effector functions. 1, 2, 3, 4, 5, 6, 7, 8, 9, 10, 11, 12, 13, 14, or 15 amino acid substitutions may be made for example to the heavy or the light chain of the anti-CD38 antibody. Furthermore, any native residue in the heavy or light chain may also be substituted with alanine, as has been previously described for alanine scanning mutagenesis (MacLennan et al., Acta Physiol Scand Suppl 643:55-67, 1998; Sasaki et al., Adv Biophys 35:1-24, 1998). Desired amino acid substitutions may be determined by those skilled in the art at the time such substitutions are desired. Amino acid substitutions may be done for example by PCR mutagenesis (U.S. Pat. No. 4,683,195). Libraries of variants may be generated using well known methods, for example using random (NNK) or non-random codons, for example DVK codons, which encode 11 amino acids (Ala, Cys, Asp, Glu, Gly, Lys, Asn, Arg, Ser, Tyr, Trp) and screening the libraries for variants with desired properties. The generated variants may be tested for their binding to CD38 and their ability to induce apoptosis or modulate CD38 enzymatic activity using methods described herein.

In the methods described herein, and in some embodiments of each and every one of the numbered embodiments listed below, the anti-CD38 antibody may bind human CD38 with a range of affinities ($K_D$). In one embodiment according to the invention, and in some embodiments of each and every one of the numbered embodiments listed below, the anti-CD38 antibody binds to CD38 with a $K_D$ equal to or less than about $1 \times 10^{-8}$ M, for example $5 \times 10^{-9}$ M, $1 \times 10^{-9}$ M, $5 \times 10^{-10}$ M, $1 \times 10^{-10}$ M, $5 \times 10^{-11}$ M, $1 \times 10^{-11}$ M, $5 \times 10^{-12}$ M, $1 \times 10^{-12}$ M, $5 \times 10^{-13}$ M, $1 \times 10^{-13}$ M, $5 \times 10^{-14}$ M, $1 \times 10^{-14}$ M or $5 \times 10^{-15}$ M, or any range or value therein, as determined by surface plasmon resonance or the Kinexa method, as practiced by those of skill in the art. One exemplary affinity is equal to or less than $1 \times 10^{-8}$ M. Another exemplary affinity is equal to or less than $1 \times 10^{-9}$ M.

In some embodiments, and in some embodiments of each and every one of the numbered embodiments listed below, the anti-CD38 antibody is a bispecific antibody. The VL and/or the VH regions of existing anti-CD38 antibodies or the VL and VH regions identified de novo as described herein may be engineered into bispecific full length antibodies. Such bispecific antibodies may be made by modulating the CH3 interactions in antibody Fc to form bispecific antibodies using technologies such as those described in U.S. Pat. No. 7,695,936; Int. Pat. Publ. No. WO04/111233; U.S. Pat. Publ. No. US2010/0015133; U.S. Pat. Publ. No. US2007/0287170; Int. Pat. Publ. No. WO2008/119353; U.S. Pat. Publ. No. US2009/0182127; U.S. Pat. Publ. No. US2010/0286374; U.S. Pat. Publ. No. US2011/0123532; Int. Pat. Publ. No. WO2011/131746; Int. Pat. Publ. No. WO2011/143545; or U.S. Pat. Publ. No. US2012/0149876.

For example, bispecific antibodies of the invention may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody (e.g., anti-CD38 antibody) and the second monospecific bivalent antibody are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl) phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Exemplary CH3 mutations that may be used in a first heavy chain and in a second heavy chain of the bispecific antibody are K409R and/or F405L.

Additional bispecific structures into which the VL and/or the VH regions of the antibodies of the invention may be incorporated are for example Dual Variable Domain Immunoglobulins (DVD) (Int. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. Nos. 5,932, 448; 6,833,441). DVDs are full length antibodies comprising the heavy chain having a structure VH1-linker-VH2-CH and the light chain having the structure VL1-linker-VL2-CL; linker being optional.

In some embodiments described herein, and in some embodiments of each and every one of the numbered embodiments listed below, the anti-CD38 antibody is conjugated to a toxin. Conjugation methods and suitable toxins are well known.

AML diagnosis is performed by a physician according to guidelines available, for example according to the World Health Organization (WHO) classification of AML (Brunning et al., World Health Organization Classificaiton of Tumors, 3, pp 77-80; eds. Jaffe et al., Pathology and Genetics of Tumours of Haematopoietic and Lymphoid Tissues) and according to guidelines available for example at National Comprehensive Cancer Network (http://_www_nccn.org/_professionals/_physician_gls/ f_guidelines_asp#site). The WHO classification incorporates clinical features, cytogenetics, immunophenotype, morphology and genetics in order to define biologically homogenous subgroups having therapeutic and prognostic relevance, and divides AML to four main subtypes: AML with recurrent genetic abnormalities, AML with multilineage dysplasia, therapy-related AML, and not otherwise categorized AML.

In some embodiments described herein, and in some embodiments of each and every one of the numbered embodiments listed below, AML is AML with at least one genetic abnormality.

AML may be associated with a translocation between chromosomes 8 and 21, translocation or inversion in chromosome 16, translocation between chromosomes 15 and 17, or changes in chromosome 11.

Common chromosomal rearrangements associated with AML are translocations t(8; 21)(q22; q22) (AML1/ETO), inv(16)(p13; q22) or t(16; 16)(p13; q22); (CBFβ/MYH11) or t(15; 17)(q22; q12); (PML/RARA). Patients with these favorable chromosomal translocations may be more susceptible to treatment and achieve higher complete remission (CR) rates.

In some embodiments described herein, and in some embodiments of each and every one of the numbered embodiments listed below, AML is associated with a translocation between chromosomes 8 and 21, translocation or inversion in chromosome 16, translocation between chromosomes 15 and 17, or changes in chromosome 11.

In some embodiments described herein, and in some embodiments of each and every one of the numbered embodiments listed below, AML is associated with a chromosomal abnormality t(8; 21)(q22; q22) (AML1/ETO), inv (16)(p13; q22) or t(16; 16)(p13; q22); (CBFβ/MYH11) or t(15; 17)(q22; q12); (PML/RARA).

Somatic mutations in various genes have been identified as being relevant to AML pathogenesis. These include mutations in fms-related tyrosine kinase 3 (FLT3), nucleophosmin (NPM1), isocitrate dehydrogenase 1(IDH1), isocitrate dehydrogenase 2 (IDH2), DNA (cytosine-5)-methyltransferase 3 (DNMT3A), CCAAT/enhancer binding protein alpha (CEBPA), U2 small nuclear RNA auxiliary factor 1(U2AF1), enhancer of zeste 2 polycomb repressive complex 2 subunit (EZH2), structural maintenance of chromosomes 1A (SMC1A) and structural maintenance of chromosomes 3 (SMC3) (The Cancer Genome Atlas Research Network; N Engl J Med 368:2059-74, 2013).

Activating mutations in the FLT3 gene have been described in approximately 20-30% of newly diagnosed AML patients. These include FLT3-ITD, internal tandem duplication mutations as a result of duplication and tandem insertion of parts of the juxtamembrane domain of the FLT3 gene (Schnittger et al., Blood 100:59-66, 2002) and D835 mutations in the FLT3 kinase domain. Patients with FLT3-ITD mutations appear to have reduced overall survival (OS) with increased relapse rate (Kottaridis et al., Blood 98: 1752-9, 2001; Yanada et al., Leukemia 19: 1345-9, 2005).

Mutations in IDH1 and IDH2 are present in about 15% of newly diagnosed patients. IDH1 mutations include substitutions R132H, R132X (X being any amino acid) and R100Q/R104V/F108L/R119Q/I130V and IDH2 mutations include substitutions R140Q and R172. IDH1/2 mutations are associated with poorer prognosis, except that IDH2$^{R140Q}$ is associated with somewhat prolonged survival (Molenaar et al., Biochim Biophys Acta 1846: 326-41, 2014). IDH1/2 mutation frequency increases with disease progression (Molenaar et al., Biochim Biophys Acta 1846: 326-41, 2014).

In some embodiments described herein, and in some embodiments of each and every one of the numbered embodiments listed below, AML is associated with one or more mutations in a fms-related tyrosine kinase 3 (FLT3), nucleophosmin (NPM1), isocitrate dehydrogenase 1(IDH1), isocitrate dehydrogenase 2 (IDH2), DNA (cytosine-5)-methyltransferase 3 (DNMT3A), CCAAT/enhancer binding protein alpha (CEBPA), U2 small nuclear RNA auxiliary factor 1(U2AF1), enhancer of zeste 2 polycomb repressive complex 2 subunit (EZH2), structural maintenance of chromosomes 1A (SMC1A) and structural maintenance of chromosomes 3 (SMC3).

In some embodiments described herein, and in some embodiments of each and every one of the numbered embodiments listed below, AML is associated with one or more mutations in fms-related tyrosine kinase 3 (FLT3).

In some embodiments described herein, and in some embodiments of each and every one of the numbered embodiments listed below, AML is associated with FLT3-ITD.

In some embodiments described herein, and in some embodiments of each and every one of the numbered embodiments listed below, AML is associated with one or more mutations in isocitrate dehydrogenase 1(IDH1) or isocitrate dehydrogenase 2 (IDH2).

In some embodiments described herein, and in some embodiments of each and every one of the numbered embodiments listed below, AML is associated with mutations R132H, R132X or R100Q/R104V/F108L/R119Q/I130V in isocitrate dehydrogenase 1 (IDH1).

In some embodiments described herein, and in some embodiments of each and every one of the numbered embodiments listed below, AML is associated with mutations R140Q and R172 in isocitrate dehydrogenase 2 (IDH2).

In some embodiments described herein, and in some embodiments of each and every one of the numbered embodiments listed below, AML is AML with multilineage dysplasia.

AML associated with multilineage dysplasia is characterized by dysplasia in two or more myeloid cell lineage, and by at least 20% increased blasts in either the blood or bone marrow.

In some embodiments described herein, and in some embodiments of each and every one of the numbered embodiments listed below, AML is therapy-related AML.

Therapy-related AML is a result of prior chemotherapy and/or radiation therapy, and may occur several years after exposure to the mutagenic agent. More than 90% of patients with therapy-related AML exhibit chromosomal abnormalities, including those of chromosomes 5 and/or 7.

Chromosomal rearrangements may be identified using well-known methods, for example fluorescent in situ hybridization, karyotyping, Southern blot, or sequencing.

In some embodiments described herein, and in some embodiments of each and every one of the numbered embodiments listed below, AML is undifferentiated AML (M0), AML with minimal maturation (M1), AML with maturation (M2), acute myelomonocytic leukemia (M4), acute monocytic leukemia (M5), acute erythroid leukemia (M6), acute megakaryoblastic leukemia (M7), acute basophilic leukemia, acute panmyelosis with fibrosis or myeloid sarcoma.

In some embodiments described herein, and in some embodiments of each and every one of the numbered embodiments listed below, AML is in remission.

AML in remission is typically defined as normocellular marrow with less than 5% blasts, normal peripheral blood count with >100,000/mm$^3$ platelets and >1,000/mm$^3$ neutrophils.

In some embodiments described herein, and in some embodiments of each and every one of the numbered embodiments listed below, AML is relapsed or refractory.

In some embodiments described herein, and in some embodiments of each and every one of the numbered embodiments listed below, the patient having AML has been treated with idarubicin, cytrabine or hydroxyurea.

In some embodiments described herein, and in some embodiments of each and every one of the numbered embodiments listed below, AML is adult AML.

In some embodiments described herein, and in some embodiments of each and every one of the numbered embodiments listed below, AML is pediatric AML.

In some embodiments described herein, and in some embodiments of each and every one of the numbered embodiments listed below, the anti-CD38 antibody is administered as a remission induction, post-remission or maintenance therapy.

Various qualitative and/or quantitative methods may be used to determine if a subject has relapsed, is resistant, has developed or is susceptible to developing a resistance to treatment with a drug or a therapeutic. Symptoms that may be associated with relapse and/or resistance include, for example, a decline or plateau of the well-being of the patient, an increase in the size of a tumor or tumor burden, increase in the number of cancer cells, arrested or slowed decline in growth of a tumor or tumor cells, and/or the spread of cancerous cells in the body from one location to other organs, tissues or cells. Re-establishment or worsening of various symptoms associated with tumor may also be an indication that a subject has relapsed or has developed or is susceptible to developing resistance to a drug or a therapeutic. The symptoms associated with cancer may vary according to the type of cancer. For example, symptoms associated with AML may include weakness, tiredness, feeling dizzy or cold, headaches, frequent nosebleeds, excess bruising or bleeding gums.

In some embodiments described herein, and in some embodiments of each and every one of the numbered embodiments listed below, the anti-CD38 antibody is administered in combination with at least one additional therapeutic.

AML may be treated with cytarabine (cytosine arabinoside, or ara-C) and/or antharcycline drugs such as doxorubicin, daunorubicin, daunomycin, idarubicin and mitoxantrone. Other chemotherapeutic drugs that may be used to treat AML include Hydroxyurea (Hydrea®), Decitabine (Dacogen®), Cladribine (Leustatin®, 2-CdA), Fludarabine (Fludara®), Topotecan, Etoposide (VP-16), 6-thioguanine (6-TG), Corticosteroid drugs, such as prednisone or dexamethasone (Decadron®), methotrexate (MTX), 6-mercaptopurine (6-MP) or Azacitidine (Vidaza®).

Other drugs that may be used to treat AML are all-trans-retinoic acid (ATRA), tretinoin, or Vesanoid® and arsenic trioxide (ATO, Trisenox®). ATRA and arsenic trioxide may be used to treat acute promyelocytic leukemia.

In some embodiments, the anti-CD38 antibody is administered to a patient in combination with cytarabine, daunorubicin/daunomycin, idarubicin, mitoxantrone, hydroxyurea, decitabine, cladribine, fludarabine, topotecan, etoposide 6-thioguanine, corticosteroid, prednisone, dexamethasone, methotrexate, 6-mercaptopurine or azacitidine.

In some embodiments described herein, and in some embodiments of each and every one of the numbered embodiments listed below, the anti-CD38 antibody is administered to a patient in combination with decitabine.

In some embodiments described herein, and in some embodiments of each and every one of the numbered embodiments listed below, the anti-CD38 antibody is administered to a patient in combination with cytarabine and doxorubicin.

In some embodiments described herein, and in some embodiments of each and every one of the numbered embodiments listed below, the subject has received or will receive radiotherapy.

Radiotherapy may be external beam radiation, intensity modulated radiation therapy (IMRT), focused radiation, or any form of radiosurgery including Gamma Knife, Cyberknife, Linac, and interstitial radiation (e.g. implanted radioactive seeds, GliaSite balloon), and/or with surgery.

Focused radiation methods that may be used include stereotactic radiosurgery, fractionated stereotactic radiosurgery, and intensity-modulated radiation therapy (IMRT). It is apparent that stereotactic radiosurgery involves the precise delivery of radiation to a tumorous tissue, for example, a brain tumor, while avoiding the surrounding non-tumorous, normal tissue. The dosage of radiation applied using stereotactic radiosurgery may vary, typically from 1 Gy to about 30 Gy, and may encompass intermediate ranges including, for example, from 1 to 5, 10, 15, 20, 25, up to 30 Gy in dose. Because of noninvasive fixation devices, stereotactic radiation need not be delivered in a single treatment. The treatment plan may be reliably duplicated day-to-day, thereby allowing multiple fractionated doses of radiation to be delivered. When used to treat a tumor over time, the radiosurgery is referred to as "fractionated stereotactic radiosurgery" or FSR. In contrast, stereotactic radiosurgery refers to a one-session treatment. Fractionated stereotactic radiosurgery may result in a high therapeutic ratio, i.e., a high rate of killing of tumor cells and a low effect on normal tissue. The tumor and the normal tissue respond differently to high single doses of radiation vs. multiple smaller doses of radiation. Single large doses of radiation may kill more normal tissue than several smaller doses of radiation may. Accordingly, multiple smaller doses of radiation can kill more tumor cells while sparing normal tissue. The dosage of radiation applied using fractionated stereotactic radiation may vary from range from 1 Gy to about 50 Gy, and may encompass intermediate ranges including, for example, from 1 to 5, 10, 15, 20, 25, 30, 40, up to 50 Gy in hypofractionated doses. Intensity-modulated radiation therapy (IMRT) may also be used. IMRT is an advanced mode of high-precision three-dimensional conformal radiation therapy (3DCRT), which uses computer-controlled linear accelerators to deliver precise radiation doses to a malignant tumor or specific areas within the tumor. In 3DCRT, the profile of each radiation beam is shaped to fit the profile of the target from a beams eye view (BEV) using a multileaf collimator (MLC), thereby producing a number of beams. IMRT allows the radiation dose to conform more precisely to the three-dimensional (3-D) shape of the tumor by modulating the intensity of the radiation beam in multiple small volumes. Accordingly, IMRT allows higher radiation doses to be focused to regions within the tumor while minimizing the dose to surrounding normal critical structures. IMRT improves the ability to conform the treatment volume to concave tumor shapes, for example, when the tumor is wrapped around a vulnerable structure, such as the spinal cord or a major organ or blood vessel.

In some embodiments described herein, and in some embodiments of each and every one of the numbered embodiments listed below, the subject is undergoing hematopoietic stem cell transplantation (HSCT).

In some embodiments of the invention described herein, and in some embodiments of each and every one of the numbered embodiments listed below, the HSCT is allogeneic, autologous or synegeneic, i.e. the donor is a twin. Autologous HSCT comprises the extraction of HSC from the subject and freezing of the harvested HSC. After myeloablation, the subject's stored HSC are transplanted into the subject. Allogeneic HSCT involves HSC obtained from an allogeneic HSC donor who has an HLA type that matches the subject.

"Hematopoietic stem cell transplantation" is the transplantation of blood stem cells derived from the bone marrow (in this case known as bone marrow transplantation), blood (such as peripheral blood and umbilical cord blood), or amniotic fluid.

"Undergoing hematopoietic stem cell transplantation" means that the patient did already receive, is receiving or will receive HSCT.

In some embodiments of the invention described herein, and in some embodiments of each and every one of the numbered embodiments listed below, the patient has completed chemotherapy and/or radiation therapy prior to HSCT.

Patients may be treated with chemotherapy and/or radiation therapy prior to HSCT (so-called pre-transplant preparation) to eradicate some or all of the patient's hematopoietic cells prior to transplant. The patient may also be treated with immunosuppressants in case of allogeneic HSCT. An exemplary pre-transplant preparation therapy is high-dose melphalan (see for example Skinner et al., Ann Intern Med 140:85-93, 2004; Gertz et al., Bone Marrow Transplant 34: 1025-31, 2004; Perfetti et al., Haematologica 91:1635-43, 2006). The radiation therapy that may be employed in pre-transplant treatment may be carried out according to commonly known protocols in this field. Radiation therapy may also be provided simultaneously, sequentially or separately with the anti-CD38 antibody.

In some embodiments described herein, and in some embodiments of each and every one of the numbered embodiments listed below, the subject having AML is homozygous for phenylalanine at position 158 of CD16 (FcγRIIIa-158F/F genotype) or heterozygous for valine and pheynylalanine at position 158 of CD16 (FcγRIIIa-158F/V genotype). CD16 is also known as the Fc gamma receptor Ma (FcγRIIIa) or the low affinity immunoglobulin gamma Fc region receptor III-A isoform. Valine/phenylalanine (V/F) polymorphism at FcγRIIIa protein residue position 158 has been shown to affect FcγRIIIa affinity to human IgG. Receptor with FcγRIIIa-158F/F or FcγRIIIa-158F/V polymorphisms demonstrates reduced Fc engagement and therefore reduced ADCC when compared to the FcγRIIIa-158V/V. The lack of or low amount of fucose on human N-linked oligosaccharides improves the ability of the antibodies to induce ADCC due to improved binding of the antibodies to human FcγRIIIa (CD16) (Shields et al., J Biol Chem 277: 26733-40, 2002). Patients can be analyzed for their FcγRIIIa polymorphism using routine methods.

The invention also provides for the method of treating a subject having AML, comprising administering to a patient in need thereof an anti-CD38 antibody that binds to the region SKRNIQFSCKNIYR (SEQ ID NO: 2) and the region EKVQTLEAWVIHGG (SEQ ID NO: 3) of human CD38 (SEQ ID NO: 1), wherein the subject is homozygous for phenylalanine at position 158 of CD16 or heterozygous for valine and pheynylalanine at position 158 of CD16.

The invention also provides an anti-CD38 antibody for use in treating a subject having AML, wherein the subject has a mutation in fms-related tyrosine kinase 3 (FLT3).

The invention also provides an anti-CD38 antibody for use in treating a subject having AML, wherein the subject has a FLT3-ITD mutation.

The invention also provides an anti-CD38 antibody for use in treating a subject having AML, wherein the subject has a mutation in isocitrate dehydrogenase 2 (IDH2).

The invention also provides an anti-CD38 antibody for use in treating a subject having AML, wherein the subject has a R140Q mutation in isocitrate dehydrogenase 2 (IDH2).

The invention also provides an anti-CD38 antibody for use in treating a subject having AML, wherein the subject has a mutation in DNA (cytosine-5)-methyltransferase 3 (DNMT3A).

The invention also provides an anti-CD38 antibody for use in treating a subject having AML, wherein the subject has a R882H mutation in DNA (cytosine-5)-methyltransferase 3 (DNMT3A).

The invention also provides an anti-CD38 antibody for use in treating a subject having AML in combination with a second therapeutic agent, wherein the subject has a mutation in fms-related tyrosine kinase 3 (FLT3).

The invention also provides an anti-CD38 antibody for use in treating a subject having AML in combination with a second therapeutic agent, wherein the subject has a FLT3-ITD mutation.

The invention also provides an anti-CD38 antibody for use in treating a subject having AML in combination with a second therapeutic agent, wherein the subject has a mutation in isocitrate dehydrogenase 2 (IDH2).

The invention also provides an anti-CD38 antibody for use in treating a subject having AML in combination with a second therapeutic agent, wherein the subject has a R140Q mutation in isocitrate dehydrogenase 2 (IDH2).

The invention also provides an anti-CD38 antibody for use in treating a subject having AML in combination with a second therapeutic agent, wherein the subject has a mutation in DNA (cytosine-5)-methyltransferase 3 (DNMT3A).

The invention also provides an anti-CD38 antibody for use in treating a subject having AML, in combination with a second therapeutic agent, wherein the subject has a R882H mutation in DNA (cytosine-5)-methyltransferase 3 (DNMT3A).

The invention also provides an anti-CD38 antibody for use in treating a subject having AML in combination with dacogen, wherein the subject has a mutation in fms-related tyrosine kinase 3 (FLT3)

The invention also provides an anti-CD38 antibody for use in treating a subject having AML in combination with dacogen, wherein the subject has a FLT3-ITD mutation.

The invention also provides an anti-CD38 antibody for use in treating a subject having AML in combination with dacogen, wherein the subject has a mutation in isocitrate dehydrogenase 2 (IDH2).

The invention also provides an anti-CD38 antibody for use in treating a subject having AML in combination with dacogen, wherein the subject has a R140Q mutation in isocitrate dehydrogenase 2 (IDH2).

The invention also provides an anti-CD38 antibody for use in treating a subject having AML in combination with dacogen, wherein the subject has a mutation in DNA (cytosine-5)-methyltransferase 3 (DNMT3A).

The invention also provides an anti-CD38 antibody for use in treating a subject having AML in combination with dacogen, wherein the subject has a R882H mutation in DNA (cytosine-5)-methyltransferase 3 (DNMT3A).

The invention also provides an anti-CD38 antibody for use in treating a subject having AML in combination with cytrabine, wherein the subject has a mutation in fms-related tyrosine kinase 3 (FLT3)

The invention also provides an anti-CD38 antibody for use in treating a subject having AML in combination with cytrabine, wherein the subject has a FLT3-ITD mutation.

The invention also provides an anti-CD38 antibody for use in treating a subject having AML in combination with cytrabine, wherein the subject has a mutation in isocitrate dehydrogenase 2 (IDH2).

The invention also provides an anti-CD38 antibody for use in treating a subject having AML, in combination with cytrabine, wherein the subject has a R140Q mutation in isocitrate dehydrogenase 2 (IDH2).

The invention also provides an anti-CD38 antibody for use in treating a subject having AML in combination with cytrabine, wherein the subject has a mutation in DNA (cytosine-5)-methyltransferase 3 (DNMT3A).

The invention also provides an anti-CD38 antibody for use in treating a subject having AML in combination with cytrabine, wherein the subject has a R882H mutation in DNA (cytosine-5)-methyltransferase 3 (DNMT3A).

The invention also provides an anti-CD38 antibody for use in treating a subject having AML in combination with doxorubicin, wherein the subject has a mutation in fms-related tyrosine kinase 3 (FLT3)

The invention also provides an anti-CD38 antibody for use in treating a subject having AML in combination with doxorubicin, wherein the subject has a FLT3-ITD mutation.

The invention also provides an anti-CD38 antibody for use in treating a subject having AML in combination with doxorubicin, wherein the subject has a mutation in isocitrate dehydrogenase 2 (IDH2).

The invention also provides an anti-CD38 antibody for use in treating a subject having AML in combination with doxorubicin, wherein the subject has a R140Q mutation in isocitrate dehydrogenase 2 (IDH2).

The invention also provides an anti-CD38 antibody for use in treating a subject having AML in combination with doxorubicin, wherein the subject has a mutation in DNA (cytosine-5)-methyltransferase 3 (DNMT3A).

The invention also provides an anti-CD38 antibody for use in treating a subject having AML in combination with doxorubicin, wherein the subject has a R882H mutation in DNA (cytosine-5)-methyltransferase 3 (DNMT3A).

The invention also provides an anti-CD38 antibody for use in treating a subject having AML in combination with cytrabine and doxorubicin, wherein the subject has a mutation in fms-related tyrosine kinase 3 (FLT3)

The invention also provides an anti-CD38 antibody for use in treating a subject having AML, in combination with cytrabine and doxorubicin, wherein the subject has a FLT3-ITD mutation.

The invention also provides an anti-CD38 antibody for use in treating a subject having AML in combination with cytrabine and doxorubicin, wherein the subject has a mutation in isocitrate dehydrogenase 2 (IDH2).

The invention also provides an anti-CD38 antibody for use in treating a subject having AML in combination with cytrabine and doxorubicin, wherein the subject has a R140Q mutation in isocitrate dehydrogenase 2 (IDH2).

The invention also provides an anti-CD38 antibody for use in treating a subject having AML in combination with cytrabine and doxorubicin, wherein the subject has a mutation in DNA (cytosine-5)-methyltransferase 3 (DNMT3A).

The invention also provides an anti-CD38 antibody for use in treating a subject having AML in combination with cytrabine and doxorubicin, wherein the subject has a R882H mutation in DNA (cytosine-5)-methyltransferase 3 (DNMT3A).

The invention also provides an anti-CD38 antibody comprising the VH of SEQ ID NO: 4 and the VL of SEQ ID NO: 5 for use in treating a subject having AML, wherein the subject has a mutation in fms-related tyrosine kinase 3 (FLT3).

The invention also provides an anti-CD38 antibody comprising the VH of SEQ ID NO: 4 and the VL of SEQ ID NO: 5 for use in treating a subject having AML, wherein the subject has a FLT3-ITD mutation.

The invention also provides an anti-CD38 antibody comprising the VH of SEQ ID NO: 4 and the VL of SEQ ID NO: 5 for use in treating a subject having AML, wherein the subject has a mutation in isocitrate dehydrogenase 2 (IDH2).

The invention also provides an anti-CD38 antibody comprising the VH of SEQ ID NO: 4 and the VL of SEQ ID NO: 5 for use in treating a subject having AML, wherein the subject has a R140Q mutation in isocitrate dehydrogenase 2 (IDH2).

The invention also provides an anti-CD38 antibody comprising the VH of SEQ ID NO: 4 and the VL of SEQ ID NO: 5 for use in treating a subject having AML, wherein the subject has a mutation in DNA (cytosine-5)-methyltransferase 3 (DNMT3A).

The invention also provides an anti-CD38 antibody comprising the VH of SEQ ID NO: 4 and the VL of SEQ ID NO: 5 for use in treating a subject having AML, wherein the subject has a R882H mutation in DNA (cytosine-5)-methyltransferase 3 (DNMT3A).

The invention also provides an anti-CD38 antibody comprising the VH of SEQ ID NO: 4 and the VL of SEQ ID NO: 5 for use in treating a subject having AML in combination with a second therapeutic agent, wherein the subject has a mutation in fms-related tyrosine kinase 3 (FLT3).

The invention also provides an anti-CD38 antibody comprising the VH of SEQ ID NO: 4 and the VL of SEQ ID NO: 5 for use in treating a subject having AML in combination with a second therapeutic agent, wherein the subject has a FLT3-ITD mutation.

The invention also provides an anti-CD38 antibody comprising the VH of SEQ ID NO: 4 and the VL of SEQ ID NO: 5 for use in treating a subject having AML in combination with a second therapeutic agent, wherein the subject has a mutation in isocitrate dehydrogenase 2 (IDH2).

The invention also provides an anti-CD38 antibody comprising the VH of SEQ ID NO: 4 and the VL of SEQ ID NO: 5 for use in treating a subject having AML in combination with a second therapeutic agent, wherein the subject has a R140Q mutation in isocitrate dehydrogenase 2 (IDH2).

The invention also provides an anti-CD38 antibody comprising the VH of SEQ ID NO: 4 and the VL of SEQ ID NO: 5 for use in treating a subject having AML in combination with a second therapeutic agent, wherein the subject has a mutation in DNA (cytosine-5)-methyltransferase 3 (DNMT3A).

The invention also provides an anti-CD38 antibody comprising the VH of SEQ ID NO: 4 and the VL of SEQ ID NO: 5 for use in treating a subject having AML in combination with a second therapeutic agent, wherein the subject has a R882H mutation in DNA (cytosine-5)-methyltransferase 3 (DNMT3A).

The invention also provides an anti-CD38 antibody comprising the VH of SEQ ID NO: 4 and the VL of SEQ ID NO: 5 for use in treating a subject having AML in combination with dacogen, wherein the subject has a mutation in fms-related tyrosine kinase 3 (FLT3).

The invention also provides an anti-CD38 antibody comprising the VH of SEQ ID NO: 4 and the VL of SEQ ID NO: 5 for use in treating a subject having AML in combination with dacogen, wherein the subject has a FLT3-ITD mutation.

The invention also provides an anti-CD38 antibody comprising the VH of SEQ ID NO: 4 and the VL of SEQ ID NO: 5 for use in treating a subject having AML in combination with dacogen, wherein the subject has a mutation in isocitrate dehydrogenase 2 (IDH2).

The invention also provides an anti-CD38 antibody comprising the VH of SEQ ID NO: 4 and the VL of SEQ ID NO: 5 for use in treating a subject having AML in combination with dacogen, wherein the subject has a R140Q mutation in isocitrate dehydrogenase 2 (IDH2).

The invention also provides an anti-CD38 antibody comprising the VH of SEQ ID NO: 4 and the VL of SEQ ID NO: 5 for use in treating a subject having AML in combination with dacogen, wherein the subject has a mutation in DNA (cytosine-5)-methyltransferase 3 (DNMT3A).

The invention also provides an anti-CD38 antibody comprising the VH of SEQ ID NO: 4 and the VL of SEQ ID NO: 5 for use in treating a subject having AML in combination with dacogen, wherein the subject has a R882H mutation in DNA (cytosine-5)-methyltransferase 3 (DNMT3A).

The invention also provides an anti-CD38 antibody comprising the VH of SEQ ID NO: 4 and the VL of SEQ ID NO: 5 for use in treating a subject having AML in combination with cytrabine, wherein the subject has a mutation in fms-related tyrosine kinase 3 (FLT3).

The invention also provides an anti-CD38 antibody comprising the VH of SEQ ID NO: 4 and the VL of SEQ ID NO: 5 for use in treating a subject having AML in combination with cytrabine, wherein the subject has a FLT3-ITD mutation.

The invention also provides an anti-CD38 antibody comprising the VH of SEQ ID NO: 4 and the VL of SEQ ID NO: 5 for use in treating a subject having AML in combination with cytrabine, wherein the subject has a mutation in isocitrate dehydrogenase 2 (IDH2).

The invention also provides an anti-CD38 antibody comprising the VH of SEQ ID NO: 4 and the VL of SEQ ID NO: 5 for use in treating a subject having AML in combination with cytrabine, wherein the subject has a R140Q mutation in isocitrate dehydrogenase 2 (IDH2).

The invention also provides an anti-CD38 antibody comprising the VH of SEQ ID NO: 4 and the VL of SEQ ID NO: 5 for use in treating a subject having AML in combination with cytrabine, wherein the subject has a mutation in DNA (cytosine-5)-methyltransferase 3 (DNMT3A).

The invention also provides an anti-CD38 antibody comprising the VH of SEQ ID NO: 4 and the VL of SEQ ID NO: 5 for use in treating a subject having AML in combination with cytrabine, wherein the subject has a R882H mutation in DNA (cytosine-5)-methyltransferase 3 (DNMT3A).

The invention also provides an anti-CD38 antibody comprising the VH of SEQ ID NO: 4 and the VL of SEQ ID NO: 5 for use in treating a subject having AML in combination with doxorubicin, wherein the subject has a mutation in fms-related tyrosine kinase 3 (FLT3).

The invention also provides an anti-CD38 antibody comprising the VH of SEQ ID NO: 4 and the VL of SEQ ID NO: 5 for use in treating a subject having AML in combination with doxorubicin, wherein the subject has a FLT3-ITD mutation.

The invention also provides an anti-CD38 antibody comprising the VH of SEQ ID NO: 4 and the VL of SEQ ID NO: 5 for use in treating a subject having AML in combination with doxorubicin, wherein the subject has a mutation in isocitrate dehydrogenase 2 (IDH2).

The invention also provides an anti-CD38 antibody comprising the VH of SEQ ID NO: 4 and the VL of SEQ ID NO: 5 for use in treating a subject having AML in combination with doxorubicin, wherein the subject has a R140Q mutation in isocitrate dehydrogenase 2 (IDH2).

The invention also provides an anti-CD38 antibody comprising the VH of SEQ ID NO: 4 and the VL of SEQ ID NO: 5 for use in treating a subject having AML in combination with doxorubicin, wherein the subject has a mutation in DNA (cytosine-5)-methyltransferase 3 (DNMT3A).

The invention also provides an anti-CD38 antibody comprising the VH of SEQ ID NO: 4 and the VL of SEQ ID NO: 5 for use in treating a subject having AML in combination with doxorubicin, wherein the subject has a R882H mutation in DNA (cytosine-5)-methyltransferase 3 (DNMT3A).

The invention also provides an anti-CD38 antibody comprising the VH of SEQ ID NO: 4 and the VL of SEQ ID NO: 5 for use in treating a subject having AML in combination with cytrabine and doxorubicin, wherein the subject has a mutation in fms-related tyrosine kinase 3 (FLT3).

The invention also provides an anti-CD38 antibody comprising the VH of SEQ ID NO: 4 and the VL of SEQ ID NO: 5 for use in treating a subject having AML in combination with cytrabine and doxorubicin, wherein the subject has a FLT3-ITD mutation.

The invention also provides an anti-CD38 antibody comprising the VH of SEQ ID NO: 4 and the VL of SEQ ID NO: 5 for use in treating a subject having AML in combination with cytrabine and doxorubicin, wherein the subject has a mutation in isocitrate dehydrogenase 2 (IDH2).

The invention also provides an anti-CD38 antibody comprising the VH of SEQ ID NO: 4 and the VL of SEQ ID NO: 5 for use in treating a subject having AML in combination with cytrabine and doxorubicin, wherein the subject has a R140Q mutation in isocitrate dehydrogenase 2 (IDH2).

The invention also provides an anti-CD38 antibody comprising the VH of SEQ ID NO: 4 and the VL of SEQ ID NO: 5 for use in treating a subject having AML in combination with cytrabine and doxorubicin, wherein the subject has a mutation in DNA (cytosine-5)-methyltransferase 3 (DNMT3A).

The invention also provides an anti-CD38 antibody comprising the VH of SEQ ID NO: 4 and the VL of SEQ ID NO: 5 for use in treating a subject having AML in combination with cytrabine and doxorubicin, wherein the subject has a R882H mutation in DNA (cytosine-5)-methyltransferase 3 (DNMT3A).

The invention also provides an anti-CD38 antibody comprising the VH of SEQ ID NO: 15 and the VL of SEQ ID NO: 16 for use in treating a subject having AML, wherein the subject has a mutation in fms-related tyrosine kinase 3 (FLT3).

The invention also provides an anti-CD38 antibody comprising the VH of SEQ ID NO: 15 and the VL of SEQ ID NO: 16 for use in treating a subject having AML, wherein the subject has a FLT3-ITD mutation.

The invention also provides an anti-CD38 antibody comprising the VH of SEQ ID NO: 15 and the VL of SEQ ID NO: 16 for use in treating a subject having AML, wherein the subject has a mutation in isocitrate dehydrogenase 2 (IDH2).

The invention also provides an anti-CD38 antibody comprising the VH of SEQ ID NO: 15 and the VL of SEQ ID NO: 16 for use in treating a subject having AML, wherein the subject has a R140Q mutation in isocitrate dehydrogenase 2 (IDH2).

The invention also provides an anti-CD38 antibody comprising the VH of SEQ ID NO: 15 and the VL of SEQ ID NO: 16 for use in treating a subject having AML, wherein the subject has a mutation in DNA (cytosine-5)-methyltransferase 3 (DNMT3A).

The invention also provides an anti-CD38 antibody comprising the VH of SEQ ID NO: 15 and the VL of SEQ ID NO: 16 for use in treating a subject having AML, wherein the subject has a R882H mutation in DNA (cytosine-5)-methyltransferase 3 (DNMT3A).

The invention also provides an anti-CD38 antibody comprising the VH of SEQ ID NO: 17 and the VL of SEQ ID NO: 18 for use in treating a subject having AML, wherein the subject has a mutation in fms-related tyrosine kinase 3 (FLT3).

The invention also provides an anti-CD38 antibody comprising the VH of SEQ ID NO: 17 and the VL of SEQ ID NO: 18 for use in treating a subject having AML, wherein the subject has a FLT3-ITD mutation.

The invention also provides an anti-CD38 antibody comprising the VH of SEQ ID NO: 17 and the VL of SEQ ID NO: 18 for use in treating a subject having AML, wherein the subject has a mutation in isocitrate dehydrogenase 2 (IDH2).

The invention also provides an anti-CD38 antibody comprising the VH of SEQ ID NO: 17 and the VL of SEQ ID NO: 18 for use in treating a subject having AML, wherein the subject has a R140Q mutation in isocitrate dehydrogenase 2 (IDH2).

The invention also provides an anti-CD38 antibody comprising the VH of SEQ ID NO: 17 and the VL of SEQ ID NO: 18 for use in treating a subject having AML, wherein the subject has a mutation in DNA (cytosine-5)-methyltransferase 3 (DNMT3A).

The invention also provides an anti-CD38 antibody comprising the VH of SEQ ID NO: 17 and the VL of SEQ ID NO: 18 for use in treating a subject having AML, wherein the subject has a R882H mutation in DNA (cytosine-5)-methyltransferase 3 (DNMT3A).

The invention also provides an anti-CD38 antibody comprising the VH of SEQ ID NO: 19 and the VL of SEQ ID NO: 20 for use in treating a subject having AML, wherein the subject has a mutation in fms-related tyrosine kinase 3 (FLT3).

The invention also provides an anti-CD38 antibody comprising the VH of SEQ ID NO: 19 and the VL of SEQ ID NO: 20 for use in treating a subject having AML, wherein the subject has a FLT3-ITD mutation.

The invention also provides an anti-CD38 antibody comprising the VH of SEQ ID NO: 19 and the VL of SEQ ID NO: 20 for use in treating a subject having AML, wherein the subject has a mutation in isocitrate dehydrogenase 2 (IDH2).

The invention also provides an anti-CD38 antibody comprising the VH of SEQ ID NO: 19 and the VL of SEQ ID NO: 20 for use in treating a subject having AML, wherein the subject has a R140Q mutation in isocitrate dehydrogenase 2 (IDH2).

The invention also provides an anti-CD38 antibody comprising the VH of SEQ ID NO: 19 and the VL of SEQ ID NO: 20 for use in treating a subject having AML, wherein the subject has a mutation in DNA (cytosine-5)-methyltransferase 3 (DNMT3A).

The invention also provides an anti-CD38 antibody comprising the VH of SEQ ID NO: 19 and the VL of SEQ ID NO: 20 for use in treating a subject having AML, wherein the subject has a R882H mutation in DNA (cytosine-5)-methyltransferase 3 (DNMT3A).

The invention also provides an anti-CD38 antibody comprising the VH of SEQ ID NO: 21 and the VL of SEQ ID NO: 22 for use in treating a subject having AML, wherein the subject has a mutation in fms-related tyrosine kinase 3 (FLT3).

The invention also provides an anti-CD38 antibody comprising the VH of SEQ ID NO: 21 and the VL of SEQ ID NO: 22 for use in treating a subject having AML, wherein the subject has a FLT3-ITD mutation.

The invention also provides an anti-CD38 antibody comprising the VH of SEQ ID NO: 21 and the VL of SEQ ID NO: 22 for use in treating a subject having AML, wherein the subject has a mutation in isocitrate dehydrogenase 2 (IDH2).

The invention also provides an anti-CD38 antibody comprising the VH of SEQ ID NO: 21 and the VL of SEQ ID NO: 22 for use in treating a subject having AML, wherein the subject has a R140Q mutation in isocitrate dehydrogenase 2 (IDH2).

The invention also provides an anti-CD38 antibody comprising the VH of SEQ ID NO: 21 and the VL of SEQ ID NO: 22 for use in treating a subject having AML, wherein the subject has a mutation in DNA (cytosine-5)-methyltransferase 3 (DNMT3A).

The invention also provides an anti-CD38 antibody comprising the VH of SEQ ID NO: 21 and the VL of SEQ ID NO: 22 for use in treating a subject having AML, wherein the subject has a R882H mutation in DNA (cytosine-5)-methyltransferase 3 (DNMT3A).

Administration/Pharmaceutical Compositions

In the methods of the invention described herein, and in some embodiments of each and every one of the numbered embodiments listed below, the anti-CD38 antibodies may be provided in suitable pharmaceutical compositions comprising the anti-CD38 antibody and a pharmaceutically acceptable carrier. The carrier may be diluent, adjuvant, excipient, or vehicle with which the anti-CD38 antibody is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules or antibodies of the invention in such pharmaceutical formulation may vary widely, i.e., from less than about 0.5%, usually to at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, PA 2006, Part 5, Pharmaceutical Manufacturing pp 691-1092, see especially pp. 958-989.

The mode of administration of the anti-CD38 antibody in the methods of the invention described herein, and in some embodiments of each and every one of the numbered embodiments listed below, may be any suitable route such as parenteral administration, e.g., intradermal, intramuscular, intraperitoneal, intravenous or subcutaneous, pulmonary, transmucosal (oral, intranasal, intravaginal, rectal) or other means appreciated by the skilled artisan, as well known in the art.

The anti-CD38 antibody in the methods of the invention described herein, and in some embodiments of each and every one of the numbered embodiments listed below, may be administered to a patient by any suitable route, for example parentally by intravenous (i.v.) infusion or bolus injection, intramuscularly or subcutaneously or intraperitoneally. i.v. infusion may be given over for example 15, 30, 60, 90, 120, 180, or 240 minutes, or from 1, 2, 3, 4, 5, 6, 7, 8, 9, 10, 11 or 12 hours.

The dose given to a patient having AML is sufficient to alleviate or at least partially arrest the disease being treated ("therapeutically effective amount") and may be sometimes 0.005 mg to about 100 mg/kg, e.g. about 0.05 mg to about 30 mg/kg or about 5 mg to about 25 mg/kg, or about 4 mg/kg, about 8 mg/kg, about 16 mg/kg or about 24 mg/kg, or for example about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m$^2$. Usually between 1 and 8 doses, (e.g., 1, 2, 3, 4, 5, 6, 7 or 8) may be administered to treat AML, but 9, 10, 11, 12, 13, 14, 15, 16, 17, 18, 19, 20 or more doses may be given.

The administration of the anti-CD38 antibody in the methods of the invention described herein, and in some embodiments of each and every one of the numbered embodiments listed below, may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the anti-CD38 antibody in the methods of the invention may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

The anti-CD38 antibodies may be administered in the methods of the invention described herein, and in some embodiments of each and every one of the numbered embodiments listed below, by maintenance therapy, such as, e.g., once a week for a period of 6 months or more.

For example, anti-CD38 antibodies in the methods of the invention described herein, and in some embodiments of each and every one of the numbered embodiments listed below, may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

Anti-CD38 antibodies in the methods of the invention described herein, and in some embodiments of each and every one of the numbered embodiments listed below, may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

The anti-CD38 antibody in the methods of the invention described herein, and in some embodiments of each and every one of the numbered embodiments listed below, may be lyophilized for storage and reconstituted in a suitable carrier prior to use. This technique has been shown to be effective with conventional protein preparations and well known lyophilization and reconstitution techniques can be employed.

The anti-CD38 antibody in the methods of the invention described herein, and in some embodiments of each and every one of the numbered embodiments listed below, may be administered in combination with all-trans retinoic acid (ATRA).

ATRA may be provided as a dosage of 45 mg/m$^2$/day PO or 25 mg/m$^2$/day PO.

The anti-CD38 antibody in the methods of the invention described herein, and in some embodiments of each and every one of the numbered embodiments listed below, may be administered in combination with dacogen.

Dacogen may be administered for a minimum of 4 cycles repeated every 6 weeks at 15 mg/m$^2$ i. v. over 3 hours repeated every 8 hours for 3 days. Alternatively, dacogen may be administered 20 mg/m$^2$ i.v. over 1 hour repeated daily for 5 days, and the cycle repeated every 4 weeks.

The anti-CD38 antibody in the methods of the invention described herein, and in some embodiments of each and every one of the numbered embodiments listed below, may be administered in combination with cytrabine and doxorubicin.

Cytarabine may be administered 2 to 3 g/m$^2$ i.v. over 1-3 hours every twelve hours for up to 12 doses.

Doxorubicin may be administered 40 to 60 mg/m$^2$ i.v. every 21 to 28 days, or 60 to 75 mg/m$^2$ i.v. once every 21 days.

Anti-CD38 antibody may be administered together with any form of radiation therapy including external beam radiation, intensity modulated radiation therapy (IMRT) and any form of radiosurgery including Gamma Knife, Cyberknife, Linac, and interstitial radiation (e.g. implanted radioactive seeds, GliaSite balloon), and/or with surgery.

While having described the invention in general terms, the embodiments of the invention will be further disclosed in the following examples that should not be construed as limiting the scope of the claims.

Further Embodiments of the Invention

Set out below are certain further embodiments of the invention according to the disclosures elsewhere herein. Features from embodiments of the invention set out above described as relating to the invention disclosed herein also relate to each and every one of these further numbered embodiments.

1) An anti-CD38 antibody for use in treating a subject having acute myeloid leukemia (AML).
2) An anti-CD38 antibody for use in treating a subject having AML, in combination with a second therapeutic agent, wherein the second therapeutic agent
   a. is optionally cytarabine, daunorubicin, idarubicin, mitoxantrone, hydroxyurea, decitabine, cladribine, fludarabine, topotecan, etoposide 6-thioguanine, corticosteroid, prednisone, dexamethasone, methotrexate, 6-mercaptopurine, azacitidine, arsenic trioxide or all-trans retinoic acid; and/or
   b. increases surface expression of CD38.
3) A combination of an anti-CD38 antibody and all-trans retinoic acid for use in treating a subject having AML.
4) A combination of an anti-CD38 antibody and decitabine for use in treating a subject having AML.
5) A combination of an anti-CD38 antibody and cytarabine and/or doxorubicin for use in treating a subject having AML.
6) The anti-CD38 antibody for use according to embodiment 1 or 2, or the combination according to embodiment 3-5, wherein the anti-CD38 antibody competes for binding to CD38 with an antibody comprising a heavy chain variable region (VH) of SEQ ID NO: 4 and a light chain variable region (VL) of SEQ ID NO: 5.
7) The anti-CD38 antibody for use according to embodiment 1, 2 or 6, or the combination according to embodiment 3-6, wherein the anti-CD38 antibody induces killing of AML cells that express CD38 by apoptosis.
8) The anti-CD38 antibody for use according to embodiment 1, 2, 6 or 7 or the combination according to embodiment 3-7, wherein the anti-CD38 antibody binds to the region SKRNIQFSCKNIYR (SEQ ID NO: 2) and the region EKVQTLEAWVIHGG (SEQ ID NO: 3) of human CD38 (SEQ ID NO: 1).
9) The anti-CD38 antibody for use according to embodiment 1, 2, 6-8, or the combination according to embodiment 3-8, wherein the anti-CD38 antibody:
   a. is of IgG1, IgG2, IgG3 or IgG4 isotype;
   b. has a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%; or
   c. comprise a substitution in the antibody Fc at amino acid positions 256, 290, 298, 312, 356, 330, 333, 334, 360, 378 or 430, when residue numbering according to the EU index.
10) The anti-CD38 antibody for use according to embodiment 1, 2, 6-9, or the combination according to embodiment 3-9, wherein the anti-CD38 antibody comprises
    a. the heavy chain complementarity determining regions (HCDR) 1 (HCDR1), 2 (HCDR2) and 3 (HCDR3) sequences of SEQ ID NOs: 6, 7 and 8, respectively;
    b. the light chain complementarity determining regions (LCDR) 1 (LCDR1), 2 (LCDR2) and 3 (LCDR3) sequences of SEQ ID NOs: 9, 10 and 11, respectively;

c. HCDR1, HCDR2, HCDR3, LCDR1, LCDR2 and LCDR3 sequences of SEQ ID NOs: 6, 7, 8, 9, 10 and 11, respectively;
d. the heavy chain variable region (VH) of SEQ ID NO: 4 and the light chain variable region (VL) of SEQ ID NO: 5;
e. a heavy chain comprising an amino acid sequence that is 95%, 96%, 97%, 98% or 99% identical to that of SEQ ID NO: 12 and a light chain comprising an amino acid sequence that is 95%, 96%, 97%, 98% or 99% identical to that of SEQ ID NO: 13; or
f. the heavy chain of SEQ ID NO: 12 and the light chain of SEQ ID NO: 13.

11) The anti-CD38 antibody for use according to embodiment 1, 2, 6-10, or the combination according to embodiment 3-10, wherein AML with at least one genetic abnormality, AML with multilineage dysplasia, therapy-related AML, undifferentiated AML, AML with minimal maturation, AML with maturation, acute myelomonocytic leukemia, acute monocytic leukemia, acute erythroid leukemia, acute megakaryoblastic leukemia, acute basophilic leukemia, acute panmyelosis with fibrosis or myeloid sarcoma.

12) The anti-CD38 antibody for use according to embodiment 1, 2, 6-11, or the combination according to embodiment 3-11, wherein the anti-CD38 antibody is administered as a remission induction, post-remission or maintenance therapy.

13) The anti-CD38 antibody for use according to embodiment 1, 2, 6-12, or the combination according to embodiment 3-12, wherein the at least one genetic abnormality is a translocation between chromosomes 8 and 21, a translocation or an inversion in chromosome 16, a translocation between chromosomes 15 and 17, changes in chromosome 11, or mutation in fms-related tyrosine kinase 3 (FLT3), nucleophosmin (NPM1), isocitrate dehydrogenase 1(IDH1), isocitrate dehydrogenase 2 (IDH2), DNA (cytosine-5)-methyltransferase 3 (DNMT3A), CCAAT/enhancer binding protein alpha (CEBPA), U2 small nuclear RNA auxiliary factor 1(U2AF1), enhancer of zeste 2 polycomb repressive complex 2 subunit (EZH2), structural maintenance of chromosomes 1A (SMC1A) or structural maintenance of chromosomes 3 (SMC3).

14) The anti-CD38 antibody for use according to embodiment 1, 2, 6-13, or the combination according to embodiment 3-13, wherein the at least one genetic abnormality is a translocation t(8; 21)(q22; q22), an inversion inv(16)(p13; q22), a translocation t(16; 16)(p13; q22), a translocation t(15; 17)(q22; q12), a mutation FLT3-ITD, mutations R132H or R100Q/R104V/F108L/R119Q/I130V in IDH1 or mutations R140Q or R172 in IDH2.

15) The anti-CD38 antibody for use according to embodiment 1, 2, 6-14, or the combination according to embodiment 3-14, wherein the anti-CD38 antibody and the at least one therapeutic agent are administered simultaneously, sequentially or separately.

16) The anti-CD38 antibody for use according to embodiment 1, 2, 6-15, or the combination according to embodiment 3-15, wherein
a. the subject is further treated or has been treated with radiotherapy; or
b. the subject has received hematopoietic stem cell transplantation.

EXAMPLES

Example 1. Efficacy of Daratumumab in AML Cell Lines

Several AML cell lines were used to evaluate surface expression of CD38 and possible efficacy of daratumumab in inducing AML cell killing. Expression of complement inhibitory proteins (CIP) CD46, CD55 and CD59 in the AML cell lines was assessed to evaluate possible correlation between expression of CIP and CDC.

Methods:

ADCC

In vitro ADCC assays were performed using AML tumor cell lines and Peripheral Blood Mononuclear Cells (PBMC) as effector cells at a ratio of 50:1. One hundred μl of target (tumor) cells ($1 \times 10^4$ cells) were added to wells of 96-well U-bottom plates. An additional 100 μl was added with or without antibody, and the plates were incubated for 30 minutes at room temperature (RT) before adding effector cells (PBMC). Seventy five μl of PBMCs at concentration $6.66 \times 10^6$ cells/ml was added to the wells of the plates, and the plates were incubated at 37° C. for 6 hours. Plates were centrifuged at 250 g for 4 minutes, 50 μl of supernatant removed per well and cell lysis was measured using the CellTiter-Glo® assay (Promega).

CDC

Target cells were harvested and adjusted to a concentration of $80 \times 10^4$ cells/ml. Twelve μl of target cells were added to wells of a 96-well plate, and serial dilution of antibodies added onto the cells. The wells were incubated for 15 minutes, after which human serum high in complement was added at a final concentration of 10%. Reaction mixture was incubated for 2 1/2 hours at 37° C., and cell lysis was measured using the CellTiter-Glo® assay (Promega).

Apoptosis

One ml of target cells ($5 \times 10^5$ cells/ml) were added to the well of a 24-well plate, together with test antibody (1 μg/ml) in the presence or absence of rabbit anti-huIgG (10 μg/ml; $F(ab')_2$ Fcγ-specific). Cells were incubated for 22 hours (5% $CO_2$, 37° C.). Thereafter, cells were harvested (1000 rpm, 5 min) and washed twice in PBS (1000 rpm, 5 min). Cells were resuspended in 250 μl binding buffer (Annexin-V Apoptosis kit, BD Biosciences) according to manufacturer's instruction, followed by flow cytometry analysis.

Figure 1B:
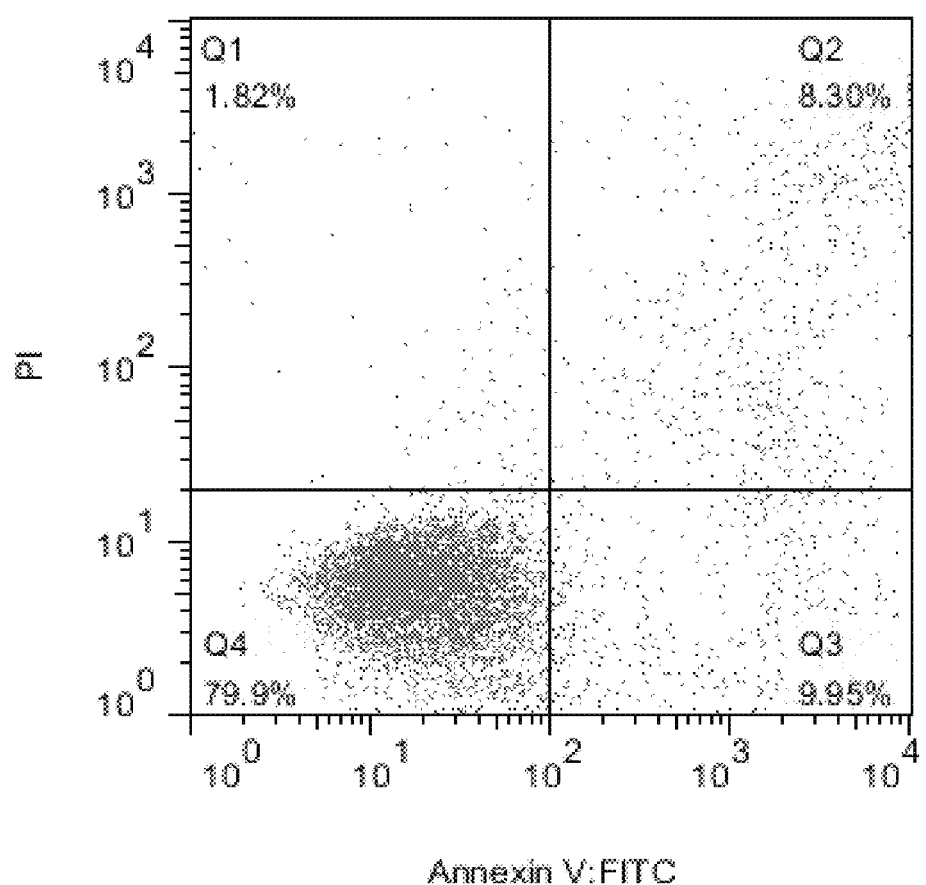
FIG. 1B shows daratumumab-induced apoptosis in the presence of crosslinking in NB-4 AML cell line. PI: propidium iodide.

Apoptosis was measured by both early and late apoptosis (Q2 and Q3 in FIG. 1A and FIG. 1B).

CD38, CD46, CD55 and CD59 Surface Expression

Expression of receptors was analyzed by flow cytometry. The CD38 receptor number per cell was estimated using MESF kit using PE-labeled anti-CD38 antibody (R&D Systems). The receptor numbers were calculated as follows: Specific MESF/ABC=MESF/ABC (Test Antibody)—MESF/ABC (Isotype control antibody).

CD46, CD55 and CD59, surface expression was detected using FITC anti-human CD46, PE-anti-human CD55 and PE-anti-human CD59 antibodies (Beckton Dickinson) expressed as median fluorescent intensity (MFI).

Results

Table 1 shows the results of the experiments. FIG. 1 shows representative flow cytometry results of daratumumab-induced apoptosis in NB-4 cell line without (FIG. 1A) or with (FIG. 1B) crosslinking antibody. In this cell line, daratumumab induced apoptosis to a similar degree independent of the presence of the crosslinking agent (19.2% vs 18.3%).

In the AML cell lines, daratumumab did not induce significant ADCC or CDC; instead; daratumumab induced AML cell killing by apoptosis. In addition, no direct correlation was observed between CD38 expression and the extent of ADCC and CDC. The levels of complement inhibitory proteins (CIP) (CD46, CD55 and CD59) were evaluated to determine if these proteins affected CDC in response to daratumumab but no direct correlation was observed between CDC and CIP expression.

TABLE 1

| Cell line | CD38#/cell | CD46 MFI | CD55 MFI | CD59 MFI | Apoptosis | CDC | ADCC |
|---|---|---|---|---|---|---|---|
| HL-60 | 64.50 | ND | ND | ND | ND | ND | ND |
| Kasumi-1 | 120.2 | ND | ND | ND | ND | ND | ND |
| ML-2 | 1,253.27 | 21.53 | 195.2 | 0.98 | 5% | 0% | 6.30% |
| MOLM-13 | 5,634.29 | 35.53 | 173.2 | 9.45 | 10-15% | 0% | 9.40% |
| MOLM-16 | 52,461.11 | 42.18 | 886.4 | 350.42 | 20-30% | 5% | 18.20% |
| MV-4-11 | 5,700.05 | 207.17 | 395.42 | 43.94 | 10-12% | 0% | 2.30% |
| NB4 | 9,370.73 | 58.25 | 345.4 | 66.2 | 18% | 4% | 18.30% |
| THP-1 | 39,488.19 | 58.7 | 375 | 27.1 | 5-7% | 5% | 11.30% |

ND: not done
MFI: mean fluorescence intensity

Example 2. ATRA Induces CD38 Expression on AML Cells

Effect of ATRA on CD38 surface expression was assessed in NB-4 AML cell line. Tumor cells were incubated at 37° C. for 24 hours in the presence or absence of 10 nM or 100 nM ATRA. After 24 hour incubation, the cells were harvested and stained for CD38. ATRA induced ~10-fold increase in CD38 receptors in the NB-4 cell line. CD38 surface expression was assessed using FACS using PE-labeled anti-CD38 antibody (R&D Systems) (Table 2).

TABLE 2

| Treatment | PE-CD38 molecules/cell |
|---|---|
| DMSO | 17238 |
| 10 nM ATRA | 185737 |
| 100 nM ATRA | 210570 |

Example 3. Efficacy of Daratumumab in Patient-Derived Xenograft (PDX) Models Methods Patient tumor models AML 3406, AML 7577 and AML 8096 were used in the study.

AML3406 model: Patient tumor cells were positive for FLT-3ITD. Patient has a history of polycythemia versa, and received idarubicin/cytrabine for induction chemotherapy. Patient also received Hudrea® (hydroxyurea).

AML 7577 model: Leukemic cells were collected from a 69-year old male with AML (FAB subtype M5). Patient had normal karyotype and following mutations: IDH2(R140Q); FLT3-ITD; DNMT3A R882H, NPM1, CEBPA insertion (SNP). Patient has a history of polycythemia versa, and received idarubicin/cytrabine for induction chemotherapy. Patient also received Hudrea® (hydroxyurea).

AML 8096 model: Leukemic cells were collected from a 21-year old male with AML (FAB subtype M2). White blood cell count was 20×10e$^9$/L, from which 70% were blast cells. Patient had normal karyotype with wild type TP53, FLT3, NPM1, and insertion 570-587, 3GCACCC>4GCACCC in CEBPA exon1. Patient has a history of polycythemia versa, and received idarubicin/cytrabine for induction chemotherapy. Patient also received Hudrea® (hydroxyurea).

Figure 2A:
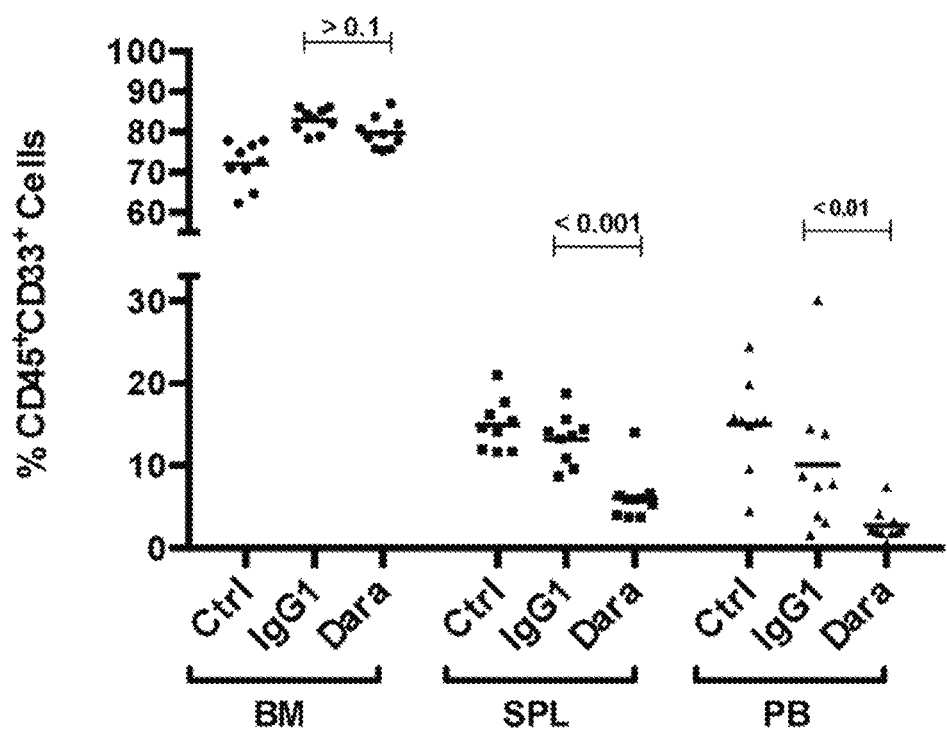
FIG. 2A shows the efficacy of daratumumab in patient-derived xenograft (PDX) AML 3406 model as measured by reduction in percentage (%) leukemic $CD45^+CD33^+$ cells in bone marrow (BM), spleen (SPL) and peripheral blood (PB). Ctrl: no treatment; IgG1: isotype control; Dara: daratumumab. p values are indicated in the Figure (isotype control vs. daratumumab).
Figure 2B:
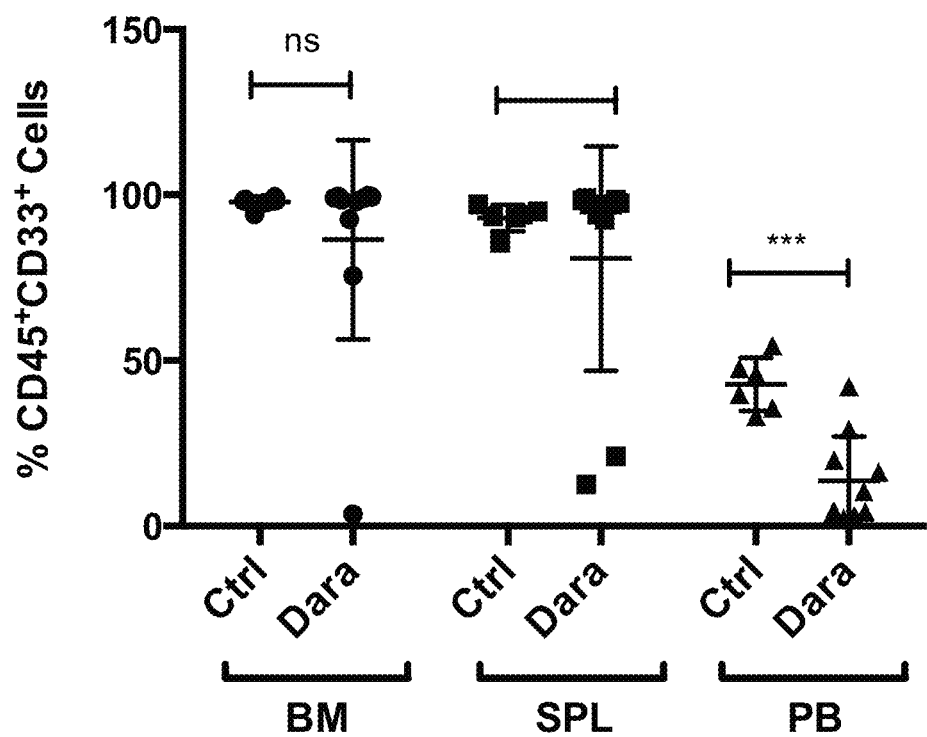
FIG. 2B shows the efficacy of daratumumab in patient-derived xenograft (PDX) AML 7577 model as measured by reduction in percentage (%) leukemic $CD45^+CD33^+$ cells in bone marrow (BM), spleen (SPL) and peripheral blood (PB). Ctrl: no treatment; IgG1: isotype control; Dara: daratumumab. ns: not significant. ***$p<0.001$
Figure 2C:
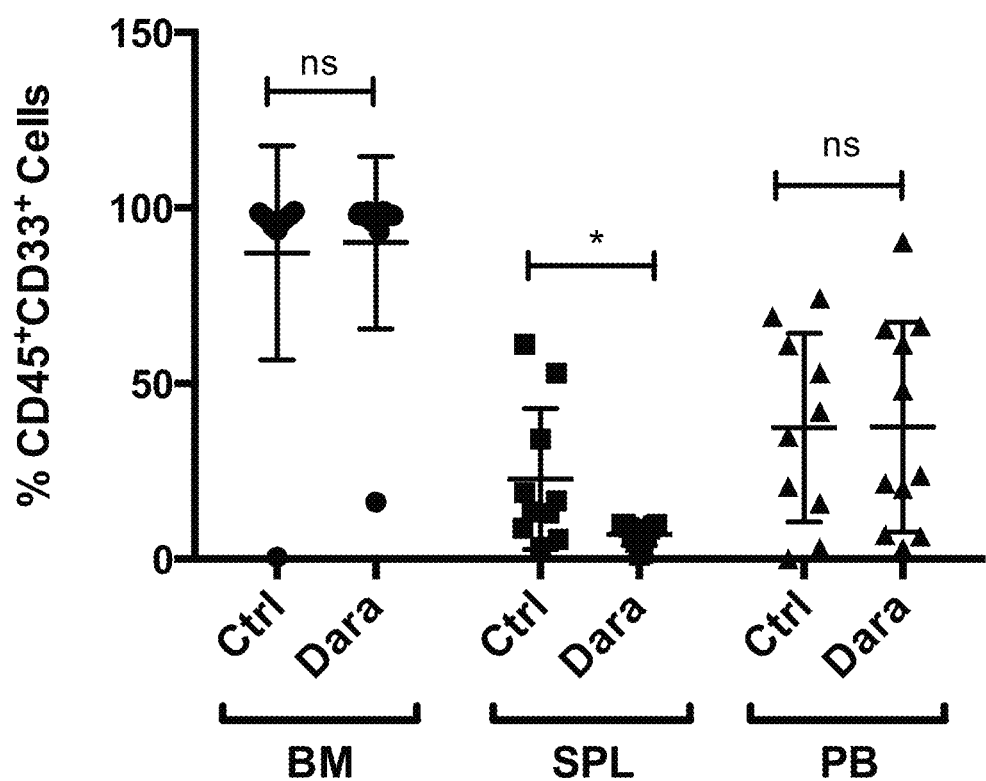
FIG. 2C shows the efficacy of daratumumab in patient-derived xenograft (PDX) AML 8096 model, assessed by reduction in percentage (%) leukemic $CD45^+CD33^+$ cells in bone marrow (BM), spleen (SPL) and peripheral blood (PB). Ctrl: no treatment; IgG1: isotype control; Dara: daratumumab. ns: not significant. *$p<0.05$
Figure 3A:
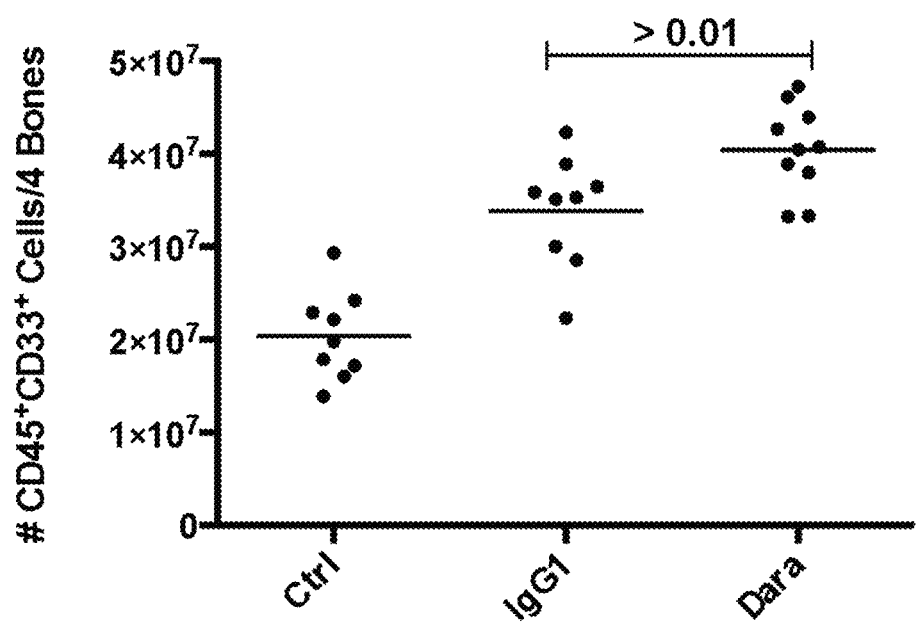
FIG. 3A shows the efficacy of daratumumab in patient-derived xenograft (PDX) AML 3406 model, assessed by reduction in total leukemic burden in bone marrow (number of $CD45^+CD33^+$ cells per four bones). Ctrl: no treatment; IgG1: isotype control; Dara: daratumumab. There was no significant difference ($p>0.01$) in bone marrow leukemic burden between Ctrl and Dara. p value between isotype control vs daratumumab treatment groups shown.
Figure 3B:
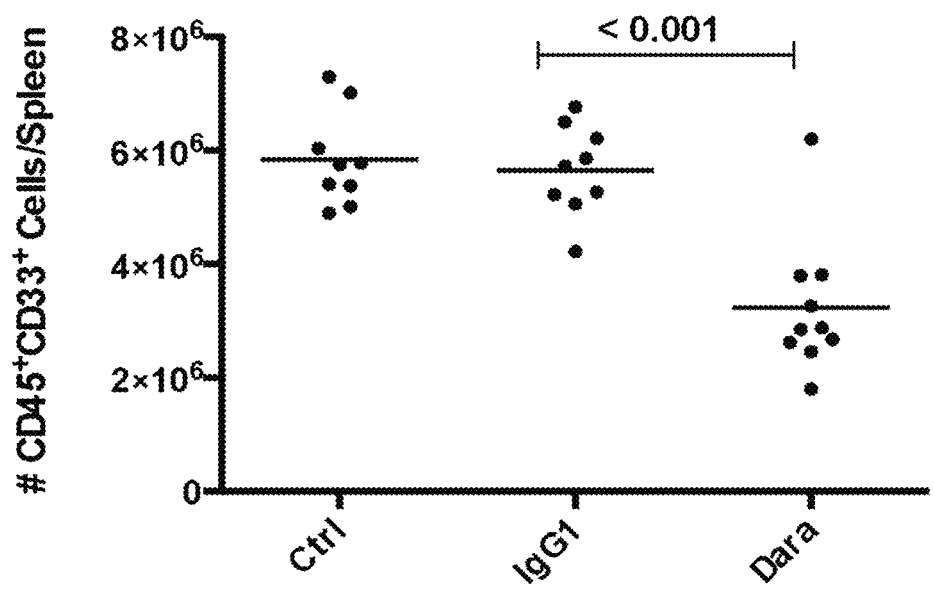
FIG. 3B shows the efficacy of daratumumab in patient-derived xenograft (PDX) AML 3406 model, assessed by reduction in total leukemic burden in spleen (number of $CD45^+CD33^+$ cells per spleen). Ctrl: no treatment; IgG1: isotype control; Dara: daratumumab. p value between isotype control vs daratumumab treatment groups shown.

5 million AML MNCs were T-cell depleted and transplanted via tail vein into 6-8 weeks old sub-lethally irradiated NSG mice (n=10 per group). 4 to 6 weeks post-engraftment, bone marrow aspirates were collected from each mouse and were analyzed by flow cytometry to determine the level of leukemia engraftment (% of human $CD45^+CD33^{+/-}$ cells). Based on engraftment levels, mice were randomized and conditioned with either IgG1 or daratumumab (DARA, pre-dosing at 0.5 mg/kg). 24 hours later, mice were untreated (Ctrl) or treated for 5 consecutive weeks with DARA or IgG1 alone (i.p, 10 mg/kg once a week). 2-3 days after the last treatment, mice were sacrificed and bone marrow, spleen, peripheral blood and plasma were collected for analysis. Flow cytometry was performed to assess percentage of human $CD45^+CD33^+$ cells in the BM, SPL and PB of 3 AML patients engrafted in NSG mice (AML 3406 model: FIG. 2A; AML 7577 model: FIG. 2B, AML 8096 model: FIG. 2C) and absolute number of the human $CD45^+CD33^+$ cells in bone marrow (FIG. 3A), spleen (FIG. 3B) and peripheral blood (FIG. 3C) of one representative AML patient.

Results

FIG. 2A, FIG. 2B and FIG. 2C show the efficacy of daratumumab in the AML 3406 model, AML 7577 model and the AML 8096 model, respectively, assessed by reduction in % leukemic $CD45^+CD33^+$ cells in bone marrow, spleen or peripheral blood. Daratumumab reduced tumor burden in spleen and peripheral blood in the AML 3406 model (FIG. 2A), in peripheral blood in the AML 7577 model (FIG. 2B), and in spleen in the AML 8096 model (FIG. 2C).

Figure 3C:
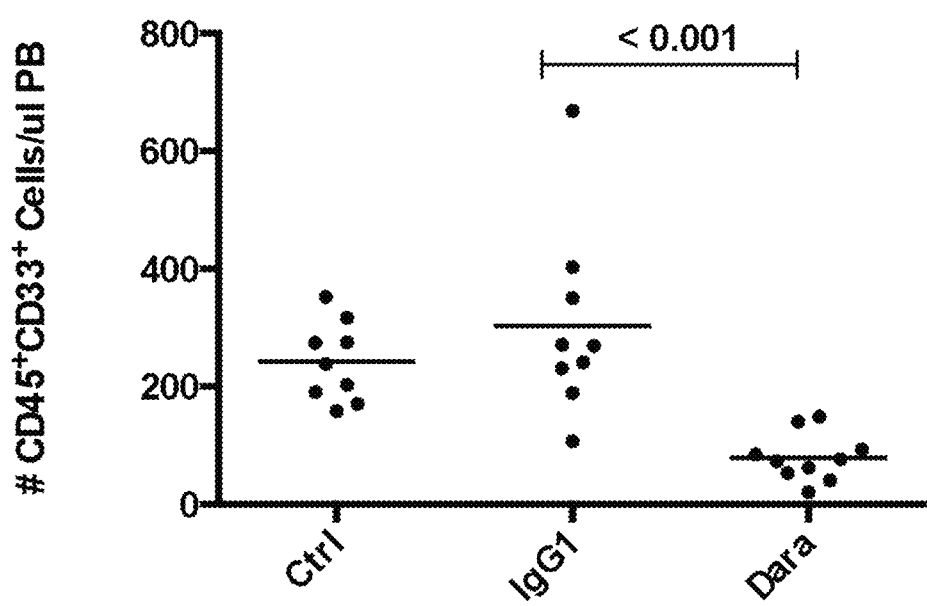
FIG. 3C shows the efficacy of daratumumab in patient-derived xenograft (PDX) AML 3406 model, assessed by reduction in total leukemic burden in peripheral blood (number of $CD45^+CD33^+$ cells per µl blood). Ctrl: no treatment; IgG1: isotype control; Dara: daratumumab. p value between isotype control vs daratumumab treatment groups is indicated.

Efficacy of daratumumab was also assessed by measuring daratumumab-induced reduction in total leukemic burden in bone marrow (FIG. 3A), spleen (FIG. 3B) and blood (FIG. 3C) in the AML 3406 model. Daratumumab significantly reduced total leukemic burden in the AML 3406 model in spleen (FIG. 3B) and in peripheral blood (FIG. 3C).

Example 4. Effect of Daratumumab on CD38 Expression on AML Blasts

Effect of daratumumab on CD38 expression on leukemic blasts was assessed in one representative AML model described in Example 3 after 5 weeks of treatment with daratumumab or isotype control using PE-labeled anti-CD38 antibody (R&D Systems).

Results

Figure 4A:
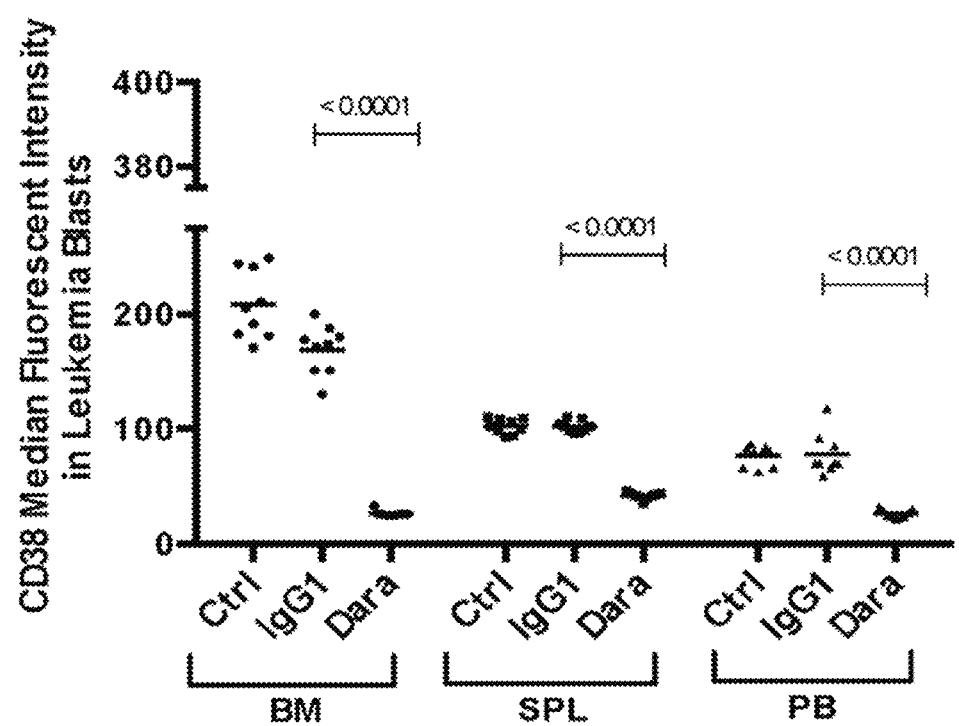
FIG. 4A shows daratumumab-induced downregulation of surface CD38 expression in patient-derived xenograft (PDX) AML 3406 model in bone marrow (BM), spleen (SPL) and peripheral blood (PB) after 5 weeks of treatment with daratumumab. Ctrl: no treatment; IgG1: isotype control; Dara: daratumumab. p values as indicated in the Figure for isotype control vs. daratumumab.
Figure 4B:
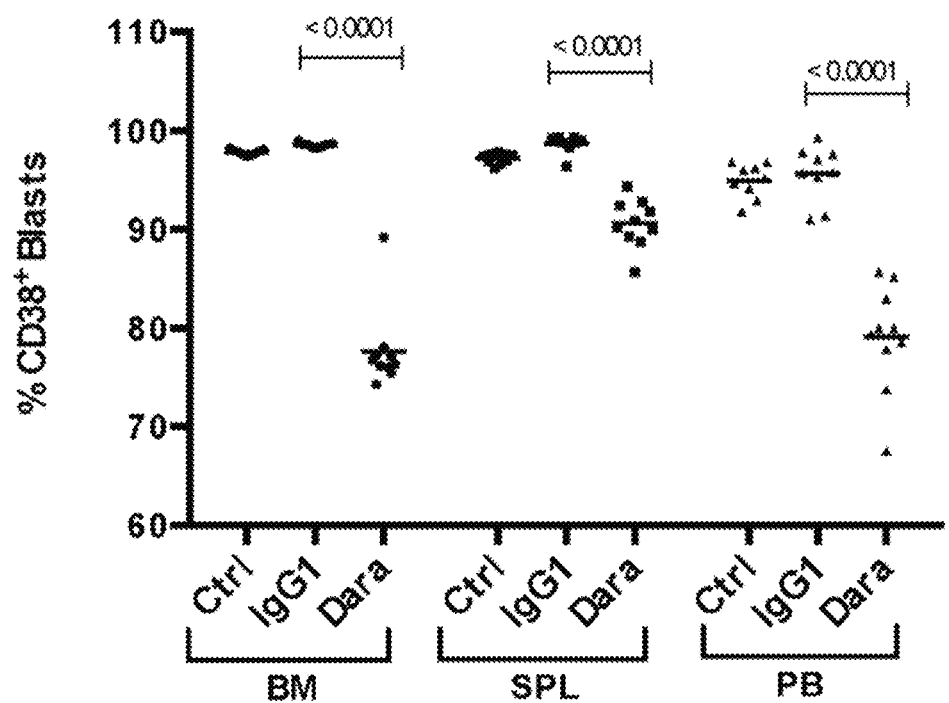
FIG. 4B shows daratumumab-induced reduction in the percentage of CD38-positive leukemia blasts in patient-derived xenograft (PDX) AML 3406 model in bone marrow (BM), spleen (SPL) and peripheral blood (PB) after 5 weeks of treatment with daratumumab. Ctrl: no treatment; IgG1: isotype control; Dara: daratumumab. p values are indicated in between isotype control vs. daratumumab treatment groups.

FIG. 4A shows that treatment with daratumumab reduced expression of CD38 on leukemia blasts ($CD45^+CD33^+$ positive cells) in bone marrow, spleen and peripheral blood. FIG.

4B shows that percentage of CD38-positive AML blasts were reduced after 5 weeks of treatment.

Example 5. Efficacy of Daratumumab Combination Therapy in Patient-Derived Xenograft (PDX) Models Efficacy of daratumumab in combination with dacogen or cytarabine and doxorubicin was assessed after 5 weeks of treatment.

Figure 5A:
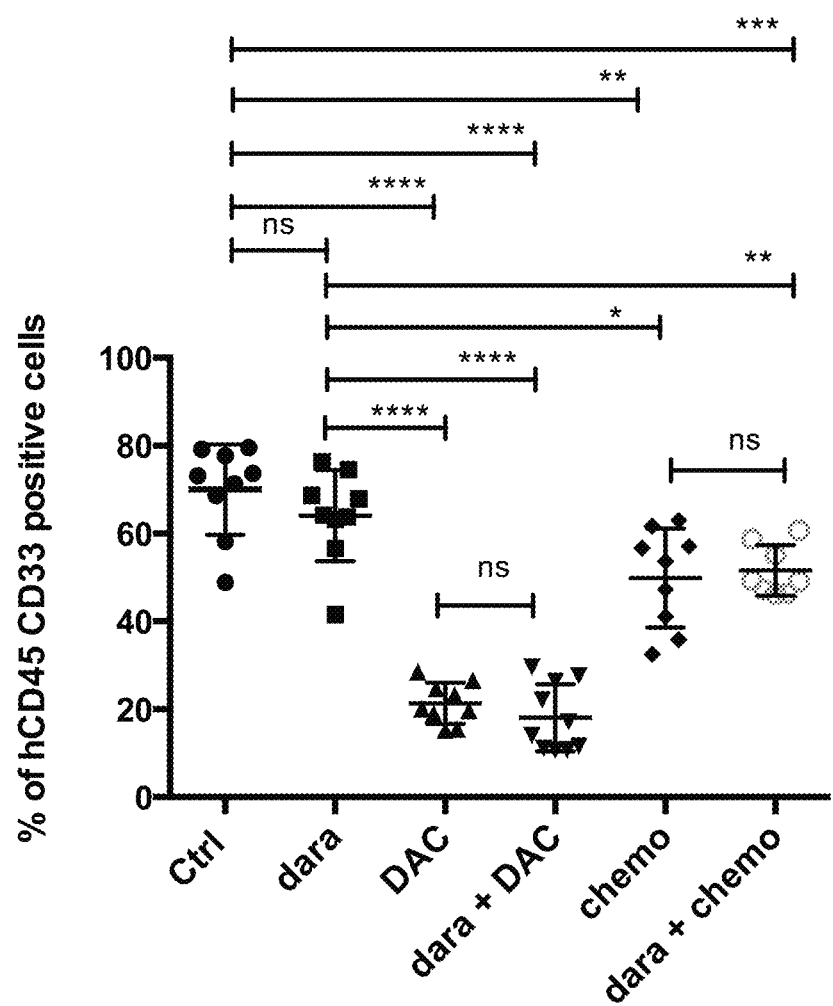
FIG. 5A shows the efficacy of daratumumab (dara) alone or in combination with dacogen (DAC) or cytrabine and doxorubicin (chemo) in reducing leukemia burden in patient-derived xenograft (PDX) 3406 model in bone marrow. Leukemia burden was assessed as % of $CD45^+CD33^+$ cells. Ctrl: isotype control. *$p<0.05$; $p<0.01$; *$p<0.001$. ns: not significant.
Figure 5B:
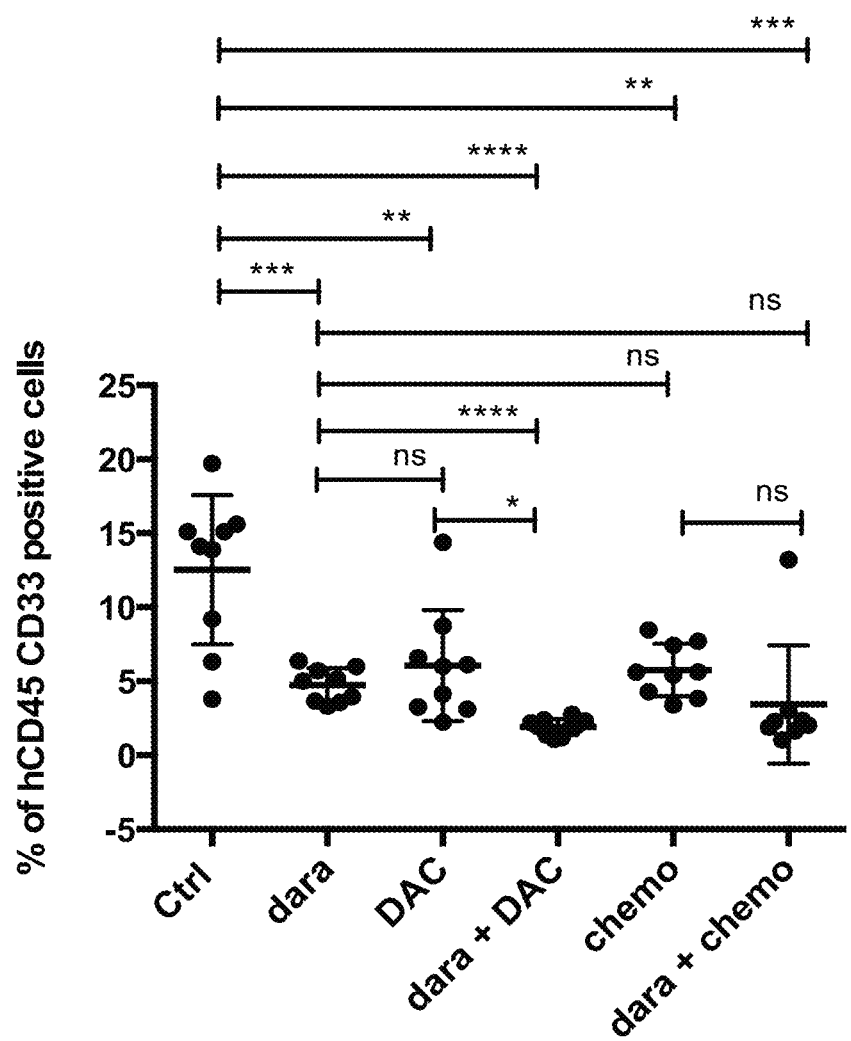
FIG. 5B shows the efficacy of daratumumab (dara) alone or in combination with dacogen (DAC) or cytrabine and doxorubicin (chemo) in reducing leukemia burden in patient-derived xenograft (PDX) 3406 model in spleen. Leukemia burden was assessed as % of CD45$^+$CD33$^+$ cells. Ctrl: isotype control. *p<0.05; p<0.01; *p<0.001. ns: not significant.
Figure 5C:
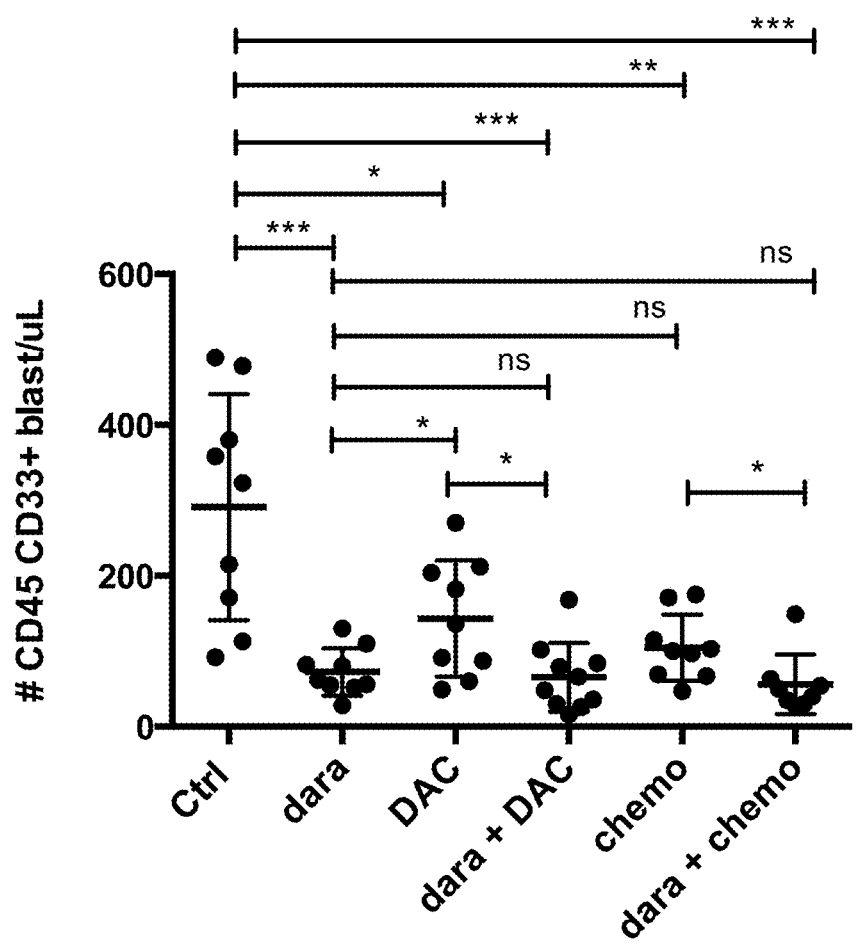
FIG. 5C shows the efficacy of daratumumab (dara) alone or in combination with dacogen (DAC) or cytrabine and doxorubicin (chemo) in reducing leukemia burden in patient-derived xenograft (PDX) model in peripheral blood. Leukemia burden was assessed as % of CD45$^+$CD33$^+$ cells. Ctrl: isotype control. *p<0.05; p<0.01; *p<0.001. ns: not significant.

5 million AML MNCs were T-cell depleted and transplanted via tail vein into 6-8 weeks old NSG mice (n=10 per group). 4 to 6 weeks post-engraftment, bone marrow aspirates were collected from each mouse and were analyzed by flow cytometry to determine the level of leukemia engraftment (% of human $CD45^+CD33^{+/-}$ cells). Based on engraftment levels, mice were equally randomized and conditioned with either IgG1 or DARA (pre-dosing at 0.5 mg/kg). 24 hours later, mice were treated with IgG1 alone (i.p, 10 mg/kg) once a week for five weeks, with DARA alone (i.p, 10 mg/kg) once a week for five weeks, with decitabine alone (DAC) (0.5 mg/kg/day, i.p. for 3 consecutive days) for five weeks, with DAC+DARA (each week will consist of 3 consecutive days of DAC followed by DARA 2 days later), with a combination of cytarabine (i.v, 50 mg/kg) and doxorubicin (i.v, 1.5 mg/kg) (3 consecutive days doxorubicin (i.v, 1.5 mg/kg) plus cytarabine (50 mg/kg) for 3 days) with or without DARA. 2-3 days after the last treatment, mice were sacrificed and bone marrow, spleen, peripheral blood and plasma were collected for analysis. Flow cytometry was performed to assess percentage of human $CD45^+CD33^+$ cells in the bone marrow (FIG. 5A), spleen (FIG. 5B) and peripheral blood (FIG. 5C) of one AML patient engrafted in NSG mice.

Figure 6A:
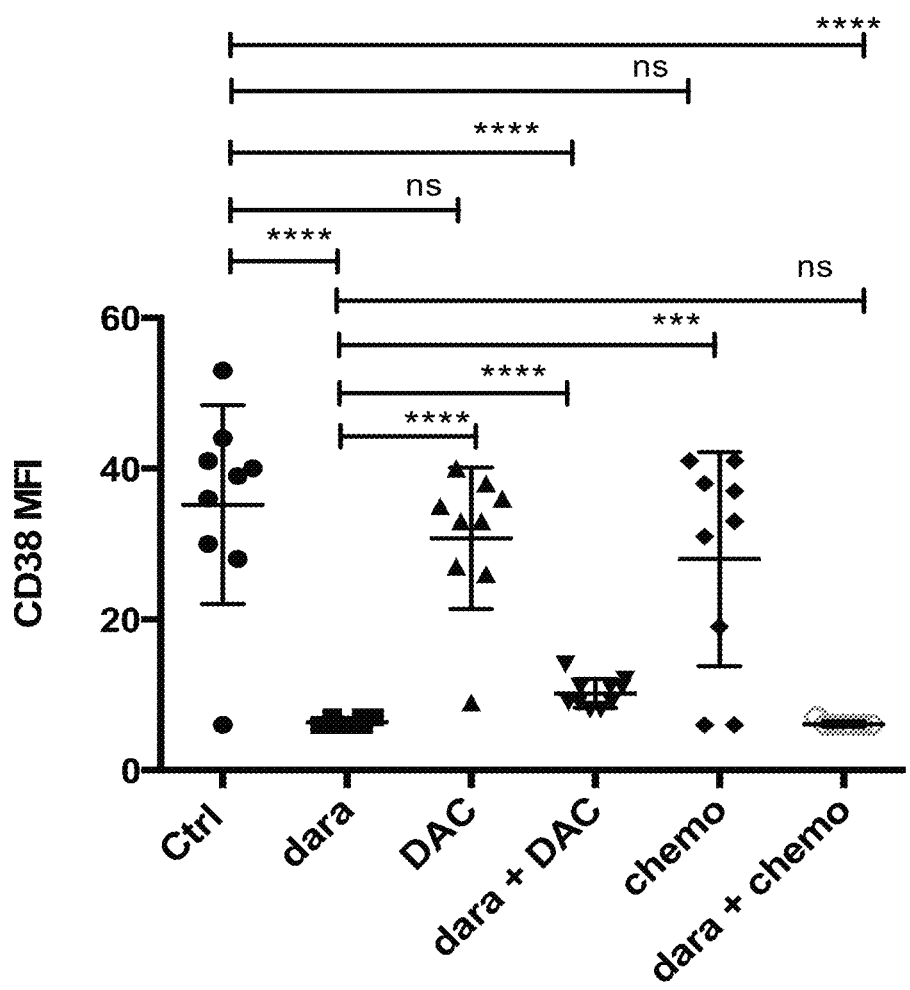
FIG. 6A shows the effect of daratumumab (dara) alone or in combination with dacogen (DAC) or cytrabine and doxorubicin (chemo) on CD38 expression on CD45$^+$CD33$^+$ AML bone marrow blasts in patient derived xenograft (PDX) 3406 model. Leukemia burden was assessed as % of CD45$^+$CD33$^+$ cells. Ctrl: isotype control. *p<0.05; p<0.01; *p<0.001. ns: not significant. MFI: mean fluorescent intensity.
Figure 6B:
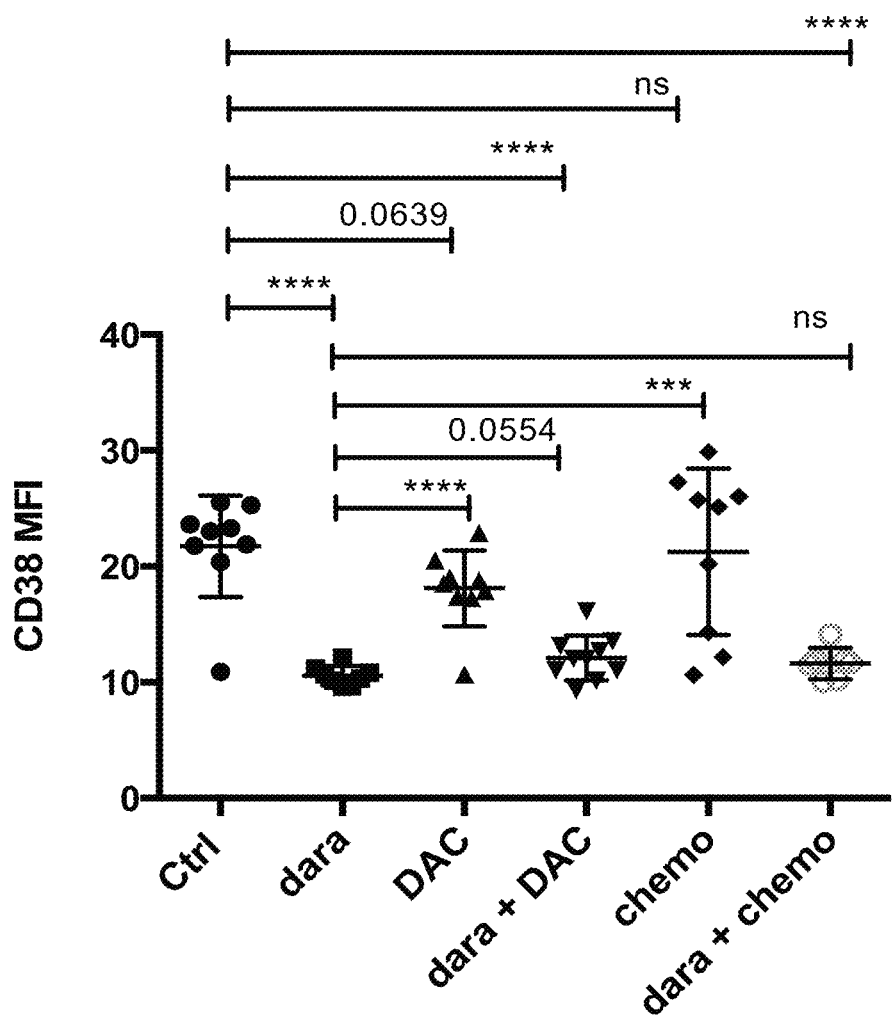
FIG. 6B shows the effect of daratumumab (dara) alone or in combination with dacogen (DAC) or cytrabine and doxorubicin (chemo) on CD38 expression on CD45$^+$CD33$^+$ AML spleen blasts in patient derived xenograft (PDX) 3406 model. Leukemia burden was assessed as % of CD45$^+$CD33$^+$ cells. Ctrl: isotype control. *p<0.05; p<0.01; *p<0.001. ns: not significant.
Figure 6C:
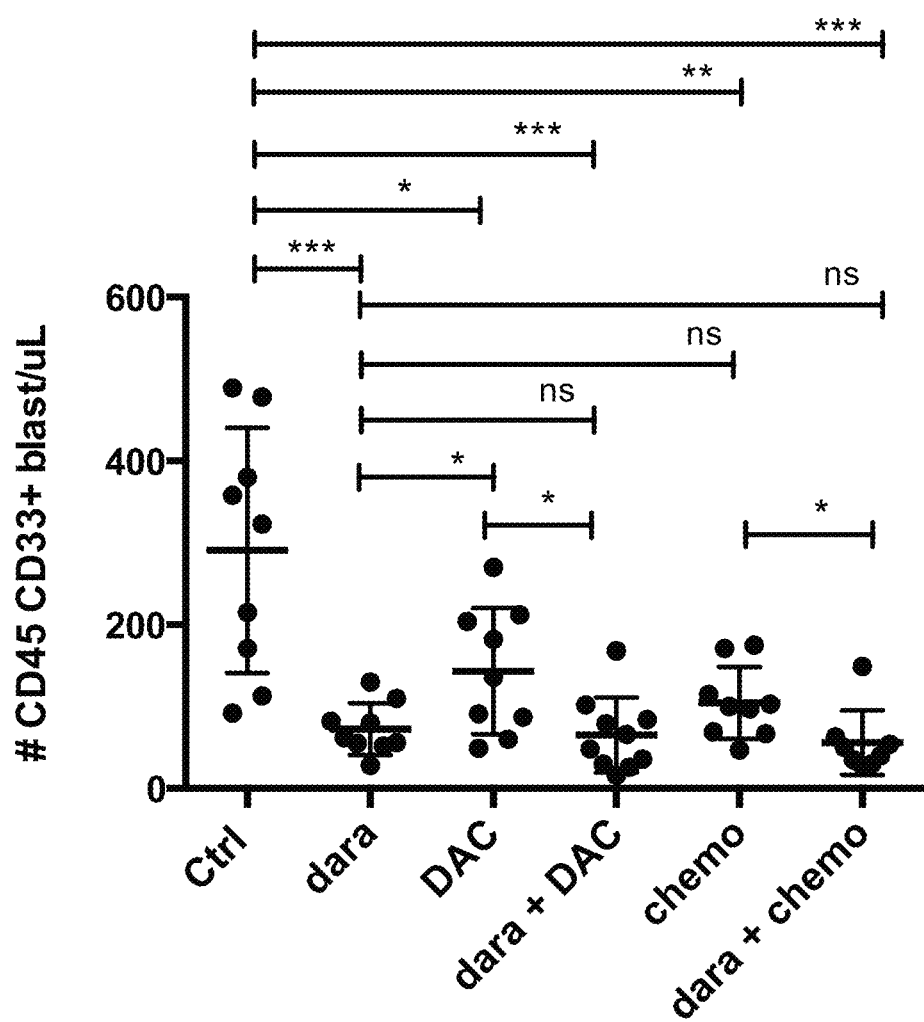
FIG. 6C shows the effect of daratumumab (dara) alone or in combination with dacogen (DAC) or cytrabine and doxorubicin (chemo) on CD38 expression on CD45$^+$CD33$^+$ AML peripheral blood blasts in patient derived xenograft (PDX) 3406 model. Leukemia burden was assessed as % of CD45$^+$CD33$^+$ cells. Ctrl: isotype control. *p<0.05; p<0.01; *p<0.001. ns: not significant.

CD38 expression (expressed as mean fluorescence intensity, MFI) was evaluated in the bone marrow (FIG. 6A), spleen (FIG. 6B) and peripheral blood (FIG. 6C) after 5 week treatment with the indicated drugs.

We claim:

1. A method of treating relapsed or refractory acute myeloid leukemia (AML) in a subject in need thereof, comprising administering to the subject an anti-CD38 antibody:
   b) for a time sufficient to treat the relapsed or refractory AML, wherein the anti-CD38 antibody consists of daratumumab, and wherein the AML is AML with at least one mutation in a gene selected from the group consisting of fms-related tyrosine kinase 3 (FLT3), nucleophosmin (NPM1), isocitrate dehydrogenase 2 (IDH2), DNA (cytosine-5) methyltransferase 3 (DNMT3A) and CCAAT/enhancer binding protein alpha (CEBPA).

2. The method of claim 1, wherein the anti-CD38 antibody induces killing of AML cells that express CD38 by apoptosis.

3. The method of claim 1, wherein the anti-CD38 antibody is administered as a remission induction, post-remission or maintenance therapy.

4. The method of claim 1, wherein the AML is AML with a mutation in FLT3, and wherein the mutation in FLT3 is FLT3-ITD.

5. The method of claim 1, wherein the AML is AML with a mutation in IDH2, and wherein the mutation in IDH2 is R140Q.

6. The method of claim 1, wherein the AML is AML with a mutation in DNMT3A, and wherein the mutation in DNMT3A is R882H.

7. The method of claim 1, wherein the AML is AML with multilineage dysplasia, therapy-related AML, undifferentiated AML, AML with minimal maturation, AML with maturation, acute myelomonocytic leukemia, acute monocytic leukemia, acute erythroid leukemia, acute megakaryoblastic leukemia, acute basophilic leukemia, acute panmyelosis with fibrosis or myeloid sarcoma.

8. The method of claim 1, wherein the subject has been treated with idarubicin.

9. The method of claim 1, wherein the subject has been treated with cytarabine.

10. The method of claim 1, wherein the subject has been treated with hydroxyurea.

11. The method of claim 1, wherein the subject is further treated or has been treated with radiotherapy.

12. The method of claim 1, wherein the subject has been treated with idarubicin, cytarabine, and hydroxyurea.

* * * * *

```
                        SEQUENCE LISTING

<160> NUMBER OF SEQ ID NOS: 22

<210> SEQ ID NO 1
<211> LENGTH: 300
<212> TYPE: PRT
<213> ORGANISM: Homo sapiens

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240
```

```
Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 2
<211> LENGTH: 14
<212> TYPE: PRT
<213> ORGANISM: Homo sapiens

<400> SEQUENCE: 2

Ser Lys Arg Asn Ile Gln Phe Ser Cys Lys Asn Ile Tyr Arg
1               5                   10

<210> SEQ ID NO 3
<211> LENGTH: 14
<212> TYPE: PRT
<213> ORGANISM: Homo sapiens

<400> SEQUENCE: 3

Glu Lys Val Gln Thr Leu Glu Ala Trp Val Ile His Gly Gly
1               5                   10

<210> SEQ ID NO 4
<211> LENGTH: 122
<212> TYPE: PRT
<213> ORGANISM: Artificial Sequence
<220> FEATURE:
<223> OTHER INFORMATION: antibody VH

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120

<210> SEQ ID NO 5
<211> LENGTH: 107
<212> TYPE: PRT
<213> ORGANISM: Artificial Sequence
<220> FEATURE:
<223> OTHER INFORMATION: Antibody VL

<400> SEQUENCE: 5
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

<210> SEQ ID NO 6
<211> LENGTH: 5
<212> TYPE: PRT
<213> ORGANISM: Artificial Sequence
<220> FEATURE:
<223> OTHER INFORMATION: Antibody HCDR1

<400> SEQUENCE: 6

```
Ser Phe Ala Met Ser
1               5
```

<210> SEQ ID NO 7
<211> LENGTH: 17
<212> TYPE: PRT
<213> ORGANISM: Artificial Sequence
<220> FEATURE:
<223> OTHER INFORMATION: Antibody HCDR2

<400> SEQUENCE: 7

```
Ala Ile Ser Gly Ser Gly Gly Thr Tyr Tyr Ala Asp Ser Val Lys
1               5                   10                  15

Gly
```

<210> SEQ ID NO 8
<211> LENGTH: 13
<212> TYPE: PRT
<213> ORGANISM: Artificial Sequence
<220> FEATURE:
<223> OTHER INFORMATION: Antibody HCDR3

<400> SEQUENCE: 8

```
Asp Lys Ile Leu Trp Phe Gly Glu Pro Val Phe Asp Tyr
1               5                   10
```

<210> SEQ ID NO 9
<211> LENGTH: 11
<212> TYPE: PRT
<213> ORGANISM: Artificial Sequence
<220> FEATURE:
<223> OTHER INFORMATION: Antibody LCDR1

<400> SEQUENCE: 9

```
Arg Ala Ser Gln Ser Val Ser Ser Tyr Leu Ala
1               5                   10
```

<210> SEQ ID NO 10
<211> LENGTH: 7
<212> TYPE: PRT

```
<213> ORGANISM: Artificial Sequence
<220> FEATURE:
<223> OTHER INFORMATION: Antibody LCDR2

<400> SEQUENCE: 10

Asp Ala Ser Asn Arg Ala Thr
1               5

<210> SEQ ID NO 11
<211> LENGTH: 10
<212> TYPE: PRT
<213> ORGANISM: Artificial Sequence
<220> FEATURE:
<223> OTHER INFORMATION: Antibody LCDR3

<400> SEQUENCE: 11

Gln Gln Arg Ser Asn Trp Pro Pro Thr Phe
1               5                   10

<210> SEQ ID NO 12
<211> LENGTH: 452
<212> TYPE: PRT
<213> ORGANISM: Artificial Sequence
<220> FEATURE:
<223> OTHER INFORMATION: Antibody HC

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 13
<211> LENGTH: 214
<212> TYPE: PRT
<213> ORGANISM: Artificial Sequence
<220> FEATURE:
<223> OTHER INFORMATION: Antibody LC

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 14
<211> LENGTH: 4
<212> TYPE: PRT
<213> ORGANISM: Homo sapiens

<400> SEQUENCE: 14

Val Gln Leu Thr
1

<210> SEQ ID NO 15
<211> LENGTH: 122
<212> TYPE: PRT
<213> ORGANISM: Artificial Sequence
<220> FEATURE:
<223> OTHER INFORMATION: Antibody VH

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
            35                  40                  45

Gly Arg Val Ile Pro Phe Leu Gly Ile Ala Asn Ser Ala Gln Lys Phe
        50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
            85                  90                  95

Ala Arg Asp Asp Ile Ala Ala Leu Gly Pro Phe Asp Tyr Trp Gly Gln
            100                 105                 110

Gly Thr Leu Val Thr Val Ser Ser Ala Ser
            115                 120

<210> SEQ ID NO 16
<211> LENGTH: 107
<212> TYPE: PRT
<213> ORGANISM: Artificial Sequence
<220> FEATURE:
<223> OTHER INFORMATION: Antibody VL

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 17
<211> LENGTH: 122
<212> TYPE: PRT
<213> ORGANISM: Artificial Sequence
<220> FEATURE:
<223> OTHER INFORMATION: Antibody VH

<400> SEQUENCE: 17

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
                20                  25                  30

Trp Ile Gly Trp Val Arg Gln Met Pro Gly Lys Gly Leu Glu Trp Met
            35                  40                  45

Gly Ile Ile Tyr Pro His Asp Ser Asp Ala Arg Tyr Ser Pro Ser Phe
        50                  55                  60

Gln Gly Gln Val Thr Phe Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Gly Trp Gly Ser Arg Tyr Trp Tyr Phe Asp Leu Trp
            100                 105                 110

Gly Arg Gly Thr Leu Val Thr Val Ser Ser
        115                 120

<210> SEQ ID NO 18
<211> LENGTH: 107
<212> TYPE: PRT
<213> ORGANISM: Artificial Sequence
<220> FEATURE:
<223> OTHER INFORMATION: Antibody VL

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Gly Leu Leu Ile
            35                  40                  45

Tyr Asp Ala Ser Asn Arg Ala Ser Gly Ile Pro Ala Arg Phe Ser Gly
        50                  55                  60

Ser Gly Ser Gly Thr Asp Phe Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 19
<211> LENGTH: 120
<212> TYPE: PRT

<213> ORGANISM: Artificial Sequence
<220> FEATURE:
<223> OTHER INFORMATION: Antibody VH

<400> SEQUENCE: 19

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gly Ile Ser Gly Asp Pro Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120
```

<210> SEQ ID NO 20
<211> LENGTH: 109
<212> TYPE: PRT
<213> ORGANISM: Artificial Sequence
<220> FEATURE:
<223> OTHER INFORMATION: Antibody VL

<400> SEQUENCE: 20

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg His Tyr Tyr Val
            20                  25                  30

Tyr Trp Tyr Gln Gln Lys Pro Gly Gln Ala Pro Val Leu Val Ile Tyr
        35                  40                  45

Gly Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Gly Gly Ala Ser Leu
                85                  90                  95

Val Phe Gly Gly Gly Thr Lys Leu Thr Val Leu Gly Gln
            100                 105
```

<210> SEQ ID NO 21
<211> LENGTH: 120
<212> TYPE: PRT
<213> ORGANISM: Artificial Sequence
<220> FEATURE:
<223> OTHER INFORMATION: Antibody VH

<400> SEQUENCE: 21

```
Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45
```

```
Gly Thr Ile Tyr Pro Gly Asp Gly Asp Thr Gly Tyr Ala Gln Lys Phe
            50                  55                  60

Gln Gly Lys Ala Thr Leu Thr Ala Asp Lys Ser Ser Lys Thr Val Tyr
 65                  70                  75                  80

Met His Leu Ser Ser Leu Ala Ser Glu Asp Ser Ala Val Tyr Tyr Cys
                 85                  90                  95

Ala Arg Gly Asp Tyr Tyr Gly Ser Asn Ser Leu Asp Tyr Trp Gly Gln
                100                 105                 110

Gly Thr Ser Val Thr Val Ser Ser
            115                 120

<210> SEQ ID NO 22
<211> LENGTH: 107
<212> TYPE: PRT
<213> ORGANISM: Artificial Sequence
<220> FEATURE:
<223> OTHER INFORMATION: Antibody VL

<400> SEQUENCE: 22

Asp Ile Val Met Thr Gln Ser His Leu Ser Met Ser Thr Ser Leu Gly
 1               5                  10                  15

Asp Pro Val Ser Ile Thr Cys Lys Ala Ser Gln Asp Val Ser Thr Val
                20                  25                  30

Val Ala Trp Tyr Gln Gln Lys Pro Gly Gln Ser Pro Arg Arg Leu Ile
             35                  40                  45

Tyr Ser Ala Ser Tyr Arg Tyr Ile Gly Val Pro Asp Arg Phe Thr Gly
 50                  55                  60

Ser Gly Ala Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Pro Pro Tyr
                 85                  90                  95

Thr Phe Gly Gly Gly Thr Lys Leu Glu Ile Lys
                100                 105
```